US011646119B2

(12) United States Patent
Tran et al.

(10) Patent No.: US 11,646,119 B2
(45) Date of Patent: May 9, 2023

(54) SYSTEMS AND METHODS FOR AUTOMATED ANALYSIS OF MEDICAL IMAGES

(71) Applicant: Annalise-AI Pty Ltd, Sydney (AU)

(72) Inventors: Dang-Dinh-Ang Tran, Sydney (AU); Jarrel Seah, Sydney (AU); David Huang, Sydney (AU); David Vuong, Sydney (AU); Xavier Holt, Sydney (AU); Marc Justin Nothrop, Sydney (AU); Benjamin Austin, Sydney (AU); Aaron Lee, Sydney (AU); Marco Amoroso, Sydney (AU)

(73) Assignee: Annalise AI Pty Ltd, Sydney (AU)

( * ) Notice: Subject to any disclaimer, the term of this patent is extended or adjusted under 35 U.S.C. 154(b) by 0 days.

(21) Appl. No.: 17/616,538

(22) PCT Filed: Jun. 9, 2021

(86) PCT No.: PCT/AU2021/050580
§ 371 (c)(1),
(2) Date: Dec. 3, 2021

(87) PCT Pub. No.: WO2021/248187
PCT Pub. Date: Dec. 16, 2021

(65) Prior Publication Data
US 2023/0089026 A1 Mar. 23, 2023

(30) Foreign Application Priority Data

Jun. 9, 2020 (AU) .................................. 2020901881
Aug. 27, 2020 (AU) .................................. 2020903056
(Continued)

(51) Int. Cl.
*G16H 50/20* (2018.01)
*G16H 30/40* (2018.01)
(Continued)

(52) U.S. Cl.
CPC ........... *G16H 50/20* (2018.01); *A61B 6/5217* (2013.01); *G06V 10/82* (2022.01); *G16H 30/40* (2018.01); *G16H 40/67* (2018.01)

(58) Field of Classification Search
CPC ........ G16H 50/20; G16H 40/67; G16H 30/40; G06V 10/82; A61B 6/5217
(Continued)

(56) References Cited

U.S. PATENT DOCUMENTS 9,545,238 B2 * 1/2017 Bertsch ................ A61B 6/5217
10,949,968 B2 * 3/2021 Brestel ................... G16H 50/20
(Continued)

FOREIGN PATENT DOCUMENTS

JP 2019-209130 A 12/2019
KR 10-1980955 B1 5/2019

*Primary Examiner* — Michael Tomaszewski
(74) *Attorney, Agent, or Firm* — Muncy, Geissler, Olds & Lowe, P.C.

(57) ABSTRACT

This disclosure relates to detecting visual findings in anatomical images. Methods comprise inputting anatomical images into a neural network to output a feature vector and computing an indication of visual findings being present in the images by a dense layer of the neural network that takes as input the feature vector and outputs an indication of whether each of the visual findings is present in the anatomical images. The neural network is trained on a training dataset including anatomical images, and labels associated with the anatomical images and each of the visual findings. The visual findings may be organised as a hierarchical ontology tree. The neural network may be trained by evaluating the performance of neural networks in detecting the visual findings and a negation pair class which comprises anatomical images where a first visual finding is identified in the absence of a second visual finding.

24 Claims, 17 Drawing Sheets

(30) Foreign Application Priority Data

Sep. 22, 2020 (AU) ................................ 2020903405
Feb. 12, 2021 (AU) ................................ 2021900349

(51) Int. Cl.
*A61B 6/00* (2006.01)
*G06V 10/82* (2022.01)
*G16H 40/67* (2018.01)

(58) Field of Classification Search
USPC ......................................................... 705/2–3
See application file for complete search history.

(56) References Cited

U.S. PATENT DOCUMENTS

| | | | |
|---|---|---|---|
| 2018/0137621 A1* | 5/2018 | Stick | .......................... G06T 7/11 |
| 2018/0276817 A1 | 9/2018 | Isgum et al. | |
| 2019/0332898 A1 | 10/2019 | Saruta | |
| 2019/0340752 A1* | 11/2019 | Brestel | ................... G16H 30/40 |
| 2019/0340753 A1* | 11/2019 | Brestel | ................... G16H 15/00 |
| 2019/0340763 A1* | 11/2019 | Laserson | ............. G06F 18/2321 |
| 2019/0374165 A1 | 12/2019 | Poole et al. | |
| 2020/0085394 A1 | 3/2020 | Turcea et al. | |

\* cited by examiner

SYSTEMS AND METHODS FOR AUTOMATED ANALYSIS OF MEDICAL IMAGES

CROSS-REFERENCE TO RELATED APPLICATIONS

This application is a National Stage of International Application No. PCT/AU2021/050580, which claims priority from Australian provisional application numbers 2020901881 (filed on 9 Jun. 2020), 2020903056 (filed on 27 Aug. 2020), 2020903405 (filed on 22 Sep. 2020), and 2021900349 (filed on 12 Feb. 2021), the contents of which are incorporated herein in their entirety.

FIELD OF THE INVENTION

The present invention relates to computer-implemented methods for analysing medical images, as well as computing systems, services, and devices implementing the methods. Embodiments of the invention provide for automated analysis of medical images by employing machine learning techniques, in particular deep learning networks, such as convolutional neural networks, trained using sub-stratification training. Embodiments of the invention further improve automated analysis of medical images by providing the results of analysis of medical images in a consistent an easily interpretable manner. Embodiments of the invention further improve automated analysis of medical images by providing the results of analysis of medical images in an efficient and fast manner. Embodiments of the invention further improve automated analysis of medical images by employing a modified loss function for training neural networks to predict medical findings involving cardiothoracic ratio. Methods, systems, services, and devices embodying the invention find applications in the clinical assessment of chest conditions such as pneumothorax and other radiological findings pertaining to the chest.

BACKGROUND TO THE INVENTION

Generally, the manual interpretation of medical images performed by trained experts (such as e.g. radiologists) is a challenging task, due to the large number of possible findings that may be found. For example, the chest x-ray (CXR) is a very commonly performed radiological examination for screening and diagnosis of many cardiac and pulmonary diseases. CXRs are used for acute triage as well as longitudinal surveillance. In other words, a CXR is typically examined for any detectable abnormality in addition to the clinical indication for which it was ordered. This means that radiologists must be alert to identify many different conditions, with a concordant risk that some findings may be missed. CXRs are particularly difficult to interpret (see e.g. Robinson, P. J., Wilson, D., Coral, A., Murphy, A., Verow, P., 'Variation between experienced observers in the interpretation of accident and emergency radiographs,' *The British Journal of Radiology*, 72(856), April 1999, pp. 323-30). Additionally, the increasing demand for specialists that are qualified to interpret medical images (i.e. medical imaging specialists or expert radiologists) far outweighs the availability of these specialists. Furthermore, the training of new specialists requires a significant amount of time. As a result, technical operators, such as radiographic technicians/radiographers, are increasingly called upon to provide preliminary interpretations to decrease the waiting time and/or to provide a triage assessment. However, the accuracy and confidence in the work of such technicians is generally inferior to that of highly-trained specialists. Even among specialists, clinically substantial errors are common for certain findings. The likelihood for major diagnostic errors has been found to correlate with shift length and amount of work (number of interpretations) made by each expert (see e.g. Hanna, T. N., Lamoureux, C., Krupinski, E. A., Weber, S., Johnson, J. O., 'Effect of Shift, Schedule, and Volume on Interpretive Accuracy: A Retrospective Analysis of 2.9 Million Radiologic Examinations,' *Radiology*, November 2017, 170555).

Empirical training has been used to assess medical imagery, in which mathematical models are generated by learning a dataset. Deep learning is a particularly data-hungry subset of empirical training that is itself a subset of artificial intelligence (AI). Recently the use of deep learning approaches to generate deep neural networks (DNNs) which are also known as deep learning models, that automate the assessment of CXR images has been suggested (see e.g.: Laserson, J., Lantsman, C. D., Cohen-Sfady, M., Tamir, I., Goz, E., Brestel, C., Bar, S., Atar, M., and Elnekave, E., *TextRay: Mining Clinical Reports to Gain a Broad Understanding of Chest X-Rays*, arXiv:1806.02121, [cs.CV], 2018; and Majkowska, A., Mittal, S., Steiner, D., Reicher, J., McKinney, S., Duggan, G., Eswaran, K., Chen, P., Liu, Y., Kalidindi, S., Ding, A., Corrado, G., Tse, D., and Shetty, S., 'Chest Radiograph Interpretation with Deep Learning Models: Assessment with Radiologist-adjudicated Reference Standards and Population-adjusted Evaluation,' *Radiology*, 2020, 294:421-431).

In particular, Laserson et al. report the use of a deep learning model trained to predict a set of 40 findings given a patient's frontal and lateral scans, where the labels for the training dataset were obtained from hand-crafted regular expressions to define a search pattern for particular strings of text over radiological reports, then manually reviewed by expert radiologists. The accuracy of this approach using regular expression to obtain 'free' labels from text-based radiological reports is extremely limited for rare conditions, and also limited for conditions that frequently co-exist with other, more easily detectable, conditions which can confuse the findings due to positive linear associations. Furthermore, Majkowska et al. have shown that artefacts in imaging data, such as the presence of a chest tube in CXR images, can cause clinically meaningful failures.

There is, accordingly, an ongoing need for improved computational methods, systems, services, and devices to automatically analyse anatomical images. Furthermore, there is a need for improved methods of training deep learning models to predict the presence of a wide range of clinical findings more effectively, including infrequent conditions for which the volume of training data may be limited. It would also be desirable to provide methods of evaluating the performance of a model during training, e.g. via design of loss functions, that are able to account effectively for particular characteristics of specific clinical findings.

A further challenge is that predictions generated by deep learning models can be difficult to interpret by a user (such as, e.g., a clinician). Such models typically produce a score, probability or combination of scores for each class that they are trained to distinguish, which are often meaningful within a particular context related to the sensitivity/specificity of the deep learning model in detecting the clinically relevant feature associated with the class. Therefore, the meaning of each prediction must be evaluated in its specific context. This is especially problematic where deep learning models are used to detect a plurality of clinically relevant features, as a different specific context would have to be presented and understood by the user for each of the plurality clinical features. Prior methods have in their most basic form simply indicated yes or no for the presence of a radiological finding among a list of findings without re-ordering to indicate clinical significance, no grouping to indicate priority of clinical significance, and no context on confidence, specificity and sensitivity of the prediction generated by an AI model.

Accordingly, there is also an ongoing need for automated analysis systems to communicate the statistical results of deep learning models more effectively to a user in a simple and intuitive manner that imposes lower cognitive load on the user, thereby enabling the user to make an informed clinical decision.

Computational methods for providing automated analysis of anatomical images may be provided in the form of an online service, e.g. implemented in a cloud computing environment. This enables the computational resources required for analysis to be provided and managed in a flexible manner, and reduces the requirement for additional computing power to be made available on-premises (e.g. in hospitals, radiology service providers, and other clinical environments). This approach also enables analysis services to be made available in low-resource environments, such as developing countries. However, in the presence of bandwidth constraints (e.g. in developing countries and/or remote locations with poor Internet bandwidth, or is cases where there is a high volume of images such as radiology scans), returning processed data to the user in a timely manner may be challenging. This is particularly crucial in situations where the user must wait for data to be retrieved in real-time, e.g. when reviewing a study at an on-premises workstation. The user experiencing such delay or seeing flickering on the screen because the image is being retrieved as they are attempting to view it can represent a significant barrier to adoption of automated solutions for medical image analysis. Further, such issues can undermine the benefits of automated medical image analysis, as they can reduce the amount of expert time that is saved by performing some of the analysis in an automated fashion.

Therefore, there is also an ongoing need for improved methods for communicating the results of medical image analysis to a user in a manner that efficiently produces clinically useful outputs for clinical decision support.

In various embodiments the present invention seeks to address, individually and/or in combination, one or more of the foregoing needs and limitations of the prior art.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect, there is provided a computer implemented method for detecting a plurality of visual findings in one or more anatomical images of a subject, comprising:

providing one or more anatomical images of the subject;
inputting the one or more anatomical images into a convolutional neural network (CNN) component of a neural network to output a feature vector;
computing an indication of a plurality of visual findings being present in at least one of the one or more anatomical images by a dense layer of the neural network that takes as input the feature vector and outputs an indication of whether each of the plurality of visual findings is present in at least one of the one or more anatomical images,
wherein the neural network is trained on a training dataset including, for each of a plurality of subjects, one or more anatomical images, and a plurality of labels associated with the one or more anatomical images and each of the respective visual findings, wherein the neural network is trained by evaluating performance of a plurality of neural networks in detecting the plurality of visual findings, wherein the performance evaluation comprises accounting for correlation between one or more pairs of the plurality of visual findings.

In embodiments of the invention, the visual findings may be radiological findings in anatomical images comprising one or more chest x-ray (CXR) images.

Advantageously, embodiments of the invention may employ a deep learning model trained to detect/classify pneumothoraces from a CXR image. Two types of pneumothorax, namely simple and tension, may be detected by such embodiments. The training of the deep learning model for each of these two types of pneumothoraces may be in combination with a plurality of other radiological findings, e.g. 186 radiological findings. For every chest x-ray image, in one example, the inventors obtained labels for each of the 188 findings (e.g. 186 other findings plus two pneumothorax findings), enabling them to prevent a deep learning model from learning incorrect data correlations. This advantageously enables the deep learning model to be trained to find the combination of findings, for example: tension_pneumothorax+aerodigestive_tubes; or simple_pneumothorax+acute_clavicle_fracture. Additionally, the deep learning model may be trained to detect negative pairs, where a radiological finding (such as pneumothorax) is detected in the absence of another radiological finding (such as an intercostal drain), where these pair of findings have a statistically significant correlation between them.

A comprehensive deep learning model for CXR images embodying the invention advantageously addresses common medical mistakes made by clinicians such as detecting correct positioning of a nasogastric tube, detecting Pulmonary Nodule, Pulmonary Mass, and Bone Lesions as possible cancer. Another advantage is that the system is more likely to be used if it can detect and classify a broad range of radiological findings for a CXR image rather than only one or two radiological findings.

Additional stratification of radiological findings in terms of pairs of radiological findings, in accordance with embodiments of the invention, addresses a major shortfall of prior art approaches. For example, an empirical model (e.g. a deep learning model) that functions as a pneumothorax detector that only works if the patient is already treated (i.e. a tube has already been put in) will be utterly useless. This is because such an inferior model will only ever detect pneumothorax that is already known about (because the medical practitioner has already put the tube into the patient). This inferior model would fail and neglect to detect pneumothorax if no tube is present in the CXR image. For a clinician/radiologist user, they care about sub-classes because they want to know that the model works in cases where they could potentially have missed it. For example, if a deep learning model is only trained to detect pneumothoraces regardless of any other radiological finding, it may in fact be detecting the presence of a different radiological finding (such as the presence of a chest tube) that happens to highly correlate with the presence of a pneumothorax in the training dataset rather than the pneumothorax itself.

Embodiments of the present invention are advantageously more robust and reliable than other empirical models, specifically, deep learning models, in detecting pneumothorax and other radiological findings in CXR images. Deep learning models embodying the invention may therefore be more clinically effective than others.

The performance evaluation process may take into account the correlation between one or more pairs of the plurality of visual findings by evaluating the performance of each of the plurality of neural networks using a testing dataset that comprises a subset of the training dataset, where the testing dataset is selected such that the correlation between the one or more pairs of the plurality of findings in the testing dataset satisfies one or more criteria selected from: the correlation between the one or more pairs of the plurality of findings in the validation dataset does not differ by more than a predetermined percentage from the corresponding correlation in the full training dataset; and the correlation between the one or more pairs of the plurality of findings in the validation dataset does not exceed a predetermined threshold. The predetermined percentage may be about 10%, about 15%, about 20% or about 25%, preferably about 20%. The predetermined threshold may be about 0.7, about 0.75, about 0.8, about 0.85 or about 0.9, preferably about 0.8.

Instead of, or in addition to, the above, the performance evaluation process may take into account the correlation between one or more pairs of the plurality of visual findings by evaluating the performance of each of the plurality of neural networks for each of the plurality of visual findings and at least one negation pair class which comprises CXR images where a first one of the plurality of visual findings is identified in the absence of a second one of the plurality of visual findings. The first and second visual findings may be significantly correlated in the training dataset. In embodiments, evaluating the performance of the neural network for each of the plurality of visual findings and at least one negation pair class comprises computing a combined (e.g. average) performance across the plurality of visual findings and the at least one negation pair class.

The at least one negation pair may be selected from: ('pneumothorax', 'subcutaneous_emphysema'), ('pneumothorax', 'intercostal_drain'), ('pneumothorax', 'tracheal_deviation'), ('pleural_effusion', 'intercostal_drain'), ('pleural_effusion', 'cardiomegaly'), ('significant_collapse', 'ett'), ('significant_collapse', 'diaphragmatic_elevation'), ('significant_collapse', 'tracheal_deviation'), ('significant_collapse', 'linear atelectasis'), ('interstitial_thickening_volloss', 'linear atelectasis'), ('interstitial_thickening_volloss_lower', 'linear atelectasis'), ('interstitial_thickening_volloss_upper', 'interstitial_thickening_upper'), ('cavitating_mass', 'cavitating_mass_internal_content'), ('pneumomediastinum', 'subcutaneous_emphysema'), ('dish', 'spine_arthritis'), ('shoulder_dislocation', 'acute_humerus_fracture'), ('shoulder_dislocation', 'chronic_humerus_fracture'), ('rib_lesion', 'humeral_lesion'), ('rib_lesion', 'clavicle_lesion'), ('rib_lesion', 'scapular_lesion'), ('rib_lesion', 'spine_lesion'), ('clavicle_lesion', 'spine_lesion'), ('scapular_lesion', 'spine_lesion'), ('rib_resection', 'lung_sutures'), ('acute_humerus_fracture', 'chronic_humerus_fracture'), ('lung_lesion', 'surgical_clip'), ('lung_sutures'), ('lung_lesion', 'lung_resection_volloss'), ('bullae', 'hyperinflation'), ('bullae', 'hyperlucency'), ('cardiomegaly', 'electronic_cardiac_devices'), ('cardiomegaly', 'cardiac_valve_prosthesis'), ('cardiomegaly', 'pulmonary_congestion'), ('cardiomegaly', 'sternotomy_wires'), ('cardiomegaly', 'airspace_opacity_without_focus'), ('cardiomegaly', 'interstitial_thickening_no_volloss'), ('acute_aortic_syndrome', 'tracheal_deviation'), ('aortic_arch_calcification', 'coronary_stent'), ('distended_bowel', 'subdiaphragmatic_gas'), ('airspace_opacity', 'pleural_effusion'), ('airspace_opacity', 'loculated_effusion'), ('ett', 'ngt'), ('ett', 'cvc'), ('ett', 'pac'), ('ett', 'intercostal_drain'), ('ngt', 'cvc'), ('ngt', 'pac'), ('ngt', 'intercostal_drain'), ('cvc', 'pac'), ('cvc', 'intercostal_drain'), ('pac', 'intercostal_drain'), ('kyphosis', 'scoliosis'), ('osteopaenia', 'spine_wedge_fracture'), and ('mastectomy', 'axillary_clips').

The neural network may be trained by evaluating the performance of a plurality of neural networks in detecting the plurality of visual findings and selecting one or more best performing neural networks.

The one or more CXR images may comprise at least two anatomical images. Preferably, at least two of the CXR images are captured at a different orientation of the body portion of the subject. In embodiments, the method comprises: inputting a first CXR image of the at least two of the CXR images into a first CNN component of the neural network to output a first feature vector, inputting a second CXR image of the at least two of the CXR images into a second CNN component of the neural network to output a second feature vector; and inputting a feature vector that combines, such as e.g. concatenates, the first feature vector and the second feature vector into the dense layer of the neural network. The first and second CNN components may be the same or different.

The one or more CXR images may comprise three CXR images, where at least two of the CXR images are captured at a different orientation of the body portion of the subject. In such cases, the method may comprise: inputting a third CXR image of the at least two of the CXR images into a third CNN component of the neural network to output a third feature vector; and inputting a feature vector that combines, such as e.g. concatenates, the first feature vector, the second feature vector and the third feature vector into the dense layer of the neural network. The first, second and third CNN components may be the same or different.

The at least two different orientations of the body portion of the subject may correspond to non-parallel viewing planes of the subject, such as lateral and frontal viewing planes. The one or more CXR images may comprise at least one image that is captured by an imaging device when the subject is oriented anterior-posterior (AP) or poster-anterior (PA) relative to the imaging device. The CXR images may comprise at least one image that is captured by an imaging device when the subject is oriented anterior-posterior (AP) or posterior-anterior (PA) relative to the imaging device and at least one image that is captured by an imaging device when the subject is oriented laterally relative to the imaging device. The CXR images may comprise at least one image that is captured by an imaging device when the subject is oriented anterior-posterior (AP) relative to the imaging device, at least one image that is captured by an imaging device when the subject is oriented poster-anterior (PA) relative to the imaging device, and at least one image that is captured by an imaging device when the subject is oriented laterally relative to the imaging device.

In embodiments, the method further comprises inputting the one or more CXR images into a convolutional neural network (CNN) component of a second neural network to output a feature vector; and computing an indication of the likely orientation of each of the one or more CXR images by a dense layer of the second neural network that takes as input the feature vector and outputs an indication of whether the one or more CXR images belongs to one or more of a plurality of classes associated with different orientations of the subject. Where the first, second and optionally third CNN components of the first neural network are different, a CXR image may be input into the first, second or optionally third CNN component depending on the likely orientation determined by the second neural network.

The plurality of visual findings may include at least 80, at least 100 or at least 150 visual findings. The plurality of visual findings may include at least 80, at least 100 or at least 150 visual findings selected from Table 1 or Table 2.

The plurality of visual findings is preferably organised as a hierarchical ontology tree. The hierarchical ontology tree may include at least 50, at least 80, at least 100 or at least 150 terminal leaves. The neural network may output an indication of whether each of the plurality of visual findings is present in one or more of the CXR images of the subject, the plurality of visual findings including all terminal leaves and internal nodes of the hierarchical ontology tree. In other words, the neural network may output a prediction for each of the plurality of visual findings, which include both internal nodes and terminal leaves in the hierarchical ontology tree.

The plurality of labels associated with at least a subset of the one or more CXR images and each of the respective visual findings in the training dataset may be derived from the results of review of the one or more anatomical images by at least one expert. The plurality of labels for the subset of the CXR images in the training dataset are advantageously derived from the results of review of the one or more CXR images by at least two experts, preferably at least three or exactly three experts.

The plurality of labels for the subset of the CXR images in the training dataset may be obtained by combining the results of review of the one or more anatomical images by a plurality of experts.

The plurality of labels associated with at least a subset of the one or more CXR images and each of the respective visual findings in the training dataset may be derived from labelling using a plurality of labels organised as a hierarchical ontology tree. Preferably, at least one of the plurality of labels is associated with a terminal leaf in the hierarchical ontology tree, and at least one of the plurality of labels is associated with an internal node in the hierarchical ontology tree. As a result of the hierarchical structure, some of the plurality of labels will contain partially redundant information due to propagation of the label from a lower level to a higher (internal node) level. This may advantageously increase the accuracy of the prediction due to the model training benefitting both from high granularity of the findings in the training data as well as high confidence training data for findings at lower granularity levels.

In embodiments, the plurality of labels associated with the one or more CXR images in the training dataset represent a probability of each of the respective visual findings being present in the at least one of the one or more CXR images of a subject.

Labelling using a plurality of labels organised as a hierarchical ontology tree may be obtained through expert review as explained above. For example, a plurality of labels associated with at least a subset of the one or more chest x-ray images and each of the respective visual findings in the training dataset may be derived from the results of review of the one or more anatomical images by at least one expert using a labelling tool that allows the expert to select labels presented in a hierarchical object (such as e.g. a hierarchical menu). Using such tools, an expert may be able to select a visual finding as a terminal leaf of the hierarchical object, and the tool may propagate the selection through the hierarchy such that higher levels of the hierarchy (internal nodes) under which the selected label is located are also selected.

In embodiments, the indication of whether each of the plurality of visual findings is present in at least one of the one or more CXR images represents a probability of the respective visual finding being present in at least one of the one or more CXR images.

In embodiments, the plurality of labels associated with at least a further subset of the one or more CXR images and each of the respective visual findings in the training dataset are derived from an indication of the plurality of visual findings being present in at least one of the one or more CXR images obtained using a previously trained neural network.

In embodiments, the method further comprises computing a segmentation mask indicating a localisation for at least one of the plurality of visual findings by a decoder that takes as input the feature vector and outputs an indication of where the visual finding is present in the one or more CXR images. In embodiments, the decoder is the expansive path of a U-net where the contracting path is provided by the CNN component that outputs the feature vector.

In embodiments, the neural network is trained by evaluating the performance of a plurality of neural networks (the plurality of neural networks being trained from a labelled dataset generated via consensus of radiologists) in detecting the plurality of visual findings and in detecting the localisation of any of the plurality of visual findings that are predicted to be present.

In embodiments, the CNN component is an EfficientNet. In embodiments, Global Average Pooling and/or Global Max Pooling layers are added to the top-level activation feature map from the EfficientNet and the outputs are pooled and concatenated resulting in an output tensor that is provided to the dense layer.

In embodiments, the neural network takes as input a plurality of CXR images (such as e.g. 1, 2, 3, 4 or more) and produces as output an indication of a plurality of visual findings being present in any one of the plurality of images.

According to a second aspect, there is provided a computer-implemented method for detecting a plurality of visual findings in one or more anatomical images of a subject, comprising:

providing one or more anatomical images of a subject;
inputting the one or more anatomical images into a convolutional neural network (CNN) component of a neural network to output a feature vector;
computing an indication of a plurality of visual findings being present in at least one of the one or more anatomical images by a dense layer of the neural network that takes as input the feature vector and outputs an indication of whether each of the plurality of visual findings is present in at least one of the one or more anatomical images, wherein the neural network is trained on a training dataset including, for each of a plurality of subjects, one or more anatomical images, and a plurality of labels associated with the one or more anatomical images and each of the respective visual findings, wherein the plurality of visual findings is organised as a hierarchical ontology tree and the training comprises evaluating performance of the neural network at different levels of the hierarchy of the ontology tree.

The hierarchical ontology tree may comprise internal nodes and terminal leaves, and the neural network may output an indication of whether each of the plurality of visual findings is present in at least one of the one or more anatomical images, for visual findings that include internal nodes and terminal leaves.

In embodiments, the neural network is trained by evaluating the performance of a plurality of neural networks in detecting the plurality of visual findings, wherein the performance evaluation process takes into account the correlation between one or more pairs of the plurality of visual findings.

In embodiments, the plurality of labels associated with the one or more anatomical images and each of the respective visual findings is generated via consensus of imaging specialists. The visual findings may be radiological findings in anatomical images comprising one or more CXR images, and the imaging specialists may be radiologists.

The computer-implemented method of the second aspect may further comprise any of the additional features described in relation to the first aspect.

According to a third aspect, there is provided a computer implemented method for detecting a plurality of visual findings in one or more anatomical images of a subject, comprising:
  providing one or more anatomical images of a subject;
  inputting the one or more anatomical images into a convolutional neural network (CNN) component of a neural network to output a feature vector;
  computing an indication of a plurality of visual findings being present in at least one of the one or more anatomical images by a dense layer of the neural network that takes as input the feature vector and outputs an indication of whether each of the plurality of visual findings is present in at least one of the one or more anatomical images,
  wherein the neural network is trained on a training dataset including, for each of a plurality of subjects, one or more anatomical images, and a plurality of labels associated with the one or more anatomical images and each of the respective visual findings, wherein the plurality of visual findings is organised as a hierarchical ontology tree, and
  wherein the neural network is trained by evaluating the performance of a plurality of neural networks in detecting the plurality of visual findings and at least one negation pair class which comprises anatomical images where a first one of the plurality of visual findings is identified in the absence of a second one of the plurality of visual findings.

The visual findings may be radiological findings in anatomical images comprising one or more CXR images.

The computer-implemented method of the third aspect may further comprise any of the additional features described in relation to the first aspect.

According to a fourth aspect, there is provided a computer-implemented method for training a neural network to detect a plurality of visual findings in one or more anatomical images of a subject, comprising:
  providing a neural network comprising a first convolutional neural network (CNN) component that takes as input one or more anatomical images of a subject and outputs a first feature vector, and a dense layer that takes as input a feature vector comprising the first feature vector and outputs an indication of whether each of the plurality of visual findings is present in at least one of the one or more anatomical images;
  retrieving, from a data store, a training dataset including, for each of a plurality of subjects, one or more anatomical images, and a plurality of labels associated with the one or more anatomical images and each of the respective visual findings; and
  training the neural network using the training dataset,
  wherein the training comprises evaluating performance of the neural network in detecting the plurality of visual findings relative to one or more similar neural networks, wherein the performance evaluation comprises accounting for correlation between one or more pairs of the plurality of visual findings.

In embodiments, the neural network further comprises a decoder that takes as input the first feature vector and outputs a segmentation mask indicating a localisation for at least one of the plurality of visual findings.

The visual findings may be radiological findings in anatomical images comprising one or more CXR images.

The computer-implemented method of the fourth aspect may further comprise any of the additional features described in relation to the first aspect.

According to a fifth aspect, there is provided a computer-implemented method for training a neural network to detect a plurality of visual findings in one or more anatomical images of a subject, comprising:
  providing a neural network comprising a first convolutional neural network (CNN) component that takes as input one or more anatomical images of a subject and outputs a first feature vector, and a dense layer that takes as input a feature vector comprising the first feature vector and outputs an indication of whether each of the plurality of visual findings is present in at least one of the one or more anatomical images;
  retrieving, from a data store, a training dataset including, for each of a plurality of subjects, one or more anatomical images, and a plurality of labels associated with the one or more anatomical images and each of the respective visual findings; and
  training the neural network using the training dataset,
  wherein the plurality of visual findings is organised as a hierarchical ontology tree, and the training comprises evaluating performance of the neural network at different levels of the hierarchy of the ontology tree.

The hierarchical ontology tree may comprise internal nodes and terminal leaves, and the neural network may output an indication of whether each of the plurality of visual findings is present in at least one of the one or more anatomical images, for visual findings that include internal nodes and terminal leaves.

In embodiments, the neural network is trained by evaluating the performance of a plurality of neural networks in detecting the plurality of visual findings, wherein the performance evaluation process takes into account the correlation between one or more pairs of the plurality of visual findings.

In embodiments, the plurality of labels associated with the one or more anatomical images and each of the respective visual findings is generated via consensus of imaging specialists. The visual findings may be radiological findings in anatomical images comprising one or more CXR images, and the imaging specialists may be radiologists.

The computer-implemented method of the fifth aspect may further comprise any of the additional features described in relation to the first aspect.

According to a sixth aspect, there is provided a computer-implemented method for training a neural network to detect a plurality of visual findings in one or more anatomical images of a subject, comprising:
providing a neural network comprising a first convolutional neural network (CNN) component that takes as input one or more anatomical images of a subject and outputs a first feature vector, and a dense layer that takes as input a feature vector comprising the first feature vector and outputs an indication of whether each of the plurality of visual findings is present in at least one of the one or more anatomical images;
retrieving, from a data store, a training dataset including, for each of a plurality of subjects, one or more anatomical images, and a plurality of labels associated with the one or more anatomical images and each of the respective visual findings; and
training the neural network using the training dataset,
wherein the plurality of visual findings is organised as a hierarchical ontology tree, and the training comprises evaluating performance of the neural network at different levels of the hierarchy of the ontology tree, and
wherein the training further comprises evaluating performance of the neural network in detecting the plurality of visual findings, and at least one negation pair class which comprises anatomical images where a first one of the plurality of visual findings is identified in the absence of a second one of the plurality of visual findings, relative to one or more similar neural networks.

The hierarchical ontology tree may comprise internal nodes and terminal leaves, and the neural network may output an indication of whether each of the plurality of visual findings is present in at least one of the one or more anatomical images, for visual findings that include internal nodes and terminal leaves.

In embodiments, the plurality of labels associated with the one or more anatomical images and each of the respective visual findings is generated via consensus of imaging specialists. The visual findings may be radiological findings in anatomical images comprising one or more CXR images, and the imaging specialists may be radiologists.

The computer-implemented method of the sixth aspect may further comprise any of the additional features described in relation to the first aspect.

According to a seventh aspect, there is provided a method comprising:
receiving a first value that provides an indication of whether a first visual finding is present in at least one of one or more anatomical images of a subject, wherein the first value is an output generated by a predictive model trained to detect at least the first visual finding in anatomical images;
receiving one or more parameters associated with the first value, the parameters comprising at least a finding-dependent threshold value to which the first value is to be compared;
computing a transformed first value from the first value according to a transformation whereby the finding-dependent threshold value is mapped to a predetermined finding-independent fixed threshold value and a comparative relationship between the transformed first value and the fixed threshold value is maintained relative to a corresponding comparative relationship between the first value and the finding-dependent threshold value; and
displaying at least the transformed first value to a user In embodiments the predetermined fixed threshold may also be displayed to the user.

As a result, the transformed first value is comparable to the predetermined fixed threshold. As such, the comparison between the first value and its respective threshold can be displayed in a similar way for each of a plurality of values and their respective thresholds, thereby making the results of the deep learning model quickly and easily interpretable by the user.

The first value may be an indication of whether the first visual finding is present in one or more anatomical images computed using a method according to any one or more embodiments of the first, second or third aspect.

In embodiments, the transformation may be defined according to the formula:

$$TV = FT\left(1 + \frac{(V-T)}{(1-T)}\right) \quad (1)$$

where TV is the transformed first value, V is the first value, T is the finding-dependent threshold to which the first value is to be compared, and FT is the predetermined finding-independent fixed threshold.

Advantageously, embodiments are thereby able to transform a numerical statistical output generated by a predictive model, e.g. a deep leaning model, such that they are communicated to a user in a manner where the relationship between a prediction for a radiological finding among a plurality of radiological findings (potentially in excess of 100 findings) and its context is consistent. This may beneficially contribute to realising the full potential of such models, because the highly detailed output generated by the models can be efficiently communicated, preferably visually, to a user (e.g. a clinician) of the diagnostic information provided by the models in order for fast decision making without a high cognitive load being imposed upon the clinician.

For example, the first value V may be a score between 0.0 and 1.0, as is commonly the case with predictive models using, e.g., a softmax output layer, wherein values closer to 1.0 are indicative of the presence of the first visual finding and values closer to 0.0 are indicative of the unlikely—or inconclusive—presence of the first visual finding. A threshold T may be set between these values to indicating a decision point between unlikely presence and likely presence. The setting of this threshold may depend upon the specific visual finding, and may be 'tuned', e.g. according to a tolerance for false positives relative to false negatives. Despite the variability of the threshold T between different visual findings, the predetermined fixed threshold FT can be conveniently chosen as ½. As such, a transformed first value above ½ always corresponds to an indication that the visual finding is likely to be present (i.e. the first value is above its respective threshold) and a transformed first value below ½ always corresponds to an indication that the visual finding is not likely to be present (i.e. the first value is below its respective threshold).

In embodiments, the method further comprises:
receiving one or more second values quantifying a confidence associated with the first value;
computing corresponding transformed second values according to a transformation whereby a comparative relationship between the transformed second values and the transformed first value is maintained relative to a corresponding comparative relationship between the first value and the second values; and
displaying to a user the transformed second values so as to provide a visual indication of confidence associated with the first value.

In some embodiments, the second values may be provided in absolute reference to the first value (e.g. the boundaries of a confidence interval around the first value, etc.), and the transformed second values may be computed according to the same transformation, e.g. equation (1). In such embodiments, the transformed second value is preferably displayed.

In alternative embodiments, the second values may be provided in relative reference to the first value (e.g. a distance between the first value and the boundaries of a confidence interval, a standard deviation, a standard error of the mean, etc.), and the transformed second values may be computed according to the formula:

$$TV_{\delta v} = FT \frac{\delta v}{1-T} \quad (2)$$

where $TV_{67\ v}$ is the transformed second value, and $\delta v$ is the second value provided in relative reference to the first value. In such embodiments, values obtained by adding and subtracting the transformed second values to/from the transformed first value are preferably displayed.

In embodiments, the first value is a value between 0.0 and 1.0. In embodiments, the first value is a predicted probability of the first visual finding being present in at least one of the one or more anatomical images.

In embodiments, the first value is an average of a plurality of first values output by each of an ensemble of deep learning models trained to detect at least the first visual finding in anatomical images.

The one or more second values may comprise: a standard deviation; a standard error of the mean; a first boundary of a confidence interval and/or a second boundary of a confidence interval; or a distance between the first value and a first and/or second boundary of a confidence interval.

A confidence interval is preferably a 95% confidence interval. Displaying a confidence interval to the user advantageously enables the user to compare the first value to its threshold in the context of the confidence with which the first value is predicted.

A standard deviation of standard error of the mean may be obtained based on a plurality of first values output by each of an ensemble of deep learning models trained to detect at least the first visual finding in anatomical images.

A distance between the first value and the first/second boundary of a confidence interval may advantageously be provided as sem*c, where sem is the standard error of the mean of a set of first values, and c is a constant that depends on the choice of confidence interval. For example, where the confidence interval is a 95% confidence interval, c may be chosen as approximately 1.96.

A first boundary of a confidence interval may be obtained as mean_score−sem*c, where mean_score is the mean of a plurality of first values output by each of an ensemble of deep learning models trained to detect at least the first visual finding in anatomical images.

A second boundary of a confidence interval may be obtained as mean_score+sem*c, where mean_score is the mean of a plurality of first values output by each of an ensemble of deep learning models trained to detect at least the first visual finding in anatomical images.

Displaying the transformed first value to a user may comprise displaying a scale that captures the possible range of the first value and indicating the transformed first value on the scale. The scale may be a linear scale.

In embodiments, displaying a scale comprises displaying a bounded area with the indications 'present' and 'absent' at the respective ends of the bounded area.

The scale may be displayed as a rectangular box. The transformed first value may be displayed by distinguishing at least a first section and a second section of the box, the first section corresponding to the possible range below the transformed first value and the second section corresponding to the range above the transformed first value.

The scale may be displayed as a box comprising a first section corresponding to the possible range below the transformed first value and a second section corresponding to the range above the transformed first value, wherein one of the first section of the second section is further divided in two subsections corresponding to a range up to and above the predetermined fixed threshold, respectively.

In embodiments, the predetermined fixed threshold is equal to the mid-point of the possible range of the first value. For example, when the first value is a value between 0.0 and 1.0, the predetermined fixed threshold is preferably ½. As a result, the threshold to which the first value is to be compared will always correspond to the mid-point of the scale on which the first value is displayed. This makes it easy for a user to interpret the output of the deep learning model.

In embodiments, the threshold to which the first value is to be compared represents the value of the first value at which the deep learning model has a desired balance of recall and precision in detecting the first visual finding in anatomical images.

The value of the first value at which the deep learning model has a desired balance of recall and precision in detecting the first visual finding in anatomical images may be the value that maximises the $F_1$ or the $F_\beta$ score of the deep learning model for the detection of the first visual finding.

The recall and precision of a deep learning model in detecting the presence of a first visual finding may be assessed by computing the recall and precision of model prediction in a test data set where the presence or absence of the first visual finding is known.

In embodiments, the threshold to which the first value is to be compared is a default value. For example, a default value may be obtained as the $F_1$ score of the deep learning model for the detection of the first visual finding. In embodiments, the threshold to which the first value is to be compared is received from a user or obtained using an indication received from a user. For example, the threshold to which the first value is to be compared may be obtained as the $F_\beta$ score of the deep learning model for the detection of the first visual finding, where the value of $\beta$ is received from a user or obtained from an indication received from a user, such as e.g. an indication of the relative importance of false negatives and false positives.

The one or more transformed second values may be displayed as confidence bars around the transformed first value.

The method may be computer-implemented and the displaying may be performed through a user-interface.

In embodiments, the method further comprises repeating the method for one or more further first values, each of which provide(s) an indication of whether a respective further visual finding is present in at least one of one or more anatomical images of a subject, wherein each further first value is an output generated by a deep learning model trained to detect at least the further visual finding in anatomical images.

Advantageously, improved usability may be further facilitated by enabling the user to interact with the results of the deep learning models in an efficient manner by performing one or more of: selectively displaying a particular prediction of set or predictions associated with a particular, user-selected, radiological finding, selectively displaying a subset of the radiological findings for which a prediction is available, displaying a subset of the radiological findings as priority findings separately from the remaining of the radiological findings.

Accordingly, In embodiments the method further comprises displaying a list of visual findings comprising at least the first visual finding on a user interface, wherein the step of displaying the transformed first value, and optionally the predetermined fixed threshold and transformed second value(s) is triggered by a user selecting the first visual finding. In embodiments, the user selecting the first visual finding comprises the user placing a cursor displayed on the user interface over the first visual finding in the displayed list.

Within the context of the present disclosure, displaying a list of visual findings comprises displaying a plurality of text strings, each representing a radiological finding associated with a respective visual finding.

In embodiments, the method further comprises displaying a list of visual findings comprising at least the first visual finding on a user interface, wherein the visual findings are organised as a hierarchical ontology tree and the step of displaying the list of visual findings comprises displaying the visual findings that are at a single level of the hierarchical ontology tree, and displaying the children of a user-selected displayed visual finding, optionally wherein the user selecting a displayed visual finding comprises the user placing a cursor displayed on the user interface over the displayed visual finding in the displayed list.

The list of visual findings may comprise at least 100 visual findings. The selective displayed of subsets of visual findings organised as a hierarchical ontology tree enables the user to navigate through the results of deep learning analysis of anatomical images in an efficient manner.

The method may further comprise displaying a list of visual findings comprising at least the first visual finding on a user interface, wherein the list of visual findings is separated between at least a first sublist and a second sublist, wherein the first sublist comprises one or more visual findings that are priority findings, or an indication that there are no priority findings.

Advantageously, the selective display of particular subsets of visual findings in a 'priority findings' sub-list enables the user to quickly identify the image features that should be reviewed, thereby making the deep learning-aided analysis of the chest x-ray images more efficient. The set of visual findings included in the first sublist may be defined by default. Alternatively, one or more visual findings to be included in the first sublist and/or the second sublist may be received from a user.

The method may further comprise displaying a list of visual findings comprising at least the first visual finding on a user interface, wherein the list of visual findings is separated between a sublist comprising one or more visual findings that were detected in the anatomical images, and a sublist comprising one or more visual findings that were not detected in the anatomical images. The sublist comprising one or more visual findings that were detected in the anatomical images is separated between a first sublist and a second sublist, wherein the first sublist comprises one or more visual findings that are priority findings, or an indication that there are no priority findings.

The method may further comprise displaying at least one of the one or more anatomical images of the subject on a user interface, preferably a screen, and displaying a segmentation map overlaid on the displayed anatomical image(s) of the subject, wherein the segmentation map indicates the areas of the anatomical image(s) where the first visual finding has been detected, wherein the step of displaying the segmentation map is triggered by a user selecting the first visual finding in a displayed list of visual findings. The user selecting the first visual finding may comprise the user placing a cursor displayed on the user interface over the first visual finding in the displayed list.

The first value, the second value(s), and/or the segmentation map may be produced using a method according to any one or more embodiments of the first, second or third aspect.

An automated analysis of anatomical images using deep learning models may be improved by enabling the user to review the results of such automated analysis and provide feedback/corrective information in relation to a radiological finding that may have been missed by the automated analysis process, and using this information to train one or more improved deep learning model(s).

Accordingly, the method may further comprise displaying at least one of the one or more anatomical images of the subject and receiving a user selection of one or more areas of the anatomical image(s) and/or a user-provided indication of a first visual finding.

A user-provided indication of a first visual finding may be received by the user selecting a first visual finding from a displayed list of visual findings, or by the user typing or otherwise entering a first visual finding. Preferably, the method comprises receiving both a user selection of one or more areas of the anatomical image(s) and a user-provided indication of a first visual finding associated with the user-selected one or more areas.

Preferably, the method further comprises recording the user selected one or more areas of the anatomical image(s) and/or the user provided indication of the first visual finding in a memory, associated with the one or more anatomical image(s).

The method may further comprise using the user-selected one or more areas of the anatomical image(s) and/or the user-provided indication of the first visual finding to train a deep learning model to detect the presence of at least the first visual finding in anatomical images and/or to train a deep learning model to detect areas showing at least the first visual finding in anatomical images. The deep learning model trained to detect areas showing at least the first visual finding in anatomical images may be different from the deep learning model that trained to detect the presence of at least the first visual finding in anatomical images.

Using the user-selected one or more areas of the anatomical image(s) and/or the user-provided indication of the first visual finding to train a deep learning model to detect the presence of at least the first visual finding in anatomical images may comprise at least partially re-training the deep learning model that was used to produce the first value.

Using the user-selected one or more areas of the anatomical image(s) and/or the user-provided indication of the first visual finding to train a deep learning model to detect the areas showing at least the first visual finding in anatomical may comprise at least partially re-training the deep learning model that was used to produce a segmentation map indicating the areas of the anatomical image(s) where the first visual finding has been detected.

According to an eighth aspect, there is provided a method comprising:

receiving, by a processor, the results of a step of analysing one or more anatomical images of a subject using one or more deep learning models trained to detect at least a first visual finding in anatomical images, wherein the results comprise at least a first segmentation map indicating the areas of a respective anatomical image where the first visual finding has been detected; and communicating, by the processor, the result of the analysing step to a user by sending to a user device at least the first segmentation map and the respective anatomical image as separate image files, wherein the segmentation map image file has been compressed by the processor prior to sending, and wherein the segmentation map image file comprises information that can be displayed overlaid on the information in the respective anatomical image file.

Advantageously, in this aspect the results of a deep learning analysis are sent to a user in the form of a segmentation map image file that only contains the segmentation information and can be displayed overlaid on the respective anatomical image. This dramatically reduces the amount of data that must be provided to the user in order to communicate the results of the deep learning analysis, leading to a more efficient diagnosis process for the user. This process may be further facilitated by pre-fetching the results of the deep learning analysis prior to the user requesting said results. This is particularly advantageous where the pre-fetching is performed using knowledge of the user's current or likely attention to prioritise the results to be fetched.

Accordingly, the step of sending a segmentation map image file and the respective anatomical image file is advantageously performed automatically in the absence of a user requesting the display of the results of the step of detecting the first visual finding.

The processor compressing the segmentation map image file may comprise the processor applying a lossless compression algorithm. The processor compressing the segmentation map image file may comprise the processor rendering the segmentation map as a PNG file.

According to a further aspect, there is provided a method comprising:

receiving, by a processor of a user device, the results of a step of analysing one or more anatomical images of a subject using one or more deep learning models trained to detect at least a first visual finding in anatomical images, wherein receiving the results comprises receiving as separate files:
at least a first segmentation map image file indicating the areas of a respective anatomical image where the first visual finding has been detected, wherein the segmentation map image file is a compressed file; and
the respective anatomical image file; and displaying the information in the segmentation map image file overlaid on the information in the respective anatomical image file.

The step of receiving a segmentation map image file and the respective anatomical image file is advantageously performed automatically in the absence of a user requesting the display of the results of the step of detecting the first visual finding.

The segmentation map image file may have been compressed using a lossless compression algorithm. The segmentation map image file may be a PNG file.

As the skilled person understands, where a plurality of visual findings were detected in a single respective anatomical image, resulting in a plurality of segmentation map image files, the respective anatomical image file may only be sent to/received by the user device once. In other words, the methods may comprise determining that a segmentation map image file is associated with a respective medical image file that has already been sent to/received by the user device, and sending the segmentation map image file but not the respective anatomical image file.

In embodiments of any aspect, the segmentation map image file comprises a non-transparent pixel corresponding to every location of the respective anatomical image where the first visual finding has been detected.

Such image files may be referred to as transparent background files. The transparent file may be a binary transparent file. In a binary transparent file, every pixel is either transparent or not transparent (typically opaque). In embodiments, the transparent file comprises more than two levels of transparency. For example, the transparent file may comprise a first level for transparent pixels, a second level for opaque pixels, and a third level for semi-transparent pixels.

The segmentation map image file may comprise non-transparent pixels with a first level of transparency corresponding to the outline of every area of the respective anatomical image where the first visual finding has been detected, and non-transparent pixels with a second level of transparency corresponding to locations of the respective anatomical image where the first visual finding has been detected that are within an outlined area.

The second level of transparency may be higher (i.e. more transparent) than the first level of transparency. For example, the first level of transparency may specify opaque pixels, and the second level of transparency may specify semi-transparent pixels.

The first segmentation map image file and the respective anatomical image file may have substantially the same size. Every pixel of the first segmentation map image file may correspond to a respective pixel of the respective anatomical image file.

The method may further comprise resizing, by the processor or the user device processor, the first segmentation map image file and/or the respective anatomical image file such that every pixel of the first segmentation map image file corresponds to a respective pixel of the respective anatomical image file.

The method may further comprise repeating the steps of receiving and communicating or displaying using the results of a step of analysing the one or more anatomical images of a subject using one or more deep learning models trained to detect at least a further visual finding in anatomical images, wherein the results comprise at least a further segmentation map indicating the areas of a respective anatomical image where the further visual finding has been detected.

Any of the features related to automatically sending/receiving the results of a step of analysing one or more anatomical images of a subject may be performed in combination with the features associated with the communication of the first segmentation map image file as a separate file from the respective anatomical image file, or in the absence of the latter (e.g. in combination with the sending of the segmentation map information as part of a file that also comprises the respective anatomical image information). As such, also described herein are methods comprising: receiving, by a processor, the results of a step of analysing one or more anatomical images of a subject using one or more deep learning models trained to detect at least a first and optionally one or more further visual finding in anatomical images, wherein the results comprise at least a first (respectively, further) segmentation map indicating the areas of a respective anatomical image where the first (respectively, further) visual finding (has been detected; and communicating, by the processor, the result of the analysing step to a user by: sending to a user device at least the first (respectively, further) segmentation map and the respective anatomical image in the absence of a user requesting the display of the results of the step of detecting the first (of further) visual finding.

Similarly, also described herein are methods comprising: receiving, by a processor of a user device, the results of a step of analysing one or more anatomical images of a subject using one or more deep learning models trained to detect at least a first (respectively, further) visual finding in anatomical images, wherein receiving the results comprise receiving at least the first (respectively, further) segmentation map and the respective anatomical image in the absence of a user requesting the display of the results of the step of detecting the first (of further) visual finding; and displaying the information in the first (respectively, further) segmentation map to the user upon receiving a request to display the results of the step of detecting the first (of further) visual finding.

The methods described herein may further comprise the step of determining an order of priority for a plurality of visual findings, wherein the step of sending/receiving a segmentation map image file is performed automatically for the plurality of visual findings according to the determined order of priority.

The method may further comprise the processor communicating and/or the user computing device processor displaying a list of visual findings comprising the plurality of visual findings, wherein determining an order of priority for the plurality of visual findings comprises receiving a user selection of a visual finding in the displayed list of visual findings and prioritising visual findings that are closer to the user selected visual finding on the displayed list, relative to the visual findings that are further from the user selected visual finding.

The segmentation map may be produced using a method according to any one or more embodiments of the first, second or third aspect, and/or a user interface providing for user selection of, and interaction with, visual findings may be provided using a method according to any one or more embodiments of the seventh aspect.

In a ninth aspect, there is provided a method of training a neural network to detect a visual finding in anatomical images that is characterised by a ratio of two distances between two corresponding pairs of points, comprising:
retrieving, from a data store, a training dataset including, for each of a plurality of subjects, one or more anatomical images, and a plurality of labels associated with the one or more anatomical images, wherein one or more of the labels indicates the presence of the visual finding characterised by a ratio of distances between two pairs of points;
training the neural network using the training dataset, wherein the training comprises evaluating performance of the neural network in detecting the presence of the visual finding using a modified loss function which includes a loss weighting based upon a combination of:
errors derived from squared differences between coordinate values of pairs of points in the training dataset and corresponding pairs of points predicted by the neural network during training,
errors derived from squared differences between distances between pairs of points in the training dataset and corresponding pairs of points predicted by the neural network during training, and
errors derived from squared differences between the ratios of distances between pairs of points in the training dataset and corresponding pairs of points predicted by the neural network during training.

In embodiments, the loss weighting is defined by:

$$L_W = aP + bD + cR$$

where:
a, b, and c are constant multipliers;
P is the mean squared error (MSE) resulting from differences between coordinate values of pairs of points in the training dataset and corresponding pairs of points predicted by the neural network during training;
D is a combined measure of the MSE differences between distances between pairs of points in the training dataset and corresponding pairs of points predicted by the neural network during training; and
R is a measure of differences between the ratios of distances between pairs of points in the training dataset and corresponding pairs of points predicted by the neural network during training.

In embodiments, the constant multipliers a, b, and c may be determined based upon limitations in pixel error (e.g. due to image dimensions, resolution, etc.). The combined measure of the MSE differences used to determine D may be mean, weighted average, or median. The measure of differences between the ratios of distances used to determine R may be MSE of the ratio.

In embodiments, the visual finding may be cardiomegaly, the distances may be heart width and thorax width, and the ratio of distance may be the cardiothoracic ratio.

Embodiments of the ninth aspect may be employed in the training of neural networks according to any one or more embodiments of the methods of the fourth, fifth or sixth aspects.

In a further aspect, there is provided non-transitory computer readable storage media comprising instructions that, when executed by at least one processor, cause the at least one processor to perform operations comprising the steps of the method of any embodiment of the preceding aspects.

In a further aspect, there is provided an apparatus or system comprising:
at least one processor; and
at least one non-transitory computer readable medium containing instructions that, when executed by the at least one processor, cause the at least one processor to perform operations comprising the steps of the method of any embodiment of the preceding aspects.

In further aspects, there are provided methods of diagnosis and/or treatment of one or more medical conditions in a subject, such methods comprising analysing an anatomical image from the subject, or a portion thereof, using a method according to any one or more embodiments of the first, second or third aspect.

For example, embodiments of the invention provide methods for diagnosis and/or treatment of pneumothoraces in a subject, such methods comprising detecting a plurality of radiological findings in one or more CXR images of the subject, wherein the plurality of radiological findings includes at least pneumothoraces. The subject may be treated for pneumothoraces if the output of the neural network indicates the presence of pneumothoraces in the one or more CXR images of the subject. The plurality of radiological findings may include at least simple pneumothoraces and tension pneumothoraces. The method may comprise treating the subject according to a first course of treatment if the output of the neural network indicates the presence of tension pneumothoraces in the one or more anatomical images of the subject.

Further aspects, advantages, and features of embodiments of the invention will be apparent to persons skilled in the relevant arts from the following description of various embodiments. It will be appreciated, however, that the invention is not limited to the embodiments described, which are provided in order to illustrate the principles of the invention as defined in the foregoing statements and in the appended claims, and to assist skilled persons in putting these principles into practical effect.

BRIEF DESCRIPTION OF THE FIGURES

Embodiments of the invention will be described in detail with reference to the accompanying drawings, in which like reference numerals indicate like features, and wherein.

DETAILED DESCRIPTION

System Overview

Figure 1:
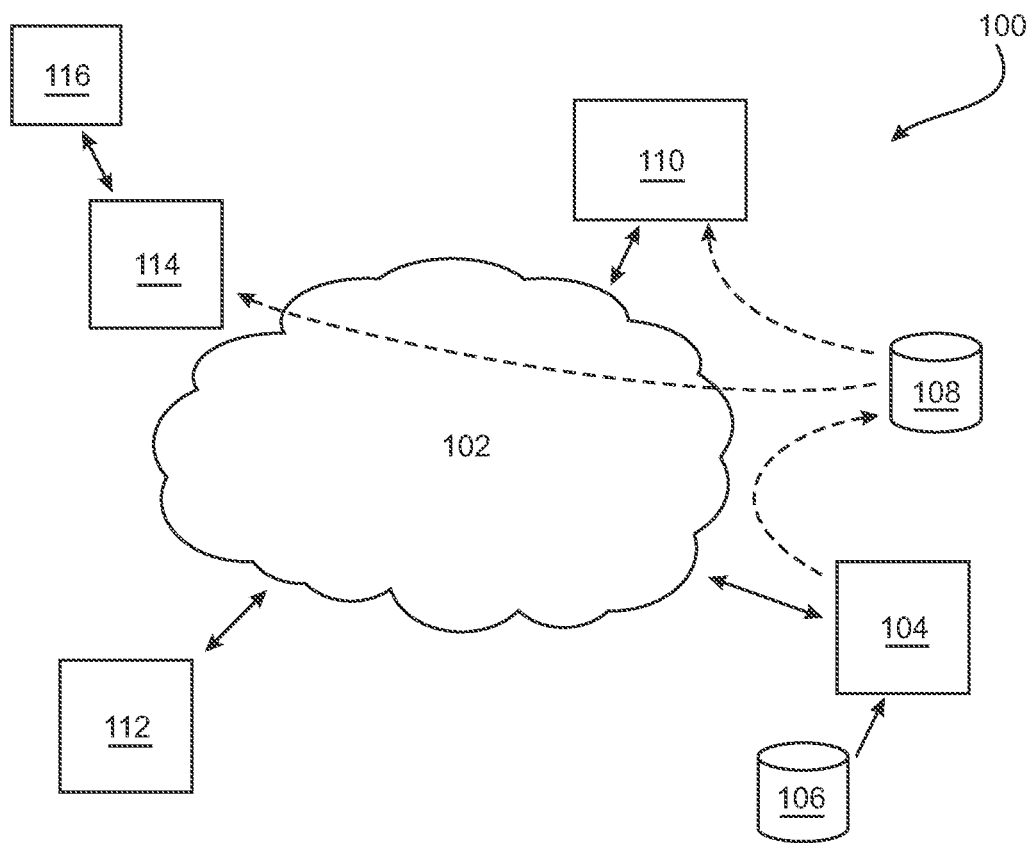
FIG. 1 is a block diagram illustrating an exemplary networked system embodying the invention.

FIG. 1 is a block diagram illustrating an exemplary system 100 in which a network 102, e.g. the Internet, connects a number of components individually and/or collectively embodying the invention. The system 100 is configured for training of machine learning models embodying the invention, and for execution of the trained models to provide analysis of anatomical images. Analysis services provided by the system 100 may be served remotely, e.g. by software components executing on servers and/or cloud computing platforms that provide application programming interfaces (APIs) that are accessible via the Internet 102. Additionally, or alternatively, the system 100 may enable on-site or on-premise execution of trained models for provision of local image analysis services and may be remotely accessible via a secure Virtual Private Network (VPN) connection. As will be apparent to skilled persons from the following description of embodiments of the invention, systems having the general features of the exemplary networked system 100 may be implemented in a variety of ways, involving various hardware and software components that may be located on-site, at remote server locations, and/or provided by cloud computing services. It will be understood that all such variations available to persons skilled in the art, such as software engineers, fall within the scope of the present disclosure. For simplicity, however, only a selection of exemplary embodiments will be described in detail.

The system 100 includes a model training platform 104, which comprises one or more physical computing devices, each of which may comprise one or more central processing units (CPUs), one or more graphics processing units (GPUs), memory, storage devices, and so forth, in known configurations. The model training platform 104 may comprise dedicated hardware, or may be implemented using cloud computing resources. The model training platform 104 is used in embodiments of the invention, as described herein, to train one or more machine learning models to provide analysis of anatomical images. For the purposes of such training, the model training platform is configured to access a data store 106 that contains training data that has been specifically prepared, according to embodiments of the invention, for the purposes of training the machine learning models. Trained models are stored within the system 100 within a data store 108, from which they may be made accessible to other components of the system 100. The data store 100 may comprise a dedicated data server, or may be provided by a cloud storage system.

Figure 7A:
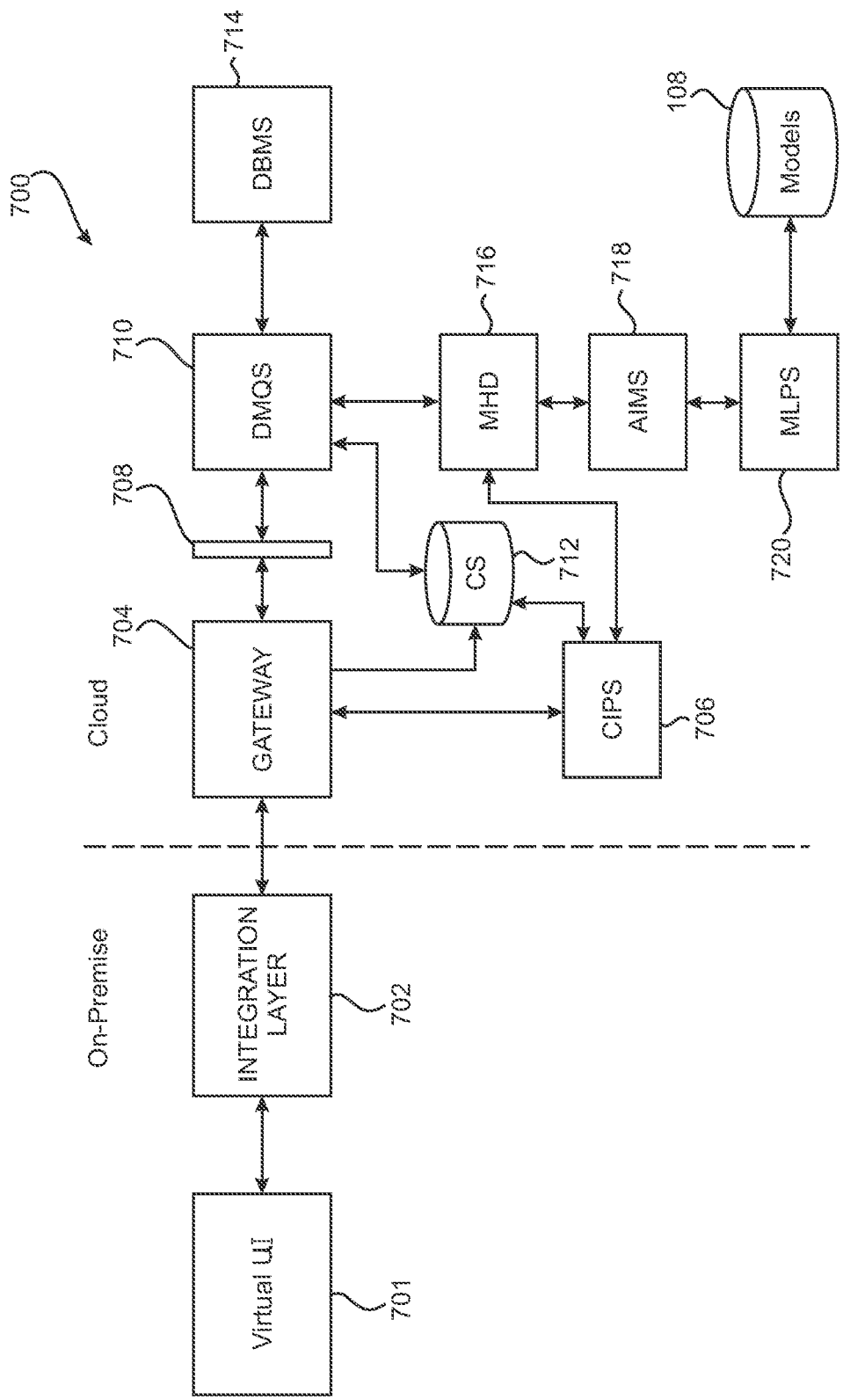
FIG. 7A is a block diagram of an exemplary microservices architecture of a medical image analysis system embodying the invention.
Figure 7B:
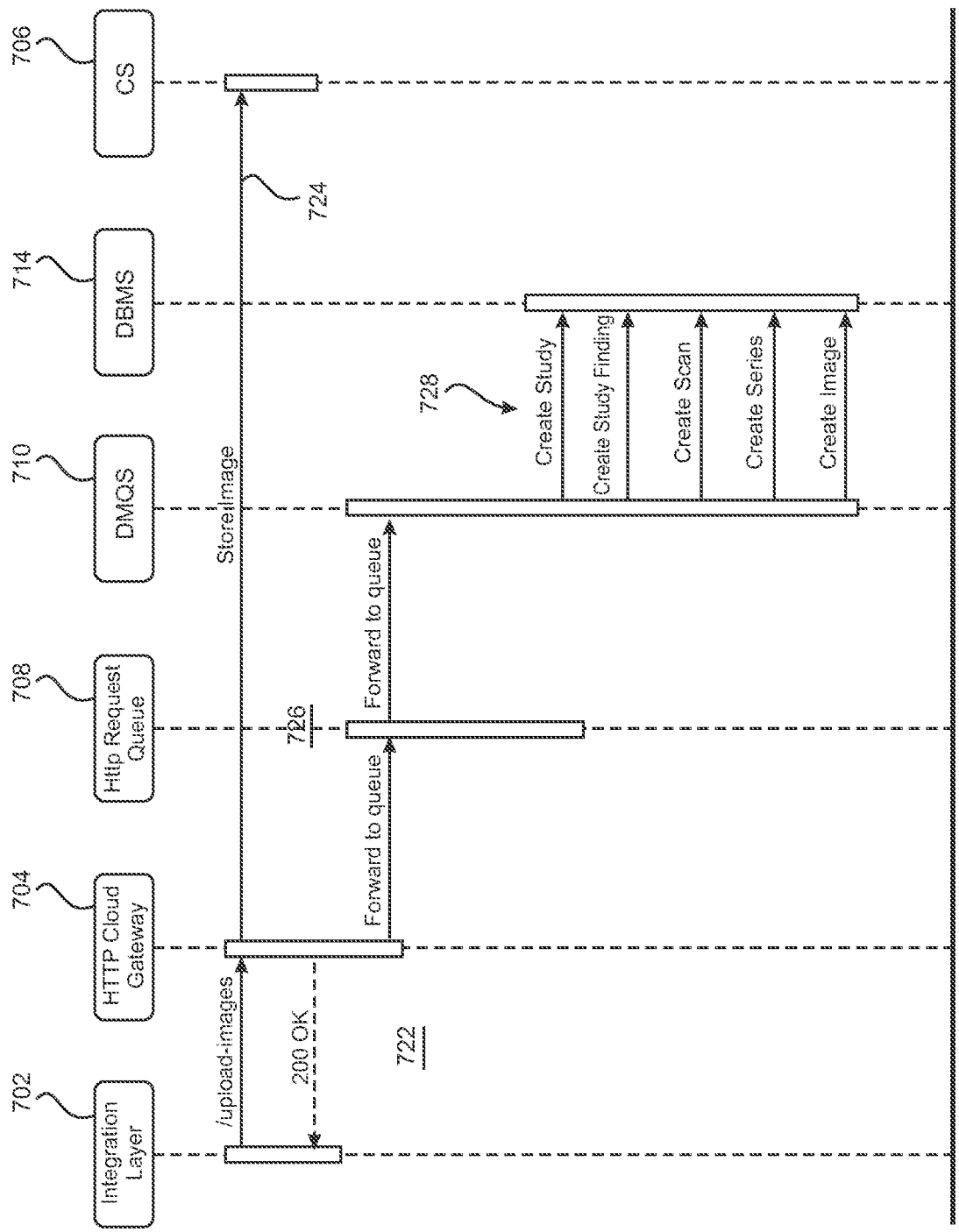
FIG. 7B is a signal flow diagram illustrating an exemplary method for initiating processing of medical imaging study results within the embodiment of FIG. 7A.
Figure 7C:
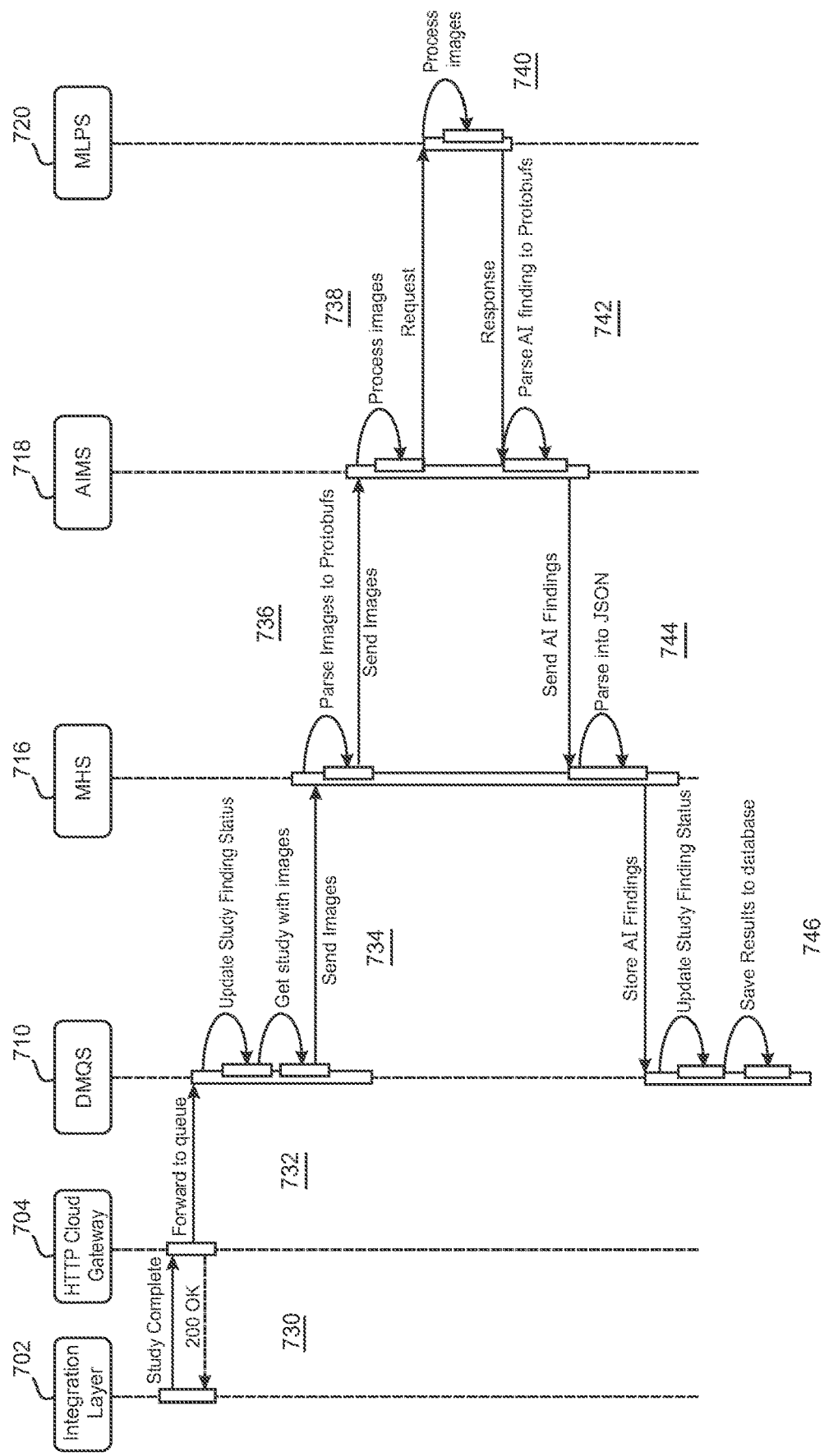
FIG. 7C is a signal flow diagram illustrating an exemplary method for processing and storage of medical imaging study results within the embodiment of FIG. 7A.

The system 100 further comprises a radiology image analysis server (RIAS) 110. An exemplary RIAS 110, which is described in greater detail herein with reference to FIGS. 7A to 7C, is based on a microservices architecture, and comprises a number of modular software components developed and configured in accordance with principles of the present invention. The RIAS 110 receives anatomical image data that is transmitted from a source of anatomical image data, for example, where the anatomical image data captured and initially stored such as a radiological clinic or its data centre. The transmission may occur in bulk batches of anatomical image data and prior to a user having to provide their decision/clinical report on a study. The transmission may be processed, controlled and managed by an integration layer (comprising integrator services of an integration adapter) installed at the radiological clinic or its data centre, or residing at cloud infrastructure.

In the clinical use scenario, the RIAS 110 provides analysis services in relation to anatomical images captured by and/or accessible by user devices, such as radiology terminals/workstations 112, or other computing devices (e.g. personal computers, tablet computers, and/or other portable devices—not shown). The anatomical image data is analysed by one or more software components of the RIAS 110, including through the execution of machine learning models. The RIAS 110 then makes the results of the analysis available and accessible to one or more user devices.

In other arrangements, which may exist in addition or as alternatives to the RIAS 110, an on-site radiology image analysis platform 114 may be provided. The on-site platform 114 comprises hardware, which may include one or more CPUs, and preferably one or more GPUs, along with software that is configured to execute machine learning models embodying the invention. The on-site platform 114 may thereby be configured to provide anatomical image data analysis equivalent to that provided by a remote RIAS 110, accessible to a user of, e.g., a radiology terminal 116. Machine learning models executed by the on-site platform 114 may be held in local storage and/or may be retrieved from the model data store 108. Updated models, when available, may be downloaded from the model store 108, or may be provided for download from another secure server (not shown), or made available for installation from physical media, such as CD-ROM, DVD-ROM, a USB memory stick, portable hard disk drive (HDD), portable solid-state drive (SDD), or other storage media.

With regard to the preceding overview of the system 100, and other processing systems and devices described in this specification, terms such as 'processor', 'computer', and so forth, unless otherwise required by the context, should be understood as referring to a range of possible implementations of devices, apparatus and systems comprising a combination of hardware and software. This includes single-processor and multi-processor devices and apparatus, including portable devices, desktop computers, and various types of server systems, including cooperating hardware and software platforms that may be co-located or distributed. Physical processors may include general purpose CPUs, digital signal processors, GPUs, and/or other hardware devices suitable for efficient execution of required programs and algorithms.

Computing systems may include conventional personal computer architectures, or other general-purpose hardware platforms. Software may include open-source and/or commercially available operating system software in combination with various application and service programs. Alternatively, computing or processing platforms may comprise custom hardware and/or software architectures. As previously noted, computing and processing systems may comprise cloud computing platforms, enabling physical hardware resources, including processing and storage, to be allocated dynamically in response to service demands.

Terms such as 'processing unit', 'component', and 'module' are used in this specification to refer to any suitable combination of hardware and software configured to perform a particular defined task. Such a processing unit, components, or modules may comprise executable code executing at a single location on a single processing device, or may comprise cooperating executable code modules executing in multiple locations and/or on multiple processing devices. Where exemplary embodiments are described herein with reference to one such architecture (e.g. cooperating service components of the cloud computing architecture described with reference to FIGS. 7A to 7C) it will be appreciated that, where appropriate, equivalent functionality may be implemented in other embodiments using alternative architectures.

Software components embodying features of the invention may be developed using any suitable programming language, development environment, or combinations of languages and development environments, as will be familiar to persons skilled in the art of software engineering. For example, suitable software may be developed using the TypeScript programming language, the Rust programming language, the Go programming language, the Python programming language, the SQL query language, and/or other languages suitable for implementation of applications, including web-based applications, comprising statistical modeling, machine learning, data analysis, data storage and retrieval, and other algorithms. Implementation of embodiments of the invention may be facilitated by the used of available libraries and frameworks, such as TensorFlow or PyTorch for the development, training and deployment of machine learning models using the Python programming language.

It will be appreciated by skilled persons that embodiments of the invention involve the preparation of training data, as well as the implementation of software structures and code that are not well-understood, routine, or conventional in the art of anatomical image analysis, and that while pre-existing languages, frameworks, platforms, development environments, and code libraries may assist implementation, they require specific configuration and extensive augmentation (i.e. additional code development) in order to realize various benefits and advantages of the invention and implement the specific structures, processing, computations, and algorithms described herein with reference to the drawings.

The foregoing examples of languages, environments, and code libraries are not intended to be limiting, and it will be appreciated that any convenient languages, libraries, and development systems may be employed, in accordance with system requirements. The descriptions, block diagrams, flowcharts, tables, and so forth, presented in this specification are provided, by way of example, to enable those skilled in the arts of software engineering, statistical modeling, machine learning, and data analysis to understand and appreciate the features, nature, and scope of the invention, and to put one or more embodiments of the invention into effect by implementation of suitable software code using any suitable languages, frameworks, libraries and development systems in accordance with this disclosure without exercise of additional inventive ingenuity.

The program code embodied in any of the applications/modules described herein is capable of being individually or collectively distributed as a program product in a variety of different forms. In particular, the program code may be distributed using a computer readable storage medium having computer readable program instructions thereon for causing a processor to carry out aspects of the embodiments of the invention.

Computer readable storage media may include volatile and non-volatile, and removable and non-removable, tangible media implemented in any method or technology for storage of information, such as computer-readable instructions, data structures, program modules, or other data. Computer readable storage media may further include random access memory (RAM), read-only memory (ROM), erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Computer readable program instructions may be downloaded via transitory signals to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts, sequence diagrams, and/or block diagrams. The computer program instructions may be provided to one or more processors of a general purpose computer, a special purpose computer, or other programmable data processing apparatus to produce a machine, such that the instructions, which execute via the one or more processors, cause a series of computations to be performed to implement the functions, acts, and/or operations specified in the flowcharts, sequence diagrams, and/or block diagrams.

DICOM Standard

Embodiments of the invention advantageously employ the Digital Imaging and Communications in Medicine (DICOM) standard, which is commonly used in medical imaging systems. The DICOM instance information model describes a hierarchical set of identifiers: the patient ID, and the study, series and service object pair (SOP) Unique Identifiers (UIDs). Each patient may have multiple studies. Each study may have multiple series. Each series may contain multiple SOPs. The four text identifiers in the DICOM standard have the following properties:
1. Patient ID—a non-globally unique identifier, intended to be unique within the context of an imaging service to identify individual patients'
2. Study UID—a globally unique ID (UID) capturing a set of image series, which are acquired within a single given context (e.g. a single visit);
3. Series UID—a globally unique ID consisting of only one modality (e.g. x-ray) produced by only one piece of imaging equipment; and
4. SOP Instance UID—a globally unique ID referencing a single image (or non-image) DICOM instance.

Regarding these identifiers:
a study may contain multiple series of different modalities;
a series may consist of multiple SOP instances (usually images); and
a DICOM instance may, for example, represent a single x-ray view, or a single frame of a stack of images in a computerized tomography (CT) series.

DICOM mechanisms ensure the uniqueness of each identifier that is required to be globally unique ID.

In embodiments of the invention as described herein, medical images (also referred to herein as 'anatomical images') produced by imaging equipment comprise image data, and image metadata including DICOM headers. Such images, also referred to simply as 'DICOM images', may be stored, transmitted between components of the system 100, employed for training of machine learning (ML) models, and provided as input for analysis by trained models.

Model Architecture

Embodiments of the invention are configured for analysis of anatomical images using statistical classifiers that include one or more deep learning models, and for communication of the results to user devices. Preferably, the models comprise deep neural networks such as convolutional neural networks (ConvNets or CNNs). CNN components can be used as statistical classifiers/neural networks that take an image as input, and output a feature vector. An anatomical image (or medical image) is a two-dimensional image of a body portion of a subject, obtained using anatomical imaging means such as e.g. an x-ray machine, an MRI machine, a CT scanner, etc. Exemplary body portions include: a chest; an abdomen; a breast; a limb; a joint, and/or portion of a limb, such as shoulder, hip, wrist, and elbow; and so forth. For example, the body portion may be the chest and the imaging modality may be x-ray, therefore the anatomical image may be a chest x-ray (CXR) image. In some cases, the CXR image is a digital x-ray, i.e. an image obtained by computed radiography (CR) or digital radiography (DR).

The convolutional layers of a CNN take advantage of inherent properties of the medical images. The CNN takes advantage of local spatial coherence of medical images. This means that CNNs are generally able to dramatically reduce the number of operations needed to process a medical image by using convolutions on grids of adjacent pixels due to the importance of local connectivity. Each map is then filled with the result of the convolution of a small patch of pixels, by applying a sliding window algorithm over the whole image. Each window consists of a convolutional filter having weights and is convolved with the medical image (i.e. slide over the medical image spatially, computing dot products). The output of each convolutional filter is processed by a non-linear activation function, generating an activation map/feature map. The CNN has pooling layers which downscale the medical image. This is possible because features that are organised spatially are retained throughout the neural network, and thus downscaling them reduces the size of the medical image. When designing the CNN, the number of convolutional layers, filters and their size, alongside the type of activation function and the pooling method are carefully considered and selected to optimise model performance. Advantageously, transfer learning can be applied. Transfer learning consists of using pre-trained weights developed by training the same model architecture on a larger (potentially unrelated) dataset, such as the ImageNet dataset (http://www.image-net.org). Training on the dataset related to the problem at hand by initialising with pre-trained weights allows for certain features to already be recognised and increases the likelihood of finding a global, or reduced local, minimum for the loss function than otherwise.

As used herein, references to using a deep neural network (DNN) to classify image data may in practice encompass using an ensemble of DNNs by combining the predictions of individual DNNs. Each ensemble may have the properties described herein. Similarly, references to training a DNN may in fact encompass the training of multiple DNNs as described herein, some or all of which may subsequently be used to classify image data, as the case may be.

Figure 2:
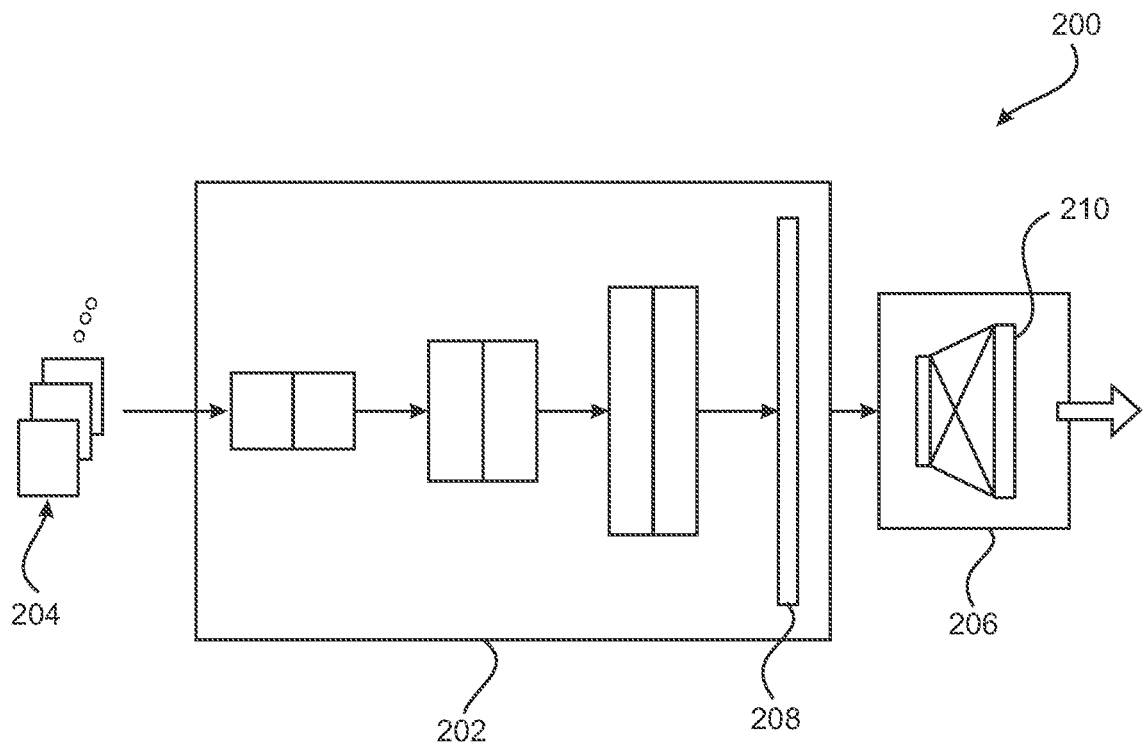
FIG. 2 is a schematic illustration of a vision classification model embodying the invention.

A CNN component can be designed to process anatomical images corresponding to a defined orientation of the subject. In one embodiment, as illustrated in FIG. 2, a Vision Classification model 200 comprises a single weight-shared multi-stage CNN component 202 that is configured to process all views (e.g. lateral, frontal, AP, PA, etc) of input anatomical images 204. The CNN component 202 may be implemented, for example, based on EfficientNetB0, as described in Tan, M., and Le, Q. V. 'EfficientNet: Rethinking model scaling for convolutional neural networks', *ICML*, arXiv:1905.11946 (2019).

The feature vectors output by the CNN component 202 may be combined and fed into a dense layer 206, which is a fully connected layer that converts 2D feature maps 208 into a 1D feature vector 210. In some embodiments, the feature vectors may be extracted following an average pooling layer. In some embodiments the dense layer is customised. In some embodiments, the dense layer is a final layer and comprises a predetermined number of visual findings as nodes. Each node then outputs an indication of the probability of the presence of each of a plurality of visual findings in at least one of the input images 204. Alternatively or additionally, a prediction and optionally a confidence in this prediction may be output.

Deep learning models embodying the invention can advantageously be trained to detect/classify a very high number of visual findings, such as, e.g., 188 findings as described in greater detail below with reference to Table 1. Such models may have been trained using CXR images (pixel data) where, in one example, labels were provided for each of 188 findings (including corresponding to visual findings), enabling the deep learning models to be trained to detect combinations of findings, while preventing the models from learning incorrect correlations. In some embodiments, as also described in greater detail below, the models can be trained to detect negative pairs, defined as the detection of a first finding in the absence of a second finding, where the first and second findings are known to have a statistically significant correlation therebetween.

Figure 3:
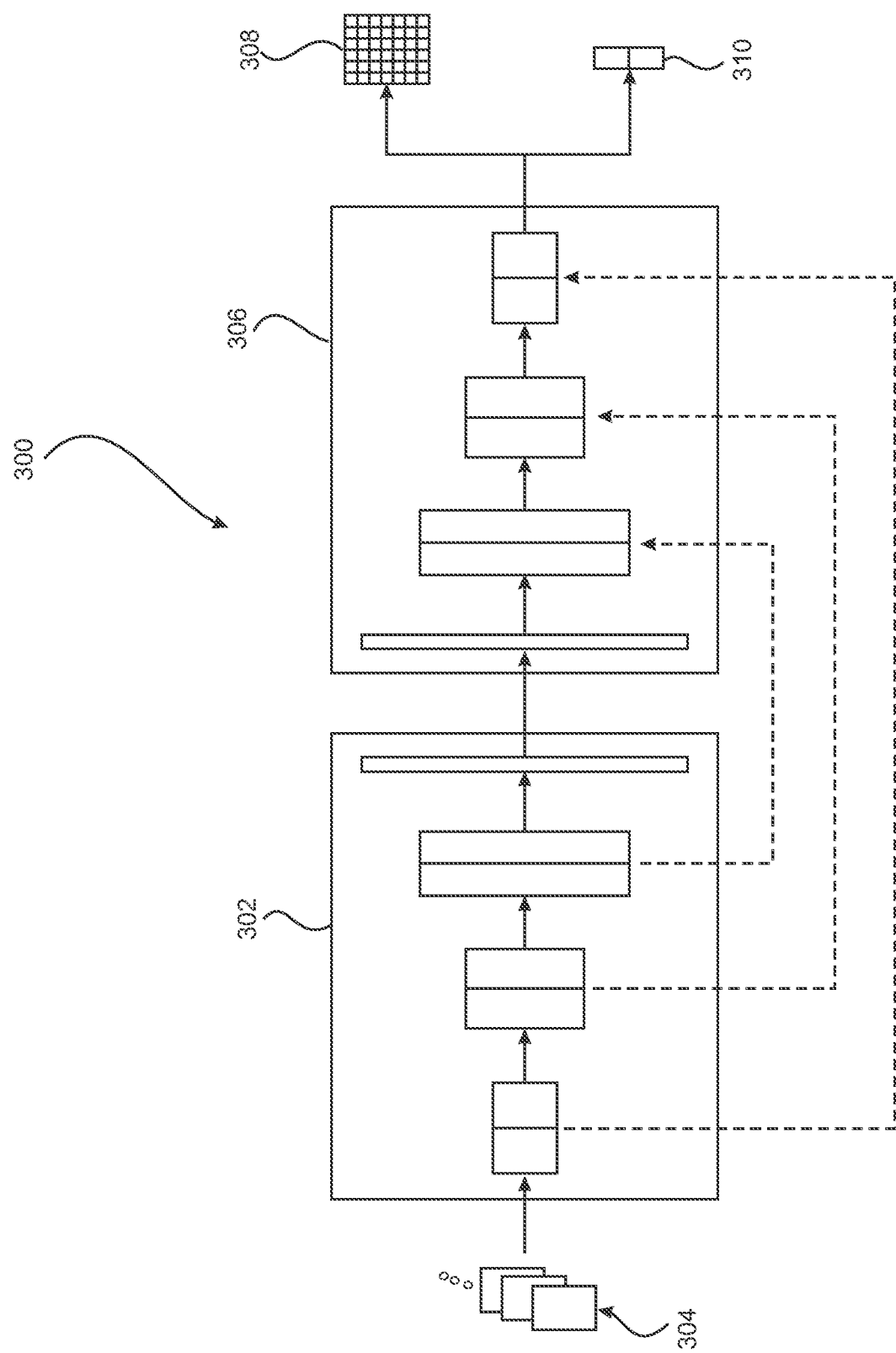
FIG. 3 is a schematic illustration of a vision segmentation model embodying the invention.

In some embodiments, as illustrated in FIG. 3, a Vision Segmentation model 300 comprises a first CNN component 302 that is configured to process input anatomical images 304. The first CNN component 302 functions as an encoder, and is connected to a second CNN component 306 which functions as a decoder. The encoder 302 and decoder 306 may comprise a U-Net model, as described in Ronneberger, O., Fischer, P. and Brox, T., 'U-Net: Convolutional Networks for Biomedical Image Segmentation', arXiv: 1505.04597 (2015), or a feature pyramid network (FPN), based on an EfficientNet backbone. The encoder 302 may then advantageously be shared with the Vision Classification model 200, i.e. the CNN components 202 and 302 may comprise a single shared component. The EfficientNet backbone provides representations at different spatial resolutions (e.g. fine to coarse), which are aggregated within the U-Net or FPN structure to generate a MAP output 308. The MAP 308 comprises a two-dimensional array of values representing a probability that the corresponding pixel of the input anatomical image exhibits a visual finding, e.g. as identified by the Vision Classification model 200. Additionally, a classification output 310 may be provided, e.g. to identify laterality.

Figure 4:
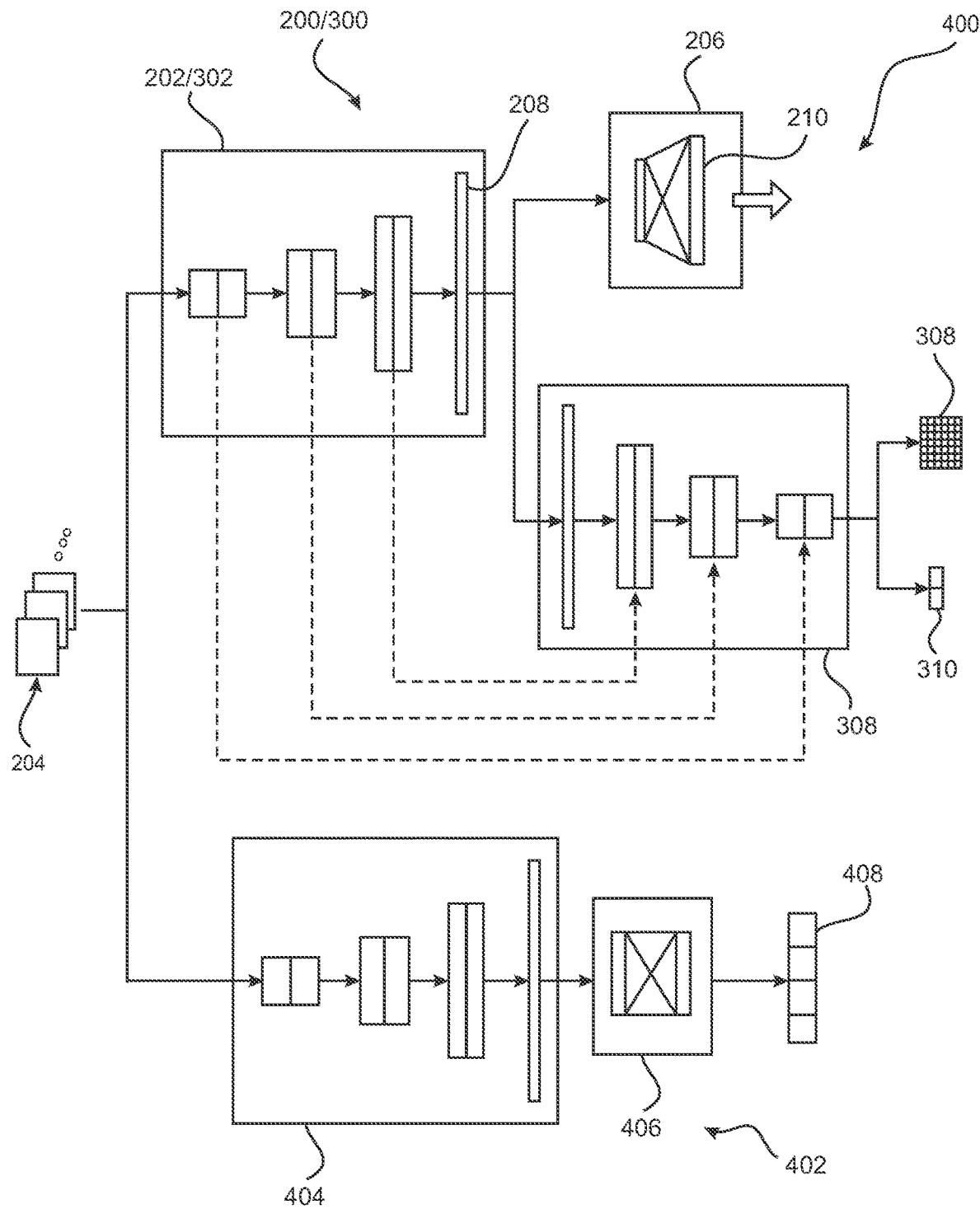
FIG. 4 is a schematic illustration of a vision classification model and a vision segmentation model having a share convolutional neural network component, in combination with a vision attributes model embodying the invention.

FIG. 4 illustrates a further exemplary embodiment 400 which comprises a Vision Classification model 200, the Vision Segmentation model 300, and an additional Vision Attributes model 402. In this embodiment, a shared CNN component 202/302 is provided which produces a feature vector 208 that is used by two branches: a first branch comprising the fully connected layer 206 that generates the classification feature vector 210; and a second branch comprising the decoder 306 that is used to generate the MAP 308 and laterality feature vector 310. This arrangement may be referred to simply as a 'Vision model' 400, and comprises a Y net with a common encoder backbone (producing the feature vector 208) with two output heads: Classification, Segmentation.

The summary for the layers of the model 200 which are nested, are:

SUMMARY FOR "model_2":
Model: "model_2"

| Layer (type) | Output Shape | Param # | Connected to |
|---|---|---|---|
| input (InputLayer) | [(None, None, 1024, 1024, 1)] | 0 | |
| tf.compat.v1.shape (TFOpLambda) | (5,) | 0 | input[0][0] |
| tf._operators_.getitem (SlicingOpLambda) | () | 0 | tf.compat.v1.shape[0][0] |
| tf._operators_.getitem_1 (SlicingOpLambda) | ( ) | 0 | tf.compat.v1.shape[0][0] |
| tf.math.multiply (TFOpLambda) | ( ) | 0 | tf._operators_.getitem[0][0] tf._operators.getitem_1[0][0] |
| tf._operators_.getitem_2 (SlicingOpLambda) | ( ) | 0 | tf.compat.v1.shape[0][0] |
| tf_operators._getitem_3 (SlicingOpLambda) | ( ) | 0 | tf.compat.v1.shape[0][0] |
| tf._operators_.getitem_4 (SlicingOpLambda) | ( ) | 0 | tf.compat.v1.shape[0][0] |
| tf.reshape (TFOpLambda) | (None, None, None, None) | 0 | input[0][0] tf.math.multiply[0][0] tf._operators_.getitem_2[0][0] tf._operators_.getitem_3[0][0] tf_.operators_.getitem 4[0][0] |
| model_1 (Functional) | [(None, 512, 512, 16), (None, 32, 3) | 6378604 | tf.reshape[0][0] |
| tf.reshape_2 (TFOpLambda) | (None, None, 32, 32, 1280) | 0 | model_1 [0][1] tf._operators_.getitem[0][0] tf._operators_.getitem_1[0][0] |
| top_activations (Lambda) | (None, None, 32, 32, 1280) | 0 | tf.reshape_2[0][0] |
| tf. math.reduce_max (TFOpLambda) | (None, 1280) | 0 | top_activations[0][0] |
| tf.math.reduce_mean (TFOpLambda) | (None, 1280) | 0 | top_activations[0][0] |

-continued

Model: "model_2"

| Layer (type) | Output Shape | Param # | Connected to |
|---|---|---|---|
| tf.concat (TFOpLambda) | (None, 2560) | 0 | tf.math.reduce_max[0][0] tf.math.reduce_mean[0][0] |
| dropout (Dropout) | (None, 2560) | 0 | tf.concat[0][0] |
| tf.reshape_1 (TFOpLambda) | (None, None, 512, 512, 16) | 0 | model_1 [0][0] tf._operators_.getitem[0][0] tf._operators_.getitem_1[0][0] |
| logits (Dense) | (None, 263) | 673543 | dropout[0][0] |
| seg (Lambda) | (None, None, 512, 512, 16) | 0 | tf.reshape_1 [0][0] |
| cis (Activation) | (None, 263) | 0 | logits[0][0] |

Total params: 7,052,147
Trainable params: 7,009,107
Non-trainable params: 43,040
SUMMARY FOR "model_1":
Model: "model_1"

| Layer (type) | Output Shape | Param # | Connected to |
|---|---|---|---|
| input_1 (InputLayer) | [(None, 1024, 1024, 1)] | 0 | |
| stem_conv (Conv2D) | (None, 512, 512, 32) | 288 | input_1 [0][0] |
| stem_bn (BatchNormalization) | (None, 512, 512, 32) | 128 | stem_conv[0][0] |
| stem_activation (Activation) | (None, 512, 512, 32) | 0 | stem_bn[0][0] |
| block1a_dwconv (DepthwiseConv2D) | (None, 512, 512, 32) | 288 | stem_activation[0][0] |
| block1a_bn (BatchNormalization) | (None, 512, 512, 32) | 128 | block1a_dwconv[0][0] |
| block1a_activation (Activation) | (None, 512, 512, 32) | 0 | block1a_bn[0][0] |
| block1a_se_squeeze (GlobalAveragePooling2D) | (None, 32) | 0 | block1a_activation[0][0] |
| block1a_se_reshape (Reshape) | (None, 1, 1,32) | 0 | block1a_se_squeeze[0][0] |
| block1a_se_reduce (Conv2D) | (None, 1,1,8) | 264 | block1a_se_reshape[O][O] |
| block1a_se_expand (Conv2D) | (None, 1, 1,32) | 288 | block1a_se_reduce[0][0] |
| block1a_se_excite (Multiply) | (None, 512, 512, 32) | 0 | block1a_activation[0][0] block1a_se_expand[0][0] |
| block1a_project_conv (Conv2D) | (None, 512, 512, 16) | 512 | block1a_se_excite[0][0] |
| block1a_project_bn (BatchNormalization) | (None, 512, 512, 16) | 64 | block1a_project_conv[0][0] |
| block2a_expand_conv (Conv2D) | (None, 512, 512, 96) | 1536 | block1a_project_bn[0][0] |
| block2a_expand_bn (BatchNormalization) | (None, 512, 512, 96) | 384 | block2a_expand_conv[0][0] |
| block2a_expand_activation (Activation) | (None, 512, 512, 96) | 0 | block2a_expand_bn[0][0] |
| block2a_dwconv (DepthwiseConv2D) | (None, 256, 256, 96) | 864 | block2a_expand_activation[0][0] |
| block2a_bn (BatchNormalization) | (None, 256, 256, 96) | 384 | block2a_dwconv[0][0] |
| block2a_activation (Activation) | (None, 256, 256, 96) | 0 | block2a_bn[0][0] |
| block2a_se_squeeze (GlobalAveragePooling2D) | (None, 96) | 0 | block2a_activation[0][0] |
| block2a_se_reshape (Reshape) | (None, 1, 1,96) | 0 | block2a_se_squeeze[0][0] |
| block2a_se_reduce (Conv2D) | (None, 1,1,4) | 388 | block2a_se_reshape[0][0] |
| block2a_se_expand (Conv2D) | (None, 1, 1,96) | 480 | block2a_se_reduce[0][0] |
| block2a_se_excite (Multiply) | (None, 256, 256, 96) | 0 | block2a_activation[0][0] block2a_se_expand[0][0] |
| block2a_project_conv (Conv2D) | (None, 256, 256, 24) | 2304 | block2a_se_excite[0][0] |
| block2a_project_bn (BatchNormalization) | (None, 256, 256, 24) | 96 | block2a_project_conv[0][0] |
| block2b_expand_conv (Conv2D) | (None, 256, 256, 144) | 3456 | block2a_project_bn[0][0] |
| block2b_expand_bn (BatchNormalization) | (None, 256, 256, 144) | 576 | block2b_expand_conv[0][0] |
| block2b_expand_activation (Activation) | (None, 256, 256, 144) | 0 | block2b_expand_bn[0][0] |
| block2b_dwconv (DepthwiseConv2D) | (None, 256, 256, 144) | 1296 | block2b_expand_activation[0][0] |
| block2b_bn (BatchNormalization) | (None, 256, 256, 144) | 576 | block2b_dwconv[0][0] |
| block2b_activation (Activation) | (None, 256, 256, 144) | 0 | block2b_bn[0][0] |
| block2b_se_squeeze (GlobalAveragePooling2D) | (None, 144) | 0 | block2b_activation[0][0] |
| block2b_se_reshape (Reshape) | (None, 1, 1, 144) | 0 | block2b_se_squeeze[0][0] |

-continued

Model: "model_1"

| Layer (type) | Output Shape | Param # | Connected to |
|---|---|---|---|
| block2b_se_reduce (Conv2D) | (None, 1,1,6) | 870 | block2b_se_reshape[0][0] |
| block2b_se_expand (Conv2D) | (None, 1, 1, 144) | 1008 | block2b_se_reduce[0][0] |
| block2b_se_excite (Multiply) | (None, 256, 256, 144) | 0 | block2b_activation[0][0] |
| | | | block2b_se_expand[0][0] |
| block2b_project_conv (Conv2D) | (None, 256, 256, 24) | 3456 | block2b_se_excite[0][0] |
| block2b_project_bn (BatchNormalization) | (None, 256, 256, 24) | 96 | block2b_project_conv[0][0] |
| block2b_drop (FixedDropout) | (None, 256, 256, 24) | 0 | block2b_project_bn[0][0] |
| block2b_add (Add) | (None, 256, 256, 24) | 0 | block2b_drop[0][0] |
| | | | block2a_project_bn[0][0] |
| block3a_expand_conv (Conv2D) | (None, 256, 256, 144) | 3456 | block2b_add[0][0] |
| block3a_expand_bn (BatchNormalization) | (None, 256, 256, 144) | 576 | block3a_expand_conv[0][0] |
| block3a_expand_activation (Activation) | (None, 256, 256, 144) | 0 | block3a_expand_bn [0] [0] |
| block3a_dwconv (DepthwiseConv2D) | (None, 128, 128, 144) | 3600 | block3a_expand_activation[0][0] |
| block3a_bn (BatchNormalization) | (None, 128, 128, 144) | 576 | block3a_dwconv[0][0] |
| block3a_activation (Activation) | (None, 128, 128, 144) | 0 | block3a_bn[0][0] |
| block3a_se_squeeze (GlobalAveragePooling2D) | (None, 144) | 0 | block3a_activation[0][0] |
| block3a_se_reshape (Reshape) | (None, 1, 1, 144) | 0 | block3a_se_squeeze[0][0] |
| block3a_se_reduce (Conv2D) | (None, 1,1,6) | 870 | block3a_se_reshape[0][0] |
| block3a_se_expand (Conv2D) | (None, 1, 1, 144) | 1008 | block3a_se_reduce[0][0] |
| block3a_se_excite (Multiply) | (None, 128, 128, 144) | 0 | block3a_activation[0][0] |
| | | | block3a_se_expand[0][0] |
| block3a_project_conv (Conv2D) | (None, 128, 128, 40) | 5760 | block3a_se_excite[0][0] |
| block3a_project_bn (BatchNormalization) | (None, 128, 128, 40) | 160 | block3a_project_conv[0][0] |
| block3b_expand_conv (Conv2D) | (None, 128, 128, 240) | 9600 | block3a_project_bn[0][0] |
| block3b_expand_bn (BatchNormalization) | (None, 128, 128, 240) | 960 | block3b_expand_conv[0][0] |
| block3b_expand_activation (Activation) | (None, 128, 128, 240) | 0 | block3b_expand_bn[0][0] |
| block3b_dwconv (DepthwiseConv2D) | (None, 128, 128, 240) | 6000 | block3b_expand_activation [0] [0] |
| block3b_bn (BatchNormalization) | (None, 128, 128, 240) | 960 | block3b_dwconv[0][0] |
| block3b_activation (Activation) | (None, 128, 128, 240) | 0 | block3b_bn[0][0] |
| block3b_se_squeeze (GlobalAveragePooling2D) | (None, 240) | 0 | block3b_activatlon[0][0] |
| block3b_se_reshape (Reshape) | (None, 1, 1,240) | 0 | block3b_se_squeeze[0][0] |
| block3b_se_reduce (Conv2D) | (None, 1,1,10) | 2410 | block3b_se_reshape[0][0] |
| block3b_se_expand (Conv2D) | (None, 1, 1,240) | 2640 | block3b_se_reduce[0][0] |
| block3b_se_excite (Multiply) | (None, 128, 128, 240) | 0 | block3b_activatlon[0][0] |
| | | | block3b_se_expand[0][0] |
| block3b_project_conv (Conv2D) | (None, 128, 128, 40) | 9600 | block3b_se_excite[0][0] |
| block3b_project_bn (BatchNormalization) | (None, 128, 128, 40) | 160 | block3b_project_conv[0][0] |
| block3b_drop (FixedDropout) | (None, 128, 128, 40) | 0 | block3b_project_bn[0][0] |
| block3b_add (Add) | (None, 128, 128, 40) | 0 | block3b_drop[0][0] |
| | | | block3a_project_bn[0][0] |
| block4a_expand_conv (Conv2D) | (None, 128, 128, 240) | 9600 | block3b_add[0][0] |
| block4a_expand_bn (BatchNormalization) | (None, 128, 128, 240) | 960 | block4a_expand_conv[0][0] |
| block4a_expand_activation (Activation) | (None, 128, 128, 240) | 0 | block4a_expand_bn[0][0] |
| block4a_dwconv (DepthwiseConv2D) | (None, 64, 64, 240) | 2160 | block4a_expand_activation[0][0] |
| block4a_bn (BatchNormalization) | (None, 64, 64, 240) | 960 | block4a_dwconv[0][0] |
| block4a_activation (Activation) | (None, 64, 64, 240) | 0 | block4a_bn[0][0] |
| block4a_se_squeeze (GlobalAveragePooling2D) | (None, 240) | 0 | block4a_activation[0][0] |
| block4a_se_reshape (Reshape) | (None, 1, 1,240) | 0 | block4a_se_squeeze[0][0] |
| block4a_se_reduce (Conv2D) | (None, 1,1,10) | 2410 | block4a_se_reshape[0][0] |
| block4a_se_expand (Conv2D) | (None, 1, 1,240) | 2640 | block4a_se_reduce[0][0] |
| block4a_se_excite (Multiply) | (None, 64, 64, 240) | 0 | block4a_activation[0][0] |
| | | | block4a_se_expand[0][0] |
| block4a_project_conv (Conv2D) | (None, 64, 64, 80) | 19200 | block4a_se_excite[0][0] |
| block4a_project_bn (BatchNormalization) | (None, 64, 64, 80) | 320 | block4a_project_conv[0][0] |
| block4b_expand_conv (Conv2D) | (None, 64, 64, 480) | 38400 | block4a_project_bn[0][0] |

-continued

Model: "model_1"

| Layer (type) | Output Shape | Param # | Connected to |
|---|---|---|---|
| block4b_expand_bn (BatchNormalization) | (None, 64, 64, 480) | 1920 | block4b_expand_conv[0] [0] |
| block4b_expand_activation (Activation) | (None, 64, 64, 480) | 0 | block4b_expand_bn[0][0] |
| block4b_dwconv (DepthwiseConv2D) | (None, 64, 64, 480) | 4320 | block4b_expand_activation[0][0] |
| block4b_bn (BatchNormalization) | (None, 64, 64, 480) | 1920 | block4 b_dwconv[0] [0] |
| block4b_activation (Activation) | (None, 64, 64, 480) | 0 | block4b_bn[0][0] |
| block4b_se_squeeze (GlobalAveragePooling2D) | (None, 480) | 0 | block4b_activation[0][0] |
| block4b_se_reshape (Reshape) | (None, 1, 1,480) | 0 | block4b_se_squeeze[0][0] |
| block4b_se_reduce (Conv2D) | (None, 1, 1,20) | 9620 | block4b_se_reshape[0][0] |
| block4b_se_expand (Conv2D) | (None, 1, 1,480) | 10080 | block4b_se_reduce[0][0] |
| block4b_se_excite (Multiply) | (None, 64, 64, 480) | 0 | block4b_activation[0][0] block4b se_expand[0][0] |
| block4b_project_conv (Conv2D) | (None, 64, 64, 80) | 38400 | block4b_se_excite[0][0] |
| block4b_project_bn (BatchNormalization) | (None, 64, 64, 80) | 320 | block4b_project_conv[0][0] |
| block4b_drop (FixedDropout) | (None, 64, 64, 80) | 0 | block4b_project_bn[0][0] |
| block4b_add (Add) | (None, 64, 64, 80) | 0 | block4b_drop[0][0] block4a_project_bn[0][0] |
| block4c_expand_conv (Conv2D) | (None, 64, 64, 480) | 38400 | block4b_add[0][0] |
| block4c_expand_bn (BatchNormalization) | (None, 64, 64, 480) | 1920 | block4c_expand_conv[0][0] |
| block4c_expand_activation (Activation) | (None, 64, 64, 480) | 0 | block4c_expand_bn[0][0] |
| block4c_dwconv (DepthwiseConv2D) | (None, 64, 64, 480) | 4320 | block4c_expand_activation[0][0] |
| block4c_bn (BatchNormalization) | (None, 64, 64, 480) | 1920 | block4c_dwconv[0][0] |
| block4c_activation (Activation) | (None, 64, 64, 480) | 0 | block4c_bn[0][0] |
| block4c_se_squeeze (GlobalAveragePooling2D) | (None, 480) | 0 | block4c_activation[0][0] |
| block4c_se_reshape (Reshape) | (None, 1, 1,480) | 0 | block4c_se_squeeze[0][0] |
| block4c_se_reduce (Conv2D) | (None, 1, 1,20) | 9620 | block4c_se_reshape[0][0] |
| block4c_se_expand (Conv2D) | (None, 1,1,480) | 10080 | block4c_se_reduce[0][0] |
| block4c_se_excite (Multiply) | (None, 64, 64, 480) | 0 | block4c_activation[0][0] block4c se_expand[0][0] |
| block4c_project_conv (Conv2D) | (None, 64, 64, 80) | 38400 | block4c_se_excite[0][0] |
| block4c_project_bn (BatchNormalization) | (None, 64, 64, 80) | 320 | block4c_project_conv[0][0] |
| block4c_drop (FixedDropout) | (None, 64, 64, 80) | 0 | block4c_project_bn[0][0] |
| block4c_add (Add) | (None, 64, 64, 80) | 0 | block4c_drop[0][0] block4b_add[0][0] |
| block5a_expand_conv (Conv2D) | (None, 64, 64, 480) | 38400 | block4c_add[0][0] |
| block5a_expand_bn (BatchNormalization) | (None, 64, 64, 480) | 1920 | block5a_expand_conv[0][0] |
| block5a_expand_activation (Activation) | (None, 64, 64, 480) | 0 | block5a_expand_bn[0][0] |
| block5a_dwconv (DepthwiseConv2D) | (None, 64, 64, 480) | 12000 | block5a_expand_activation[0][0] |
| block5a_bn (BatchNormalization) | (None, 64, 64, 480) | 1920 | block5a_dwconv[0] [0] |
| block5a_activation (Activation) | (None, 64, 64, 480) | 0 | block5a_bn[0][0] |
| block5a_se_squeeze (GlobalAveragePooling2D) | (None, 480) | 0 | block5a_activation[0][0] |
| block5a_se_reshape (Reshape) | (None, 1, 1,480) | 0 | block5a_se_squeeze[0][0] |
| block5a_se_reduce (Conv2D) | (None, 1, 1, 20) | 9620 | block5a_se_reshape[0][0] |
| block5a_se_expand (Conv2D) | (None, 1, 1, 480) | 10080 | block5a_se_reduce[0][0] |
| block5a_se_excite (Multiply) | (None, 64, 64, 480) | 0 | block5a_activation[0][0] block5a se_expand[0][0] |
| block5a_project_conv (Conv2D) | (None, 64, 64, 112) | 53760 | block5a_se_excite[0][0] |
| block5a_project_bn (BatchNormalization) | (None, 64, 64, 112) | 448 | block5a_project_conv[0][0] |
| block5b_expand_conv (Conv2D) | (None, 64, 64, 672) | 75264 | block5a_project_bn[0][0] |
| block5b_expand_bn (BatchNormalization) | (None, 64, 64, 672) | 2688 | block5b_expand_conv[0] [0] |
| block5b_expand_activation (Activation) | (None, 64, 64, 672) | 0 | block5b_expand_bn[0][0] |
| block5b_dwconv (DepthwiseConv2D) | (None, 64, 64, 672) | 16800 | block5b_expand_activation[0][0] |
| block5b_bn (BatchNormalization) | (None, 64, 64, 672) | 2688 | block5b_dwconv[0] [0] |
| block5b_activation (Activation) | (None, 64, 64, 672) | 0 | block5b_bn[0][0] |

-continued

Model: "model_1"

| Layer (type) | Output Shape | Param # | Connected to |
|---|---|---|---|
| block5b_se_squeeze (GlobalAveragePooling2D) | (None, 672) | 0 | block5b_activation[0][0] |
| block5b_se_reshape (Reshape) | (None, 1, 1,672) | 0 | block5b_se_squeeze[0][0] |
| block5b_se_reduce (Conv2D) | (None, 1, 1,28) | 18844 | block5b_se_reshape[0][0] |
| block5b_se_expand (Conv2D) | (None, 1, 1,672) | 19488 | block5b_se_reduce[0][0] |
| block5b_se_excite (Multiply) | (None, 64, 64, 672) | 0 | block5b_activation[0][0] block5b_se_expand[0][0] |
| block5b_project_conv (Conv2D) | (None, 64, 64, 112) | 75264 | block5b_se_excite [0] [0] |
| block5b_project_bn (BatchNormalization) | (None, 64, 64, 112) | 448 | block5b_project_conv[0][0] |
| block5b_drop (FixedDropout) | (None, 64, 64, 112) | 0 | block5b_project_bn[0][0] |
| block5b_add (Add) | (None, 64, 64, 112) | 0 | block5b_drop[0][0] block5a_project_bn[0][0] |
| block5c_expand_conv (Conv2D) | (None, 64, 64, 672) | 75264 | block5b_add[0][0] |
| block5c_expand_bn (BatchNormalization) | (None, 64, 64, 672) | 2688 | block5c_expand_conv[0][0] |
| block5c_expand_activation (Activation) | (None, 64, 64, 672) | 0 | block5c_expand_bn[0][0] |
| block5c_dwconv (DepthwiseConv2D) | (None, 64, 64, 672) | 16800 | block5c_expand_activation[0][0] |
| block5c_bn (BatchNormalization) | (None, 64, 64, 672) | 2688 | block5c_dwconv[0][0] |
| block5c_activation (Activation) | (None, 64, 64, 672) | 0 | block5c_bn[0][0] |
| block5c_se_squeeze (GlobalAveragePooling2D) | (None, 672) | 0 | block5c_activation[0][0] |
| block5c_se_reshape (Reshape) | (None, 1, 1,672) | 0 | block5c_se_squeeze[0][0] |
| block5c_se_reduce (Conv2D) | (None, 1, 1,28) | 18844 | block5c_se_reshape[0][0] |
| block5c_se_expand (Conv2D) | (None, 1,1,672) | 19488 | block5c_se_reduce[0][0] |
| block5c_se_excite (Multiply) | (None, 64, 64, 672) | 0 | block5c_activation[0][0] block5c_se_expand[0][0] |
| block5c_project_conv (Conv2D) | (None, 64, 64, 112) | 75264 | block5c_se_excite[0][0] |
| block5c_project_bn (BatchNormalization) | (None, 64, 64, 112) | 448 | block5c_project_conv[0][0] |
| block5c_drop (FixedDropout) | (None, 64, 64, 112) | 0 | block5c_project_bn[0][0] |
| block5c_add (Add) | (None, 64, 64, 112) | 0 | block5c_drop[0][0] block5b_add[0][0] |
| block6a_expand_conv (Conv2D) | (None, 64, 64, 672) | 75264 | block5c_add[0][0] |
| block6a_expand_bn (BatchNormalization) | (None, 64, 64, 672) | 2688 | block6a_expand_conv[0][0] |
| block6a_expand_activation (Activation) | (None, 64, 64, 672) | 0 | block6a_expand_bn[0][0] |
| block6a_dwconv (DepthwiseConv2D) | (None, 32, 32, 672) | 16800 | block6a_expand_activation[0][0] |
| block6a_bn (BatchNormalization) | (None, 32, 32, 672) | 2688 | block6a_dwconv[0] [0] |
| block6a_activation (Activation) | (None, 32, 32, 672) | 0 | block6a_bn[0][0] |
| block6a_se_squeeze (GlobalAveragePooling2D) | (None, 672) | 0 | block6a_activation[0][0] |
| block6a_se_reshape (Reshape) | (None, 1, 1,672) | 0 | block6a_se_squeeze[0][0] |
| block6a_se_reduce (Conv2D) | (None, 1, 1,28) | 18844 | block6a_se_reshape[0][0] |
| block6a_se_expand (Conv2D) | (None, 1, 1,672) | 19488 | block6a_se_reduce[0][0] |
| block6a_se_excite (Multiply) | (None, 32, 32, 672) | 0 | block6a_activation[0][0] block6a_se_expand[0][0] |
| block6a_project_conv (Conv2D) | (None, 32, 32, 192) | 129024 | block6a_se_excite[0][0] |
| block6a_project_bn (BatchNormalization) | (None, 32, 32, 192) | 768 | block6a_project_conv[0][0] |
| block6b_expand_conv (Conv2D) | (None, 32, 32, 1152) | 221184 | block6a_project_bn[0][0] |
| block6b_expand_bn (BatchNormalization) | (None, 32, 32, 1152) | 4608 | block6b_expand_conv[0] [0] |
| block6b_expand_activation (Activation) | (None, 32, 32, 1152) | 0 | block6b_expand_bn[0][0] |
| block6b_dwconv (DepthwiseConv2D) | (None, 32, 32, 1152) | 28800 | block6b_expand_activation[0][0] |
| block6b_bn (BatchNormalization) | (None, 32, 32, 1152) | 4608 | block6b_dwconv[0][0] |
| block6b_activation (Activation) | (None, 32, 32, 1152) | 0 | block6b_bn[0][0] |
| block6b_se_squeeze (GlobalAveragePooling2D) | (None, 1152) | 0 | block6b_activation[0][0] |
| block6b_se_reshape (Reshape) | (None, 1, 1, 1152) | 0 | block6b_se_sgueeze[0][0] |
| block6b_se_reduce (Conv2D) | (None, 1, 1,48) | 55344 | block6b_se_reshape[0][0] |
| block6b_se_expand (Conv2D) | (None, 1, 1, 1152) | 56448 | block6b_se_reduce[0][0] |
| block6b_se_excite (Multiply) | (None, 32, 32, 1152) | 0 | block6b_activation[0][0] block6b_se_expand[0][0] |
| block6b_project_conv (Conv2D) | (None, 32, 32, 192) | 221184 | block6b_se_excite [0] [0] |

-continued

Model: "model_1"

| Layer (type) | Output Shape | Param # | Connected to |
|---|---|---|---|
| block6b_project_bn (BatchNormalization) | (None, 32, 32, 192) | 768 | block6b_project_conv[0][0] |
| block6b_drop (FixedDropout) | (None, 32, 32, 192) | 0 | block6b_project_bn[0][0] |
| block6b_add (Add) | (None, 32, 32, 192) | 0 | block6b_drop[0][0] block6a_project_bn[0][0] |
| block6c_expand_conv (Conv2D) | (None, 32, 32, 1152) | 221184 | block6b_add[0][0] |
| block6c_expand_bn (BatchNormalization) | (None, 32, 32, 1152) | 4608 | block6c_expand_conv[0][0] |
| block6c_expand_activation (Activation) | (None, 32, 32, 1152) | 0 | block6c_expand_bn [0] [0] |
| block6c_dwconv (DepthwiseConv2D) | (None, 32, 32, 1152) | 28800 | block6c_expand_activation[0][0] |
| block6c_bn (BatchNormalization) | (None, 32, 32, 1152) | 4608 | block6c_dwconv[0][0] |
| block6c_activation (Activation) | (None, 32, 32, 1152) | 0 | block6c_bn[0][0] |
| block6c_se_sgueeze (GlobalAveragePooling2D) | (None, 1152) | 0 | block6c_activation[0][0] |
| block6c_se_reshape (Reshape) | (None, 1, 1, 1152) | 0 | block6c_se_sgueeze[0][0] |
| block6c_se_reduce (Conv2D) | (None, 1, 1,48) | 55344 | block6c_se_reshape[0][0] |
| block6c_se_expand (Conv2D) | (None, 1, 1, 1152) | 56448 | block6c_se_reduce[0][0] |
| block6c_se_excite (Multiply) | (None, 32, 32, 1152) | 0 | block6c_activation[0][0] block6c_se_expand[0][0] |
| block6c_project_conv (Conv2D) | (None, 32, 32, 192) | 221184 | block6c_se_excite[0][0] |
| block6c_project_bn (BatchNormalization) | (None, 32, 32, 192) | 768 | block6c_project_conv[0][0] |
| block6c_drop (FixedDropout) | (None, 32, 32, 192) | 0 | block6c_project_bn[0][0] |
| block6c_add (Add) | (None, 32, 32, 192) | 0 | block6c_drop[0][0] block6b_add[0][0] |
| block6d_expand_conv (Conv2D) | (None, 32, 32, 1152) | 221184 | block6c_add[0][0] |
| block6d_expand_bn (BatchNormalization) | (None, 32, 32, 1152) | 4608 | block6d_expand_conv[0] [0] |
| block6d_expand_activation (Activation) | (None, 32, 32, 1152) | 0 | block6d_expand_bn [0] [0] |
| block6d_dwconv (DepthwiseConv2D) | (None, 32, 32, 1152) | 28800 | block6d_expand_activation[0][0] |
| block6d_bn (BatchNormalization) | (None, 32, 32, 1152) | 4608 | block6d_dwconv[0][0] |
| block6d_activation (Activation) | (None, 32, 32, 1152) | 0 | block6d_bn[0][0] |
| block6d_se_sgueeze (GlobalAveragePooling2D) | (None, 1152) | 0 | block6d_activation[0][0] |
| block6d_se_reshape (Reshape) | (None, 1, 1, 1152) | 0 | block6d_se_sgueeze[0][0] |
| block6d_se_reduce (Conv2D) | (None, 1, 1,48) | 55344 | block6d_se_reshape[0][0] |
| block6d_se_expand (Conv2D) | (None, 1, 1, 1152) | 56448 | block6d_se_reduce[0][0] |
| block6d_se_excite (Multiply) | (None, 32, 32, 1152) | 0 | block6d_activation[0][0] block6d_se_expand[0][0] |
| block6d_project_conv (Conv2D) | (None, 32, 32, 192) | 221184 | block6d_se_excite[0][0] |
| block6d_project_bn (BatchNormalization) | (None, 32, 32, 192) | 768 | block6d_project_conv[0][0] |
| block6d_drop (FixedDropout) | (None, 32, 32, 192) | 0 | block6d_project_bn[0][0] |
| block6d_add (Add) | (None, 32, 32, 192) | 0 | block6d_drop[0][0] block6c_add[0][0] |
| block7a_expand_conv (Conv2D) | (None, 32, 32, 1152) | 221184 | block6d_add[0][0] |
| block7a_expand_bn (BatchNormalization) | (None, 32, 32, 1152) | 4608 | block7a_expand_conv[0] [0] |
| block7a_expand_activation (Activation) | (None, 32, 32, 1152) | 0 | block7a_expand_bn [0] [0] |
| block7a_dwconv (DepthwiseConv2D) | (None, 32, 32, 1152) | 10368 | block7a_expand_activatlon[0][0] |
| block7a_bn (BatchNormalization) | (None, 32, 32, 1152) | 4608 | block7a_dwconv[0][0] |
| block7a_activation (Activation) | (None, 32, 32, 1152) | 0 | block7a_bn[0][0] |
| block7a_se_squeeze (GlobalAveragePooling2D) | (None, 1152) | 0 | block7a_activation[0][0] |
| block7a_se_reshape (Reshape) | (None, 1, 1, 1152) | 0 | block7a_se_squeeze[0][0] |
| block7a_se_reduce (Conv2D) | (None, 1, 1,48) | 55344 | block7a_se_reshape[0][0] |
| block7a_se_expand (Conv2D) | (None, 1, 1, 1152) | 56448 | block7a_se_reduce[0][0] |
| block7a_se_excite (Multiply) | (None, 32, 32, 1152) | 0 | block7a_se_expand[0][0] |
| block7a_project_conv (Conv2D) | (None, 32, 32, 320) | 368640 | block7a_se_excite [0] [0] |
| block7a_project_bn (BatchNormalization) | (None, 32, 32, 320) | 1280 | block7a_project_conv[0][0] |
| top_conv (Conv2D) | (None, 32, 32, 1280) | 409600 | block7a_project_bn[0][0] |
| top_bn (BatchNormalization) | (None, 32, 32, 1280) | 5120 | top_conv[0][0] |
| top_activation (Activation) | (None, 32, 32, 1280) | 0 | top_bn[0][0] |
| decoder_stage0a_transpose (Conv2DTranspose) | (None, 64, 64, 64) | 1310720 | top_activation[0][0] |

-continued

| Model: "model_1" | | | |
|---|---|---|---|
| Layer (type) | Output Shape | Param # | Connected to |
| decoder_stage0a_bn (BatchNormalization) | (None, 64, 64, 64) | 256 | decoder_stage0a_transpose[0][0] |
| decoder_stage0a_relu (Activation) | (None, 64, 64, 64) | 0 | decoder_stage0a_bn[0][0] |
| decoder_stage0_concat (Concatenate) | (None, 64, 64, 736) | 0 | decoder_stage0a_relu[0][0] block6a_expand_activation[0][0] |
| decoder_stage0b_conv (Conv2D) | (None, 64, 64, 64) | 423936 | decoder_stage0_concat[0][0] |
| decoder_stage0b_bn (BatchNormalization) | (None, 64, 64, 64) | 256 | decoder_stage0b_conv[0][0] |
| decoder_stage0b_relu (Activation) | (None, 64, 64, 64) | 0 | decoder_stage0b_bn[0][0] |
| decoder_stage1a_transpose (Conv2DTranspose) | (None, 128, 128, 64) | 65536 | decoder_stage0b_relu[0][0] |
| decoder_stage1a_bn (BatchNormalization) | (None, 128, 128, 64) | 256 | decoder_stage1a_transpose[0][0] |
| decoder_stage1a_relu (Activation) | (None, 128, 128, 64) | 0 | decoder_stage1a_bn[0][0] |
| decoder_stage1_concat (Concatenate) | (None, 128, 128, 304) | 0 | decoder_stage1a_relu[0][0] block4a_expand_activation[0][0] |
| decoder_stage1b_conv (Conv2D) | (None, 128, 128, 64) | 175104 | decoder_stage1_concat[0][0] |
| decoder_stage1b_bn (BatchNormalization) | (None, 128, 128, 64) | 256 | decoder_stage1b_conv[0][0] |
| decoder_stage1b_relu (Activation) | (None, 128, 128, 64) | 0 | decoder_stage1b_bn[0][0] |
| decoder_stage2a_transpose (Conv2DTranspose) | (None, 256, 256, 64) | 65536 | decoder_stage1b_relu [0] [0] |
| decoder_stage2a_bn (BatchNormalization) | (None, 256, 256, 64) | 256 | decoder_stage2a_transpose[0][0] |
| decoder_stage2a_relu (Activation) | (None, 256, 256, 64) | 0 | decoder_stage2a_bn[0][0] |
| decoder_stage2_concat (Concatenate) | (None, 256, 256, 208) | 0 | decoder_stage2a_relu[0][0] block3a_expand_activation[0][0] |
| decoder_stage2b_conv (Conv2D) | (None, 256, 256, 64) | 119808 | decoder_stage2_concat [0] [0] |
| decoder_stage2b_bn (BatchNormalization) | (None, 256, 256, 64) | 256 | decoder_stage2b_conv[0][0] |
| decoder_stage2b_relu (Activation) | (None, 256, 256, 64) | 0 | decoder_stage2b_bn[0][0] |
| decoder_stage3a_transpose (Conv2DTranspose) | (None, 512, 512, 64) | 65536 | decoder_stage2b_relu[0][0] |
| decoder_stage3a_bn (BatchNormalization) | (None, 512, 512, 64) | 256 | decoder_stage3a_transpose[0][0] |
| decoder_stage3a_relu (Activation) | (None, 512, 512, 64) | 0 | decoder_stage3a_bn[0][0] |
| decoder_stage3_concat (Concatenate) | (None, 512, 512, 160) | 0 | decoder_stage3a_relu[0][0] block2a_expand_activation[0][0] |
| decoder_stage3b_conv (Conv2D) | (None, 512, 512, 64) | 92160 | decoder_stage3_concat[0][0] |
| decoder_stage3b_bn (BatchNormalization) | (None, 512, 512, 64) | 256 | decoder_stage3b_conv[0][0] |
| decoder_stage3b_relu (Activation) | (None, 512, 512, 64) | 0 | decoder_stage3b_bn[0][0] |
| final_conv (Conv2D) | (None, 512, 512, 16) | 9232 | decoder_stage3b_relu[0][0] |
| activation (Activation) | (None, 512, 512, 16) | 0 | final_conv[0][0] |

Total params: 6,378,604
Trainable params: 6,335,564
Non-trainable params: 43,040

The Vision Attributes model 402 comprises a further CNN component 404, and a fully connected layer 406 producing a feature vector 408 that predicts the likelihood of an input image 204 being anterior-posterior (AP), posterior-anterior (PA), lateral (LAT) or 'other', where 'other' includes non-CXR images as well as CXR images which are not AP, PA or LAT. Advantageously, the Vision Attributes model 402 predicts whether the image is a recognised CXR view position and, if so, which one. The Vision Attributes model 402 may thus be used to detect and filter out x-ray images which are not represented in the training/validation datasets for the Vision Classification and Vision Segmentation models 200/300. The Vision Attributes model therefore improves the likelihood that the input images 204 input to the Vision Classification model 200 and the Vision Segmentation model 300 are well-represented by the models and can produce accurate predictions.

Using combined classification and segmentation models 200/300 may be advantageous, compared to the use of two separate CNN components for vision classification and segmentation. Firstly, the use of a combined network is computationally faster, as there is no need to re-feed the input images 204 through the same encoder backbone common to both classification and segmentation. Secondly, this combined network implementation may provide improved performance as training a single model means classifications for findings have an additional training signal through segmentation maps that contribute to its learning. Conversely segmentation maps would have an additional training signal through classification labels. Thirdly, a combined model may have a less complex train/release cycle and improved resilience to hidden stratification because of the features above. Instead of gating by the result of the classification training to decide what is trained for segmentation (i.e. performing the steps of training the classification model, evaluating the classification model, generating heatmaps, then training the segmentation mode), a combined model is trained all at once then evaluated (i.e. a model that does classification and segmentation is trained in one step, then evaluated).

Preferably, the number of input images 204 that can be used by a combined model (or individual segmentation and classification models) can range from one image to an arbitrary number of images. This may be advantageous in that it saves computation time for studies with fewer than N images (where N is a fixed number expected by a model that is not able to take as input any number of images), because there is no need to pass N images through the model, e.g. just one or two images. Additionally, this may provide increased accuracy for studies with greater than N images, because it is possible to pass additional images and obtain more information from the study.

Each of the CNN components 200/300, 402 may include a plurality of CNNs (i.e. an ensemble of models) that have each been independently trained. The outputs of these individual CNNs can be combined into an output prediction. For example, the classification feature vector 210 values output by each Vision Classification model in the ensemble can be combined, e.g. into an average score, for each radiological finding. Similarly, the attributes feature vector 408 values output by each Vision Attributes model in the ensemble can be combined, e.g. into an average score, which can be used to determine the most likely orientation class for an image. Ensembling advantageously results in higher prediction accuracy, particularly when less training data is available. Models can be trained and run in parallel, for improved efficiency of prediction.

Visual Findings Classification

In embodiments of the invention, a set of possible visual findings may be determined according to an ontology tree as depicted in Table 1 or Table 2. These may be organised into a hierarchical structure or nested structure. Sublevels in a hierarchical ontology tree may be combined into more generalised findings (e.g. pneumothorax being the parent class of simple pneumothorax and tension pneumothorax). The generalised findings may be depicted as generic higher levels. The generalised findings are also evaluated as radiological findings in their own right. Exemplary visual radiological findings for CXR images include those listed in Table 1 or Table 2. The use of a hierarchical structure for the set of visual findings may lead to an improved accuracy of prediction as various levels of granularity of findings can be simultaneously captured, with increasing confidence when going up the hierarchical structure.

The CXR finding ontology tree depicted in Table 1 was developed by a consensus of three Australian radiologists, including at least one subspecialty thoracic radiologist.

Preparation of Training Data

For the purpose of training models in embodiments directed to analysis of CXR images (pixel data) for classifying x-ray imagery as frontal, lateral or other x-ray imagery, a dataset of x-ray images may be used. A sub-dataset consisting solely of anatomical CXR images is preferably used for radiological findings. Each set of anatomical images may include two or more images of a body portion of the respective subject depicting a respective different orientation of at least the body portion of subject. Each of the CXR images is an anatomical x-ray image of a human being's chest associated with a set of labels (suitably, one for each of the 188 radiological findings configured to be detectable by the Vision model 400) manually annotated by expert radiologists for example using a chest x-ray software labelling tool. In one embodiment, 127 child findings are annotated by expert radiologists. The remaining 61 parent findings are computed by evaluating the logical relationships in Table 1. Further hidden stratification labels are computed by additionally evaluating Table 2. Each label indicates whether a particular radiological finding was identified by one or more expert reviewers. A label derived from a plurality of expert reviews may be obtained via algorithms that quantify the performance and/or uncertainty of independent reviews combined, e.g. using a vote aggregation algorithm, for example, the Dawid-Skene algorithm. These labels can then be used to train a deep neural network for findings within CXR images.

In some embodiments, ethnic, gender and age diverse data are collated from various sources including, for example, open source/publicly available datasets, commercial datasets and a proprietary dataset. These then comprise the training datasets to train the deep learning models. It is advantageous to use multiple datasets to reduce the risk of markers and other biases that can be incorporated into the model from a single dataset. After the collected data is de-identified (if applicable) to comply with privacy laws, the de-identified data is labelled by three independent radiologists according to the ontology tree of Table 1, depending on whether a particular disease, abnormality or injury is present in a CXR image. The Dawid-Skene algorithm is used to generate an estimated probability that each finding is present in the image given three labels assigned by the three independent certified radiologists. The estimated probability is used as a training target for the deep learning models.

In a particular embodiment, CXR images used for the training dataset were procured from multiple sources such as publicly available datasets.

Inclusion criteria for the training dataset were: age greater than 16 years; and at least one frontal CXR. Selected cases were from inpatient, outpatient and emergency settings. Data from all sources was de-identified. DICOM tags were removed. Protected health information was removed from reports and images through an automated de-identification process. Image data was preserved at the original resolution and bit-depth. Patient IDs and Study IDs were anonymised to de-identify them while retaining the temporal and logical association between studies and patients. The resulting dataset comprises 821,681 CXR images. The median number of model training cases per clinical/radiological finding in this dataset is 5,427.

All participants in the labelling and evaluation phases were trained to identify the CXR radiological findings according to the ontology tree shown in Table 1.

Each of the 821,681 CXR images was independently labelled by three radiologists randomly selected from a pool of 120 radiologists. Clinical reports, age, and sex were provided, along with frontal and lateral CXR images. Each finding was assigned a binary 'present' or 'absent' label. The consensus for each finding for each triple-read study was generated as a consensus score between 0 and 1 using the Dawid-Skene algorithm, which takes into account the relative accuracies of each labeller for each finding. Segmentation overlay maps were generated for the consensus findings by a single radiologist to locate relevant localise and depict the pathology.

In preparation for use with vision models embodying the invention, CXR images are rescaled such that the largest side is 1280 pixels. No changes in aspect ratio and no letterboxing are performed. If the largest side is smaller than 1280 pixels, no change is performed. The CXR images are stored as suitable JPEG format images (e.g. 8 bit, 1 channel, 95% compression ratio). Labels are stored separately to input data, and tracked with version control for the data training pipeline. The ontology tree (Table 1) is stored separately in a flat and/or hierarchical structure (e.g. class_1; class_1a; class1aa; class2; class 3; class_3a; class_3b; etc). The separation of the CXR images, labels and ontology tree avoids data duplication and enables easier maintenance, increases re-usability/upgradeability, automation tasks applicable for each data type, and improves identification of errors of each data type.

Binary masks representing the segmentation overlay maps identifying the locations of radiological findings are stored in PNG format (1-channel, 8-bit), one per finding per image. Class indices are assigned according to the order of labels in the ontology tree file. Where hierarchal, class indices are based on depth-first order on the leaves. For instance, in the above example, there is class_1aa, class_1ab, class_1b, class_2, class_3a, class_3b.

There are two types of label, namely classification and segmentation labels. Classification labels are stored in a gzip-compressed Comma-Separated Values (CSV) file in which rows correspond to unique images, and columns consist of a key (one of PatientID, StudyInstanceUID, SeriesInstanceUID or SOPInstanceUID, as stored in the original DICOM image), as well as a column for each classification label. The label columns are ordered as per the ontology tree (Table 1). Each value comprises a probability of the corresponding finding being in the image, within a range of [0, 1], and are derived from the radiologist labels (e.g. using the Dawid-Skene algorithm) or any other source of ground truth information. Where a class has not been labelled for an image, no value is present.

Finding Correlation and Negation Pairs

In embodiments of the invention, when preparing training data for the Vision Classification model 200, a matrix of correlation between each of the, e.g., 188 radiological findings is computed for the whole training and testing dataset. The correlation matrix is used because it is purposely enriching the testing dataset, by selecting cases with anomalies in the radiological findings (the rare data). To minimise the size of the test set required, cases are selected with multiple findings.

For example, when detecting pneumothoraces, the correlation matrix provides feedback on how confident the detection of the two classes of pneumothoraces (simple & tension) truly is from the carefully designed ontology tree. This avoids the Vision Classification model becoming, for example, a chest tube detector masquerading as a pneumothorax detector unbeknownst to its users such as clinicians in emergency departments or radiologists.

Looking at the correlation matrix, the testing dataset must avoid having excessive correlations as compared to the training dataset. When selecting a minimum viable dataset it is desirable to avoid picking, for example, all the cases of pneumothorax that also have the presence of a chest tube, since this may result in a model trained to recognize, for example, chest tube features as pneumothorax features such that pneumothoraces may be predicted in an image when only chest tubes are present.

The correlation matrix informs what to include in the training and testing datasets. It also enables to put in some key studies in the testing dataset that ensure the Vision classification model can detect pneumothorax separately from the presence of a chest tube or other combination of radiological findings in a CXR image. During testing dataset generation, this is monitored and there is a comparison of the testing dataset to the full dataset. If the comparison shows the correlation between any pairs of findings becomes too high, the selection of testing data that includes too many of those pairs (pair of findings) is prevented. In the event of deviation by more than 20% of the original correlation, and the correlation itself is higher than 0.8, the logic for selection of the training dataset may be changed.

Furthermore, in order to improve the performance of the deep learning models, particularly in relation to radiological findings that are naturally highly correlated with each other, the performance of the deep learning model is computed in detection of negation pairs. Accordingly, a subtask of {finding_a}_no_{finding_b} creates a negation pair for 'pneumothorax':

negation_pair=[('pneumothorax', 'subcutaneous_emphysema'), ('pneumothorax', 'intercostal_drain'), ('pneumothorax', 'tracheal_deviation')]

In this example, the first line equates to pneumothorax_no_subcutaneous_emphysema, meaning a pneumothorax is present but subcutaneous emphysema is not. The quantity of data in each of the above three following negation pairs are at least 1000 for each pair.

In prior art models (e.g. Laserson, J., Lantsman, C. D., Cohen-Sfady, M., Tamir, I., Goz, E., Brestel, C., Bar, S., Atar, M., and Elnekave, E., *TextRay: Mining Clinical Reports to Gain a Broad Understanding of Chest X-Rays*. arXiv:1806.02121 [cs.CV] (2018)), it would not be known if their model is detecting subcutaneous emphysema, but then reporting that it finds pneumothorax. In this case, the intended pneumothorax detector of Laserson's model is possibly a subcutaneous_emphysema detector or possibly an intercostal_drain detector or possibly an tracheal_deviation detector. This prior art example used natural language processing (i.e. regular expressions) to mine clinical text reports that mention the word 'pneumothorax', but the small quantity of reports analysed by Laserson could also show the presence of subcutaneous_emphysema, intercostal_drain or tracheal_deviation, because these are commonly reported together with pneumothoraces.

In contrast and advantageously, a Vision Classification model embodying the present invention can discriminate between pneumothoraces with and without subcutaneous emphysema. Such models are better at detecting pneumothoraces, rather than actually detecting a different radiological finding that is associated with pneumothoraces due to sub-stratification training of the deep learning model(s).

Further negation pairs exemplifying combined findings that can be tracked in order to identify a best performing model are listed in Table 3.

Model Training

A 5-fold cross-validation approach was used to train each of the Vision Classification and Segmentation, and Vision Attributes models 200/300, 402 and can estimate and evaluate the inferencing performance of the model on unseen images. This approach consists of separating the training and validation dataset into five 'folds', where each fold consists of an equal number of randomly assigned input images 204 without the primary key (for example, patient ID) being in multiple folds to avoid data leakage. Five models were trained per project, one for each fold being the validation set (and the remaining folds being the training set), and later ensembled and postprocessed.

In a particular embodiment, the Vision Classification model 200 takes at least one, and preferably three, input images 204 of a CXR study and predicts the confidence score for each radiological finding out of 188 radiological findings. The Vision Classification model 200 input consists of batches of three input images (AP, PA or LAT views) as determined by the Vision Attributes model 402. In another embodiment, the input may be batched by size of study, from one to four images 204 at training time. The output comprises a predicted confidence score that each radiological finding is present in at least one of the three images 204.

In this embodiment, the model architecture of the Vision Classification model 200 is as follows.

- An EfficientNetB0 backbone is used for feature extraction. Global Average Pooling and Global Max Pooling layers are added to the top level activation feature map from the EfficientNetB0 backbone and the outputs are concatenated.
- The input images 204 are processed per CXR study using a shared weight EfficientNetB0 backbone as described above, and the maximum feature is taken across the last axis.
- A dense layer corresponding with the number of findings (i.e. 188 output elements) is added with sigmoid activation function to produce a multi-label classification output.
- Rather than ReLU which nullifies negative values (and thus derivatives are zero for all negative values), a Swish activation is used to achieve more accuracy. Swish is a multiplication of a linear and a sigmoid activation.
- Squeeze-and-excitation (SE) optimisation is added to provide further improvement to performance. It gives weightage to each channel instead of treating them all equally.

The EfficientNetB0 architecture was hyperparameterized to enable model optimisation. Model hyperparameters are the properties that govern the entire training process of a deep learning model. They directly control the behaviour of the training algorithm and have a significant impact on the performance of the model that is being trained. Advantages of selecting optimal hyperparameters include efficiently search the space of possible hyperparameters and easy to manage a large set of experiments for hyperparameter tuning. The hyperparameter variables include: learning rate, number of epochs, hidden layers, hidden units, and activations functions. Hyperparameter optimisation can be performed by several algorithms including: grid search, random search or Bayesian optimisation.

The Vision Classification model 200 was trained using gradient descent to minimise the focal loss function. The Vision Classification model 200 was trained using a progressive resolution growth training procedure initially at 512×512 resolution. The Vision Classification model 200 was subsequently re-trained with the final resolution of 1024×1024 to improve detection of small features that may be present in the input image 204. Batch sizes of 128 and 32 were used for spatial dimension resolutions of 512 and 1024 respectively.

The initial learning rate was set to 0.001 and a Cosine Decay with Restarts learning rate schedule used to aid model convergent speed and to improve generalisation to unseen data. A Rectified Adam (RAdam) optimiser is used to train the deep learning model which helps stabilise training during the initial period and prevent the deep learning model from making big jumps when it has not seen enough training examples.

To address the imbalanced nature of the dataset, class-balanced loss weighting is used with the beta parameters of 0.999. This helps scale up the loss for the minority class and scale down the loss of the majority class according to the effective number of positive cases. Loss scaling forces the deep learning model to pay more attention toward the minority classes. Class imbalance can cause initial biases to more common classes if not controlled, resulting in initial estimates of model weights being far from the actual distribution of predicted score for each class. The bias of the last dense layer is initialised such that the initial predicted probability is close to the actual prevalence of each class.

The estimated radiological finding probability generated via the Dawid-Skene algorithm is an estimated probability of the presence of each finding rather than a binary label. This is a better reflection of the likelihood of each finding and can be used as additional training signal for the deep learning model. As such the deep learning model is trained to minimise the difference between the predicted score compare to the David-Skene algorithm output directly.

To increase the effective size of the dataset and minimise overfitting, extensive data augmentation was used. For each input image 204 the following random transformations were used:

- Random flip left right (50% probability)
- Random image rotation (−45 to 45 degrees at 50% probability)
- Random zoom in/out (−10% to 10% at 50% probability)
- Random Translate (−10% to 10% vertically and horizontally at 50% probability)
- Random Brightness and Contrast (10% at 50% probability)
- Random image patch dropout (25% drop out rate at 50% probability)
- Random histogram equalisation (50% probability)

The dataset was cross-validated using the PatientID as the primary key to avoid data leakage of input images 204 from the same patient among each fold. The mean validation AUROC ('area under the receiver operating curve') and standard deviation were reported for each finding. During experimentation, models were compared to improve the macro AUROC (across all findings). The macro AUROC is used to determine the ensembled model performance and uncertainty for each finding by taking the mean and standard deviation across the five models.

In medical imaging there are many more unlabelled images than there are labelled. Noisy Student Training is a semi-supervised learning technique that is used to leverage this unlabelled data. The best 5-fold ensemble is used to generate predictions on all unlabelled CXR studies outside the test dataset. These predictions are assumed to be correct and are then used as labels (termed 'pseudo labels'). The entire training procedure is subsequently repeated from scratch where the pseudo-labelled data are mixed with the manual labelled data at 50% ratio during the training process. Note that pseudo-labelled data are not used for the validation or test sets. The same augmentations are applied during training. Noisy Student Training improves the performance of the deep learning model due to the ability to train with much more data and with greater variation, allowing for better generalization.

A matrix of correlation between each of the 188 radiological findings was computed for the whole training and validation dataset.

Figure 5A:
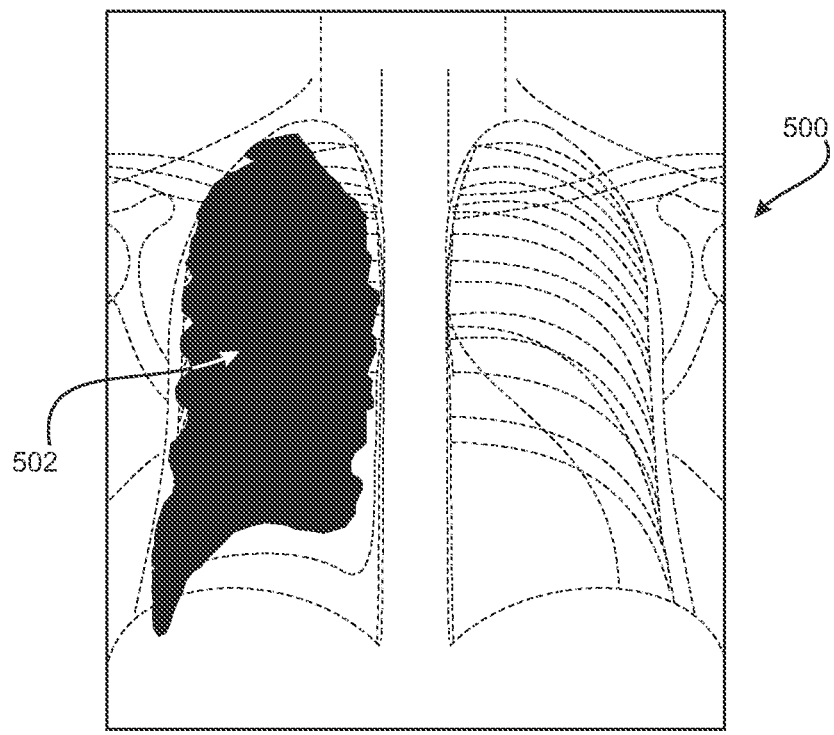
FIGS. 5A and 5B show examples of positional information provided by a vision segmentation model overlaid on medical images, according to embodiments of the invention.

The Vision Segmentation model 300 output 308, 310 of the Vision model 400 provides additional context and positional information for a subset of the radiological findings of the Vision Classification model 200. Predictions made by this deep learning model can be of one of the following forms:

MAP 308, as shown in FIG. 5A, comprises a segmentation mask/overlay 502 on top of one or more input images 500; and/or LATERALITY comprises a prediction of whether a finding is present in the left, right, or both (i.e. bilateral).

Figure 5B:
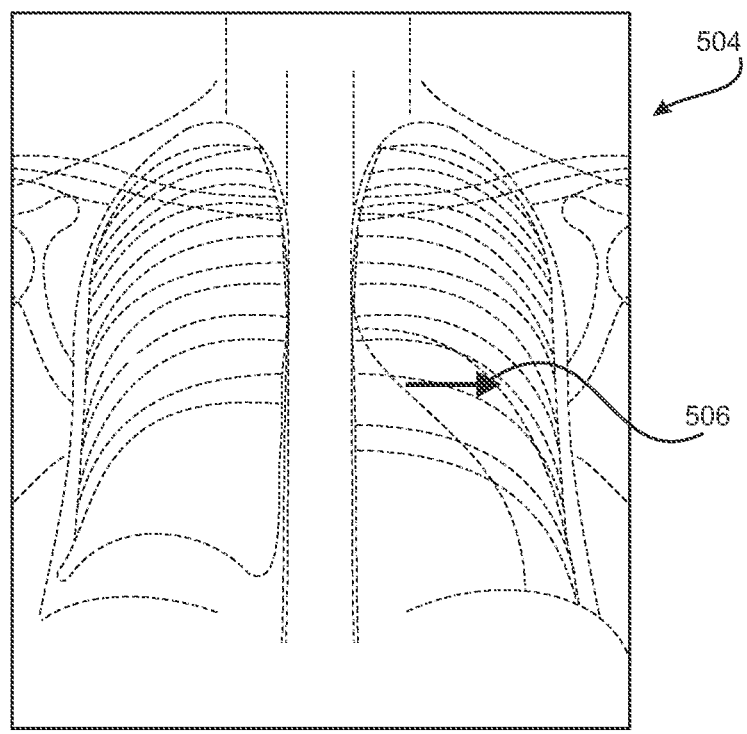
Figure 6A:
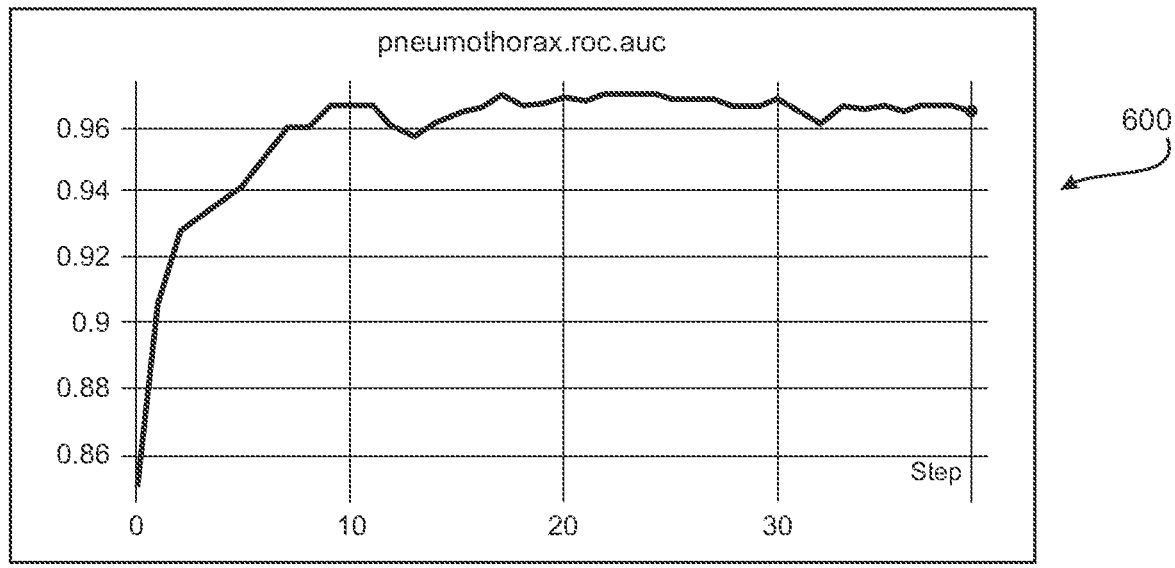
FIGS. 6A to 6D show exemplary performance results of trained medical image analysis models embodying the invention.
Figure 6B:
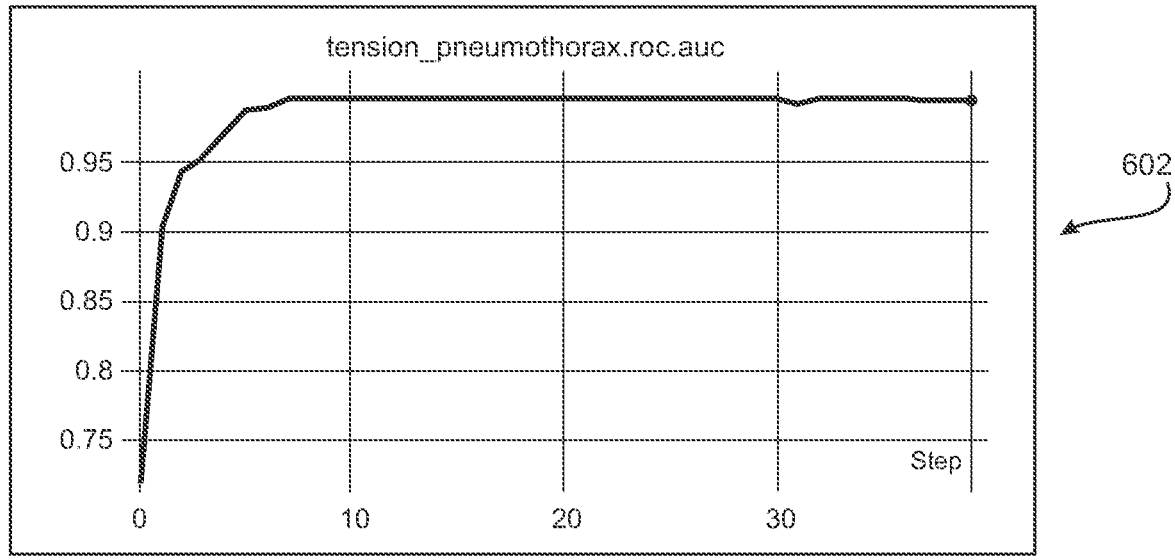
Figure 6C:
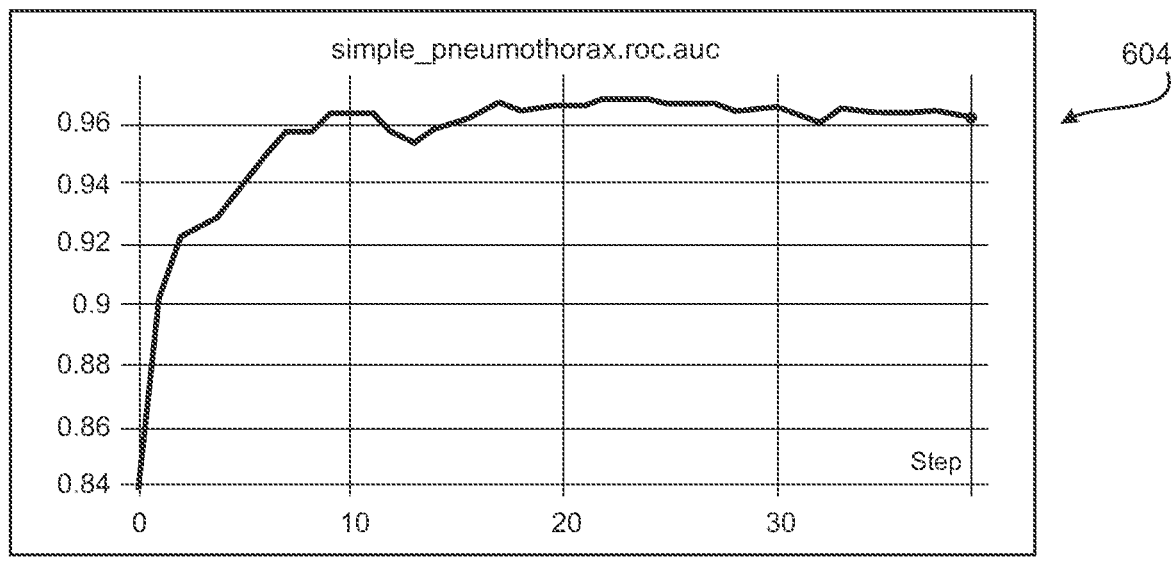
Figure 6D:
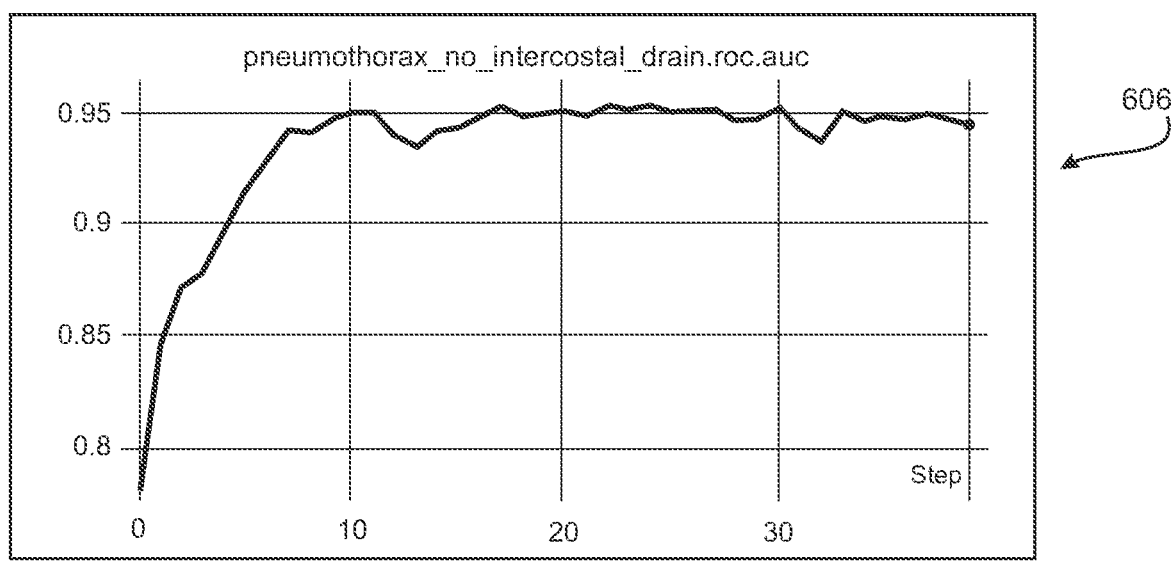

A LATERALITY prediction may be transformed into a MAP, as shown in FIG. 5B, in which one or more indications of laterality, e.g. 506, are overlaid on top of one or more input images 504. In some embodiments, for example, the intensity of each side of the image 504 may be determined by the probability of the finding being in the left or right of the image 504. Segmentation provides useful additional context to findings and is a requirement for some findings to be medically actionable.

The Vision Segmentation model 300 input consists of batches of single images (AP, PA or LAT views as determined by the Vision Attributes model 402). Images 204 are either up- or down-scaled, without letterboxing (i.e. with aspect-ratio distortion in cases where the initial aspect ratio differs from the target). Images 204 are scaled using the rescale slope and rescale intercept from DICOM header.

The model outputs 308, 310 are converted to a MAP represented as a losslessly compressed image string (for example, PNG data compression format) in order to reduce data storage and transmission requirements, and thus to reduce the time needed for a medical practitioner to use the model predictions. Further details of this approach to transmission data reduction are provided later in this specification.

For segmentation findings with a display type of MAP, the model 300 is trained and validated using labelled data through 5-fold cross validation. The findings of type MAP included: acute rib fracture segmentation; airspace opacity segmentation; humeral lesion segmentation; rib lesion segmentation; scapular lesion segmentation; clavicle lesion segmentation; spine lesion segmentation; collapse segmentation; effusion segmentation; cvc segmentation; ngt segmentation; internal foreign body segmentation; lesion segmentation; pleural mass segmentation; pneumothorax segmentation; and spine wedge fracture segmentation.

For segmentation findings with a display type of LATERALITY, radiologists were presented with cases labelled as positive for the corresponding classification finding by the Dawid Skene algorithm and instructed to indicate if the finding existed on the left, right or on both sides. Each localization case was only labelled by one radiologist. LATERALITY cases were only used for validation—they were not used in training the model. Instead, they were generated at inference time based on the weights learned in the classification and MAP segmentation training.

The findings of type LATERALITY included: acute clavicle fracture segmentation; acute humerus fracture segmentation; axillary clips segmentation; clavicle fixation segmentation;

diffuse airspace opacity segmentation; diffuse perihilar airspace opacity segmentation; diffuse lower airspace opacity segmentation; diffuse upper airspace opacity segmentation; intercostal drain segmentation; interstitial thickening diffuse segmentation; interstitial thickening lower segmentation; interstitial thickening upper segmentation; interstitial thickening volloss diffuse segmentation; interstitial thickening volloss upper segmentation; interstitial thickening volloss lower segmentation; lung collapse segmentation; lung resection volloss segmentation; miliary segmentation; neck clips segmentation; rib fixation segmentation; rotator cuff anchor segmentation; scapular fracture segmentation; shoulder dislocation segmentation; shoulder fixation segmentation; shoulder replacement segmentation; and subcutaneous emphysema segmentation.

The Vision Segmentation model 300 was trained using a gradient descent learning algorithm to minimise the focal loss function. The RAdam optimiser was used to train the deep learning models. The RAdam is an optimiser for image classification and helps stabilise training during the initial period to avoid big jumps in model weights when the model has not been exposed to sufficient training examples.

The dataset was cross-validated using the PatientID as the primary key to ensure no data leakage of images from the same patient amongst each of the five folds. Five deep learning models were trained to convergence on combinations of four of the five folds and validated on the fifth (hold-out) fold. For MAP, the maps were evaluated against the Dice score (i.e. the Dice coefficient is twice the Area of Overlap divided by the total number of pixels in both true and predicted masks). For laterality findings, the AUROC was evaluated. Both mean and standard deviation are reported for each metric and radiological finding.

A postprocessed layer is included in the model that returns a bar on the left and right of the image where the left value is the maximum pixel value of the left-hand side of the output mask (output of the sigmoid layer), and likewise for the right. This is used for LATERALITY to determine if certain findings are found on the left, right or both sides of the input image.

To generate a training dataset for the Vision Attributes model 402, the CXR view position was determined by the DICOM ViewPosition attribute for commercial and public datasets, while a DICOM metadata filtering was used for a proprietary dataset. For each dataset, images were filtered by grouping 'LL', 'RL', and 'LATERAL' as 'LAT' and removing input DICOM image files 204 that have an age attribute less than eight years.

For the proprietary dataset, the filtering process also included the following steps.

1. Creation of a blacklist of keywords to avoid (reasoning provided below).
   a. ENHANCED: Post-processed x-ray. Results in a variably altered image with less processable detail, which would hinder the model.
   b. EDGE: Post-processed x-ray. Results in a variably altered image with less processable detail, which would hinder the model.
   c. OBL: Rarer and more variable view of the chest. Likely insufficient training data.
   d. STERNUM: Limited chest view and with penetration optimised for bones and not for soft tissue.
   e. RIB: Limited chest view and with penetration optimised for bones and not for soft tissue.
   f. SCAPULA: Limited chest view with penetration optimised for bones and not for soft tissue.
   g. SPINE: Limited chest view with penetration optimised for bones and not for soft tissue.
   h. SHOULDER: Limited chest view with penetration optimised for bones and not for soft tissue.

i. CLAVICLE: Limited chest view with penetration optimised for bones and not for soft tissue.
j. AC JOINT: Limited chest view with penetration optimised for bones and not for soft tissue.
k. SC JOINT: Limited chest view with penetration optimised for bones and not for soft tissue.
l. APICAL: Limited chest view. Likely insufficient training data.
m. LORDOTIC: Rare and more variable view of the chest. Likely insufficient training data.
2. Checking that the following are all true.
   a. The modality header (Modality) is one of the following: 'CR'; 'DX';
   b. The body part examined header (BodyPartExamined) is either 'CHEST', 'PORT_CHEST' or is missing.
   c. Any of the following header rows contains 'CHEST' or is missing.
      i. StudyDescription,
      ii. SeriesDescription, or
      iii. ProtocolName.
   d. The view position is one of 'AP', 'PA', 'LATERAL', 'LL', 'RL', 'LAT', 'CHEST', 'CHEST PA' or is missing.
   e. The SeriesDescription contains any of the following keywords: 'CHEST', 'AP', 'PA', 'LAT', 'CXR', 'Thorax' or is missing.
   f. SeriesDescription does not contain any word from the blacklist defined in Step 1.
   g. The ProtocolName contains any of the following keywords: 'CHEST', 'PA', 'AP', 'LAT', 'CXR', 'RT', 'Thorax', 'Standalone', 'Skeletal Survey' and assume true if ProtocolName is missing.
   h. The ProtocolName does not contain any word from the blacklist defined in Step 1.
3. If all conditions in Step 2 are true, assume the x-ray is a CXR.
4. Relabel ViewPosition values 'LL', 'RL', 'LATERAL' with 'LAT'.
5. Relabel 'CHEST PA' with 'PA'.
6. If the image is a CXR (i.e. satisfies Step 3), relabel the ViewPosition to be 'AP', 'PA', 'LAT' based on if any of the following headers contain the keyword: SeriesDescription, ProtocolName, or ViewPosition.
7. Change any ViewPosition of 'CHEST' to be missing.
8. If the ViewPosition is not missing and is not in 'AP', 'PA', 'LAT' CXR, label it as OTHER.
9. Remove all images whose ViewPosition is missing after Steps 1-8 from the training/validation dataset.

In this embodiment, the model architecture for the Vision Attributes model 402 is as follows.

An EfficientNetB0 backbone is used for feature extraction. Global Average Pooling and Global Max Pooling layers are added to the top level activation feature map from the EfficientNetB0 backbone and the outputs are concatenated.

A Dense layer is added after a dropout layer of 0.25 probability with softmax activation function to produce multi-class classification output for classes AP, PA, LAT, OTHER.

After training, an ensemble of five versions of the same model (one for each of the five folds as the validation dataset) is used to improve generalisation. The deep learning models are merged at the output layer by taking the average confidence for each label. A final layer is added that returns only the probability of the class that has a probability greater than the threshold with the best F2-score for the class. The remaining class probabilities are converted to 0. If no class has a probability greater than the threshold, the image 204 is labelled as OTHER. If there are multiple that satisfy the condition, only one probability is returned, with OTHER>LAT>AP>PA being the prioritization.

Input to the Vision Attributes model 402 is an input DICOM image 204 to be assessed for view position, while the output was a feature vector 408 comprising relative probabilities that the input image 204 is one of four view positions (AP, PA, LAT, OTHER).

The Vision Attributes model 402 was trained using gradient descent to minimise the categorical cross-entropy function, and with a resolution of 256×256 (with batch size of 1024), or 128×128 (with batch size of 4096). The RAdam optimiser was used to train the deep learning model 402, with an initial learning rate set to 0.001 and a Cosine Decay with Restarts learning rate schedule used to aid in model convergence speed and to improve generalisation to unseen data. Label smoothing of 0.1 was also used.

The imbalanced nature of the dataset was accommodated for by random minority oversampling on the training set because it helps improve the AUROC score for CNNs. The bias of the last dense layer was initialised such that the initial predicted probability is close to the actual relative prevalence of each class.

To increase the effective size of the dataset and minimise overfitting, extensive data augmentation was used. For each input image 204, the following random transformation were used:

Random flip left right (50% probability)
(Optional Transform) Random flip up down (5% probability)
Random image rotation (−45 to 45 degrees or −10 to 10 degrees with bilinear interpolation; 50% probability)
(Optional Transform) Random zoom in/out (−10% to 10% and −10% to 10% respectively; 50% probability)
Random shear (−10% to 10% or −3% to 3%; 50% probability)
Random brightness (+/−10%)
Random contrast ([0.9, 1.1] magnifier; 50% probability)
Random image patch dropout (25 percentile patch dropout; 50% probability of occurrence)
(Optional Transform) Random histogram equalisation (50% probability)
(Optional Transform) Random JPEG artifact introduction at quality from 70-75 (100% probability)

The SOPInstanceUID (a globally unique identifier for a DICOM file) is used as the primary key because each input image 204 is independent. The macro AUROC (mean of each view position AUROC) was used as the performance metric for determining the best model. The mean validation AUROC and standard deviation was reported for each view position.

The test dataset consisted of manually classified images from in-house medical practitioners. The test dataset was chosen randomly from the proprietary dataset and a public dataset.

Modification for Cardiomegaly

Cardiomegalies are determined by the cardiothoracic ratio: the ratio of the heart width and the thorax width. To determine non-obvious cases, radiologists (labeller or user) annotate an input image 204, that is a frontal view, by drawing two lines, one for the heart and one for the thorax. A line consists of two points, e.g. endpoints $(x_1, y_1)$ and $(x_2, y_2)$, and there are two lines, such annotations can be defined by four pairs of coordinates.

Comparing predictions to the ground truth for such sets of coordinates conventionally employs mean squared error (MSE) or root mean squared error (RMSE), since this is a regression problem. Therefore, there are eight different values where the distance from the predicted value to the ground truth needs to be minimised. These may be denoted: heart_left_x; heart_left_y; heart_right_x; heart_right_y; thorax_left_x; thorax_left_y; thorax_right_x; thorax_right_y.

When MSE is used, the error is squared, meaning the direction of the error (e.g. two pixels to the left) is indistinguishable to errors in different directions. More generally, using MSE results in a circular perimeter around the ground truth with equal error values, which fails to reflect the true error in predicting the cardiothoracic ratio. In this case, the important goal is to identify the ratio, while still predicting the pixels well enough to automate the annotations and also give the user, e.g. a radiologist, more understanding of how the ratio was determined.

To address this issue, embodiments of the invention may employ a modified loss function for the annotation points associated with cardiomegaly which includes a weighting such that:

$$L_W = aP + bD + cR$$

where:
- a, b, and c are constant multipliers that may be chosen based upon limitations in pixel error due to image dimensions, resolution, etc.;
- P is the MSE for each of the eight point values as described above;
- D is the mean (or weighted average or median) of the MSE for both the heart width and thorax width measures; and
- R is the mean of the MSE of the ratio of the heart width and thorax width measures.

The loss weighting can be applied to the base loss function additively, multiplicatively, or according to other suitable weighting functions. The base loss function may be MSE or a suitable alternative.

Model Performance

FIGS. 6A-D show AUROC curves obtained using the trained models described above for the combination of tension and simple pneumothoraces 600, tension pneumothorax 602 and simple pneumothorax separately 604, and pneumothorax with no intercostal drain 606.

For all categories (all radiological findings), model performance was compared with the labelling statistics by expert radiologist labellers which provides a baseline when determining the clinical performance of the model relative to the average radiologist performance. Examples of such results are shown in Table 4, for the radiological finding of pneumothorax.

The bootstrap estimate of the average human radiologist AUROC is computed for each finding (see rows 'rad_roc_auc_1' to 'rad_roc_auc_5' in Table 4). Random readers (human radiologists) were selected and their AUROCs estimated per finding. This was performed repeatedly to calculate how the AUROC varies per reader. Batches of readers and cases were selected because a single reader's AUROC cannot be estimated with the spline interpolation. The mean and standard deviation are calculated over five bootstrap estimates (see rows 'rad_roc_auc_mean', 'rad_roc_auc_std').

The AUROC was quantified for each finding, for each fold of a 5-fold cross-validation process, and the average and standard deviation of the AUROCs across the five folds (see rows 'model_roc_auc_hopeful-donkey-583_2h45vvhs', 'model_roc_auc_unique-wildflower-596_8hp45vkw', 'model_roc_auc_gentle-fire-598_36kpxjvu', which show results for three of the five folds of cross-validation, and 'model_roc_auc_mean', 'model_roc_auc_std' which show the mean and standard deviation across those three folds).

The difference between the mean model AUROC and the mean radiologist AUROC (also referred to as 'delta', see row 'delta' in Table 4) was further calculated. The uncertainty in the model AUROC and the uncertainty in the radiologist AUROC were combined to get the uncertainty in the delta (see row 'combined_sd' in Table 4). The 95% confidence interval for the delta was calculated (upper and lower bounds, see rows 'upper_bound' and 'lower_bound' in Table 4). Therefore there is 95% confidence that the true delta lies between these two bounds. A cut off was applied e.g. the lower bound has to be over −0.05, such that there is 95% assurance that the deep learning model is less than 0.05 worse compared to the radiologist. If the lower bound exceeds 0, all the findings of the model are superior or non-inferior to the average radiologist.

The results in Table 4 show that the trained models 200/300, 402 described herein achieve excellent accuracy (superior or non-inferior to the average radiologist) for detection of both simple pneumothoraces and tension pneumothoraces.

Image Analysis Server Architecture

Referring to FIGS. 7A to 7C, an exemplary system for analysing radiology images (e.g. CXR) 818 will now be described. The exemplary system is based on a microservices architecture 700, a block diagram of which is illustrated in FIG. 7A, and comprises modular components which make it highly configurable by users and radiologists in contrast to prior art systems which are rigid and inflexible and cannot be optimised for changes in disease prevalence and care settings. Another benefit of a modular systems architecture comprising asynchronous microservices is that it enables better re-usability, workload handling, and easier debugging processes (the separate modules are easier to test, implement or design). The system 700 also comprises modular components which enable multiple integration pathways to facilitate interoperability and deployment in various existing computing environments such as Radiology Information Systems Picture Archiving and Communication System (RIS-PACS) systems from various vendors and at different integration points such as via APIs or superimposing a virtual user interface element on the display device of the radiology terminals/workstations 112. The virtual user interface element may be an interactive viewer component 701 as described below with reference to particular various interactive user interface screens of the viewer component 701 depicted in FIGS. 8A to 8F.

The system 700 provides a plurality of integration pathways via modular subcomponents including: PACS injection, RIS injections, synchronised viewer component 701, PACS inline frame (iFrame) support, PACS Native AI Support, or a Uniform Resource Locator (URL) hyperlink that re-directs the user to a web viewer on a web page executed in a web browser. The system may comprise a flexible integration layer 702, comprising one or more software components that may execute at on-premises hardware. The integration layer 702 may include a library module containing integration connectors, each corresponding to an integration pathway. Depending on the PACS system that is used by a customer, the library module may receive a request for a particular integration connector for the system of the present invention to interact with the customer via the PACS system. Similarly, depending on the RIS system that is used by a customer, the library module may receive a request for a particular integration connector for the system of the present invention to interact with the customer via the RIS system, for triage injection for re-prioritisation of studies. Certain integration connectors occupy or block a large portion of the viewport and this may be undesirable in certain circumstances for users.

In one example, PACS Native AI Support is preferred as the integration connector because the PACS is configured to display medical predictions from the system of the present invention natively, and the user interface resembles the existing PACS system. For example, the PACS Native AI Support may have a plurality of Application Programming Interfaces (APIs) available that enable the system of the present invention to communicate with such a PACS.

In another example, where a conventional radiology workstation 112 is unavailable or a PACS system is inaccessible, a user may use a mobile computing device such as handheld tablets or laptop to interact with the system of the present invention by injecting a URL link in a results window of an electronic health record (EHR) that, when clicked by the user, causes an Internet browser to direct them to a web page that executes a web viewer application to view the CXR image 818 and radiological findings predicted by the system. The web viewer displays the CXR image 818 with the segmentation indicated and the radiological findings detected by a deep learning network, such as e.g. by the Vision Classification model 200.

In another example, a synchronised viewer component 701 (e.g. as described below with reference to FIGS. 8A to 8F) may be used as the integration connector to overlay on an existing PACS system that may lack APIs to enable native AI support. The viewer component 701 displays the CXR image 818 with the segmentation indicated and the radiological findings detected by a deep learning network, such as the Vision Classification model 200. The viewer component 701 is repositionable by the user in the viewport in the event the viewer component 701 obscures the display of any useful information supplied from the PACS system.

The system 700 comprises modular user configuration components to enable users (e.g. clinicians and radiologists) to selectively configure the quantity of radiological findings they would like detected particular to their care setting. Another configurable option includes setting the sensitivity (Se) and specificity (Sp) for each radiological finding to be detected by the system of the present invention. For detecting a particular radiological finding, its sensitivity is how well it can be positive among all those with the condition. For detecting a particular radiological finding, its specificity is how well it can distinguish those with the radiological finding from those without the radiological finding. For triage injection the system 700 can configure priority for each finding and match that to a preference setting configured by the customer. For example, this flexibility and granularity of control of the system 700 is illustrated in the following scenarios: Rib lesion mapped to "Urgent" for customer A but mapped to "Low" for customer B. The scales are also customisable per customer, i.e. customer A priority is "Standard, Urgent, Critical" which is mappable by the system 700, while customer B may be "Very Low, Med, High, Very High" which can also be accommodated for.

A microservice is responsible for acquiring data from the integration layer 702 to send CXR images 818 to the AI model for generating predicted findings. The microservice is also responsible for storing study-related information, CXR images 818 and AI result findings. The microservice provides various secure HTTP endpoints for the integration layer 702 and the viewer component to extract study information to fulfil their respective purposes. In an exemplary embodiment, image formats accepted by the microservice is JPEG2000 codestream lossless format. Other image formats are acceptable such as PNG and JPEG. The microservice validates all CXR images 818 before they are saved and sent downstream for further processing.

The microservice functions (cloud-based or on-prem) may be summarised as follows.
1. Receive study information from the integration layer 702:
    a. Receive CXR images 818 from the integration layer 702
    b. Process and extract relevant study information and store into a database
    c. Store the CXR images 818 into a secure blob storage or object storage 712 (for example, an S3 bucket in AWS for a cloud deployment)
2. Send CXR images 818 to the AI model:
    a. Receive a study is ready for AI processing message from the integration layer 702
    b. Prepare and transmit the CXR images 818 to the AI model for generating predicted findings
    c. Store AI model generated predicted findings into a database
3. Receive request from viewer component 701:
    a. Send study information, CXR images 818 and AI model generated predicted findings
4. Receive request from the integration layer 702:
    a. Send the relevant study with its images for processing by the AI model
    b. Send complete study with AI model generated predicted findings back to the integration layer In an exemplary embodiment the architecture of the microservice is an asynchronous microservices architecture. The microservice uses a queueing service. The queuing service in a cloud deployment may provided by a host cloud platform (for example, Amazon Web Services, Google Cloud Platform or Microsoft Azure) to transmit messages from one microservice to the next in a unidirectional pattern. The queuing service in an on-premise deployment may be a message-broker software application or message-oriented middleware, comprising an exchange server and gateways for establishing connections, confirming a recipient queue exists, sending messages and closing the connections when complete. Advantageously this arrangement enables each microservice component to have a small and narrowed function, which is decoupled as much as possible from all the other narrowed microservice functions that the microservice provides. The advantage of the microservices pattern is that each individual microservice component can be independently scaled as needed and mitigates against single points of failure. If an individual microservice components fail, then the failed microservice components can be restarted in isolation of the other properly working microservice components.

All microservices are preferably implemented via containers (e.g. using Docker, or a similar containerisation platform). A container orchestration system (e.g. Kubernetes, or similar) is preferably deployed for automating application deployment, scaling, and management.

In an exemplary embodiment there is a single orchestration cluster with a single worker group. This worker group has multiple nodes, each of which may be a cloud-based virtual machine (VM) instance. After a microservice is deployed, the containers are not guaranteed to remain static.

The orchestration system may shuffle containers depending on a variety of reasons. For example:
1. exceeding the resource limits and subsequently killed to avoid affecting other containers;
2. crashes may result in a new container spun up in a different node to replace the previous container;
3. to dynamically add or remove compute capacity based on an increase or decrease in workload/demand; and/or
4. an increase and then decrease in replicas can result in shift to a new node.

Referring to FIG. 7A, a gateway service 704 provides a stable, versioned, and backward compatible interface to the viewer component 701t and the integration layer 702, e.g. a JavaScript Object Notation (JSON) interface. The gateway 704 provides monitoring and security control, and functions as the entry point for all interactions with the microservice. The gateway 704 transmits CXR images 818 to secure blob or object storage 712, and provides references to microservices downstream that require access to these CXR images 818. The gateway 704 is responsible for proxying HTTP requests to internal HTTP APIs and dispatching events into a messaging queue 708.

A distributed message queueing service (DMQS) 710 accepts incoming HTTP requests and listens on queues for message from the gateway 704 and a model handling service (MHS) 716. The payload of messages transmitted by the DMQS 710 is a list of CXR images 818 for a study including a secure signed URL of where the CXR image 818 is hosted in cloud storage 712. The DMQS 710 is configured to pass CXR images 818 to the MHS 716 for the model prediction pipeline. The DMQS 710 stores studies, CXR images 818, and deep learning predictions into a database managed by a database management service (DBMS) 714. The DMSQ 710 also manages each study's model findings state and stores the AI findings predicted by the models, and stores errors when they occur in a database via the DBMS 714, accepts HTTP requests to send study data including model predictions for radiological findings, accepts HTTP requests to send the status of study findings, and forwards CXR images 818 and related metadata to the MHS 716 for processing of the findings.

An advantage of DMQS 710 is that message queues can significantly simplify coding of decoupled applications, while improving performance, reliability and scalability. Other benefits of a distributed message queuing service include: security, durability, scalability, reliability and ability to customise.

A security benefit of the DMQS 710 is that who can send messages to and receive messages from a message queue is controlled. Server-side encryption (SSE) allows transmission of sensitive data (i.e. the CXR image 818) by protecting the contents of messages in queues using keys managed in an encryption key management service.

A durability benefit of the DMQS 710 is that messages are stored on multiple servers compared to standard queues and FIFO queues.

A scalability benefit of the DMQS 710 is that the queuing service can process each buffered request independently, scaling transparently to handle any load increases or spikes without any provisioning instructions.

A reliability benefit of the DMQS 710 is that the queuing service locks messages during processing, so that multiple senders can send and multiple receivers can receive messages at the same time.

Customisation of the DMQS 710 is possible because, for example, the messaging queues can have different default delay on a queue and can handle larger message content sizes by holding a pointer to a file object or splitting a large message into smaller messages.

The MHS 716 is configured to accept DICOM compatible CXR images 818 and metadata from the DMQS 710. The MHS 716 is also configured to download CXR images 818 from secure cloud storage 706. The MHS 716 also performs validation, and pre-processing to transform study data into JSON format, which may then be further transformed into a suitable format for efficient communication within the microservice, such as protocol buffer format (protobuf). Then the MHS 716 sends the study data to an AI model service (AIMS) 718 for AI processing, which identifies and returns the radiological findings predicted by the deep learning models executed by a machine learning prediction service (MLPS) 720. The MHS 716 then accepts the AI findings generated by the deep learning models which are returned via the AIMS 718. The MHS 716 parses, validates, and transforms the AI findings into JSON format and returns these to the DMQS 710.

The AIMS 718 is configured as a pre-processor microservice that interfaces with the MLPS 720 and MHS 716. This modular microservices architecture has many advantages as outlined earlier. The AIMS 718 preferably communicates using a lightweight high-performance mechanism such as gRPC. The message payload returned by the AIMS 718 to MHS 716 contains predictions that include classifications and segmentations. These predictions are stored into a database by the DMQS 710 via DBMS 714.

The MLPS 720 is a containerised service comprising code and dependencies packaged to execute quickly and reliably from one computing environment to another. The MLPS 720 comprises a flexible, high-performance serving system for machine learning models, designed for production environments such as, for example, TensorFlow Serving. The MLPS 720 processes the images in the Vision Attributes 402, Vision Classification 200 and CXR Vision Segmentation 300 deep learning models and returns the resulting predictions to the AIMS 718. The models 200, 300, 402 may be retrieved for execution from a cloud storage resource 108. The MLPS 720 returns the model outputs (i.e. the predictions) to the AIMS 718.

The system 700 further includes a cloud image processing service (CIPS) 706, which communicates at least with the gateway 704, and the MHS 716, as well as with the cloud storage 712. The primary functions of the CIPS 706 are to: handle image storage; handle image conversion; handle image manipulation; store image references and metadata to studies and findings; handle image type conversions (e.g. JPEG2000 to JPEG) and store the different image types, store segmentation image results from the AI model(s); manipulate segmentation PNGs by adding a transparent layer over black pixels; and provide open API endpoints for the viewer component 701 to request segmentation maps and images (in a compatible image format expected by the viewer component 701).

FIG. 7B illustrates a method (process and data transfers) for initiating AI processing of medical imaging study results, according to an exemplary embodiment of the invention. An image upload event notifies the microservice that a particular study requires generation of AI model finding results (i.e. predictions). The incoming request initiates saving of all relevant study information including the series, scan and image metadata into a secure database via the DBMS 714. The CXR images 818 are also securely stored in cloud storage 712, for use later for the model processing.

In particular, at step 722 the integration layer 702 sends a request comprising an entire study, includes associated metadata, i.e. scan, series and CXR images 818. The request is received by the gateway 704 which, at step 724, stores the CXR images 818 in cloud storage 706.

Further, at step 726, the gateway 704 sends the request, references to the stored CXR images 818, and other associated data via the queue 708 to the DMQS 710. At step 728, the DMQS 710: (1) stores the study, series, scan and image metadata into a database via the DBMS 714, with correct associations; and (2) stores the CXR images 818 in private cloud storage (not shown) with the correct association to the study and series.

FIG. 7C illustrates a method (process and data transfers) for processing and storage of medical imaging study results, according to an exemplary embodiment of the invention. This process is triggered by a 'study complete' event 730, which comprises a request sent from the integration layer 702 to notify the microservice that a particular study is finished with modality processing and has finalised image capturing for the study. This event will trigger the microservice to compile all related data required for the model to process CXR images 818 and return a result with AI findings. The AI findings result will then be stored in the cloud database.

In particular, at step 732 the gateway 704 forwards the study complete event to the DMQS 710. At step 734, the DMQS 710 sends the CXR images 818 of the study to the MHS 716, via a reference to the associated CXR images 818 in the cloud storage 712. At step 736 the MHS 716 fetches the CXR images 818 from cloud storage 712, processes them along with associated metadata into protobufs, and forwards the data to the AIMS 718. The AIMS 718 then pre-processes the CXR images 818 and sends them to the MLPS 720 at step 738.

In exemplary embodiments of the invention, image pre-processing by the AIMS 718 may comprise one or more of the following steps:
1. transform the CXR image 818 within the protobuf message received from the MHS 716 into a data structure accepted by the models executed by the MLPS 720 (e.g. TensorFlow tensor with datatype unit 16 and input shape matching the deep learning models);
2. expand image dimensions to include a channels dimension (alongside height and width) if not existent;
3. convert the CXR image 818 to grayscale if the channel dimension already exists and is not single channel;
4. convert the image datatype to a type supported by the models executed by the MLPS 720 (e.g. float32);
5. recalibrate the image pixels based on the linear model with the RescaleSlope and RescaleIntercept headers in DICOM image metadata;
6. shift pixel intensities such that the minimum value in each CXR image 818 is 0;
7. ensure pixel intensity increases with black being 0 and white being the maximum data type—if the photometric interpretation is MONOCHROME1 (black=maximum data type value, white=0), reverse the pixel intensities by subtracting the values from one;
8. up/downsample and pad the CXR image 818 with 0s to reshape it to the accepted model input shape if needed; and/or
9. rescale pixel intensities from [image minimum, 99.5th percentile] to [0, 1] such that they represent a percentage of relative intensities within the CXR image 818 (this allows the deep learning models to be trained to learn features based on relative values rather than absolute pixel intensities which can be prone to both systematic and random errors during image generation).

At step 740, the MLPS executes one or more trained ML models to performs inference on the pre-processed images, producing predictions that are sent back to the AIMS 718 at step 742. The AIMS 718 processes the resulting findings, and transforms them to protobufs for transmission back to the MHS 716 at step 744. The MHS 716 transforms the received findings into JSON format, and returns them to the DQMS 710 at step 746, upon which they are stored to a database via the DBMS 714, ready for subsequent retrieval.

User Interface

FIGS. 8A to 8F show screenshots of an exemplary user interface (UI) viewer component 701 illustrating methods of communicating the output of a deep learning model to a user. The UI addresses communicating AI confidence levels to a user (i.e. a radiologist) that is intuitive and easy to understand. In various embodiments of the invention, the viewer component 701 may be implemented as web-based code executing in a browser, e.g. implemented in one or more of JavaScript, HTML5, WebAssembly or another client-side technology. Alternatively, the viewer component 701 may be implemented as part of a stand-alone application, executing on a personal computer, a portable device (such as a tablet PC), a radiology workstation 112, or other microprocessor-based hardware. The viewer component 701 may receive the results of analysis of CXR images 818 from, e.g., a remote radiology image analysis service 110 or an on-site radiology image analysis platform 114. Analysis results may be provided in any suitable machine-readable format that can be processed by the viewer component 701, such as JavaScript Object Notation (JSON) format.

In some embodiments, the viewer component 701 is a desktop client application that is designed to sit alongside a physician's CXR Image Viewer setup displaying model results. The viewer component 701 may comprise three distinct components: (1) an image viewer log reader; (2) an HTTP client; and (3) the user interface.

When a physician performs an action in Image Viewer, such as accessing a study, entries are made in a log file. Finding and reading the CXR Image Viewer's log file is the task of the viewer component 701's log reader component. The viewer component 701 is installed as a desktop application which gives it access to the host file system. The log reader identifies the log file where CXR Image Viewer user activity is recorded, monitors the last entry, and uses regular expression text matching to extract information that identifies the study, study date, accession number, and associated patient. The log reader is also preferably able to identify which screen is active in a multi-screen setup where a different study can be open on each screen.

The HTTP client allows the viewer component 701 to communicate (request or submit) data with the microservice. The HTTP client provides authentication, loading study findings and findings feedback. For authentication, the viewer component 701 records user-entered credentials after installation. If valid, these credentials are used to sign headers to authenticate all further communication with the microservice.

Study findings are loaded when the log reader observes a new study is opened in Image Viewer, and the HTTP client makes a request for related findings. This query responds with completed findings which are displayed as a list in the UI or pending completion which can be displayed as a status update.

Figure 8A:
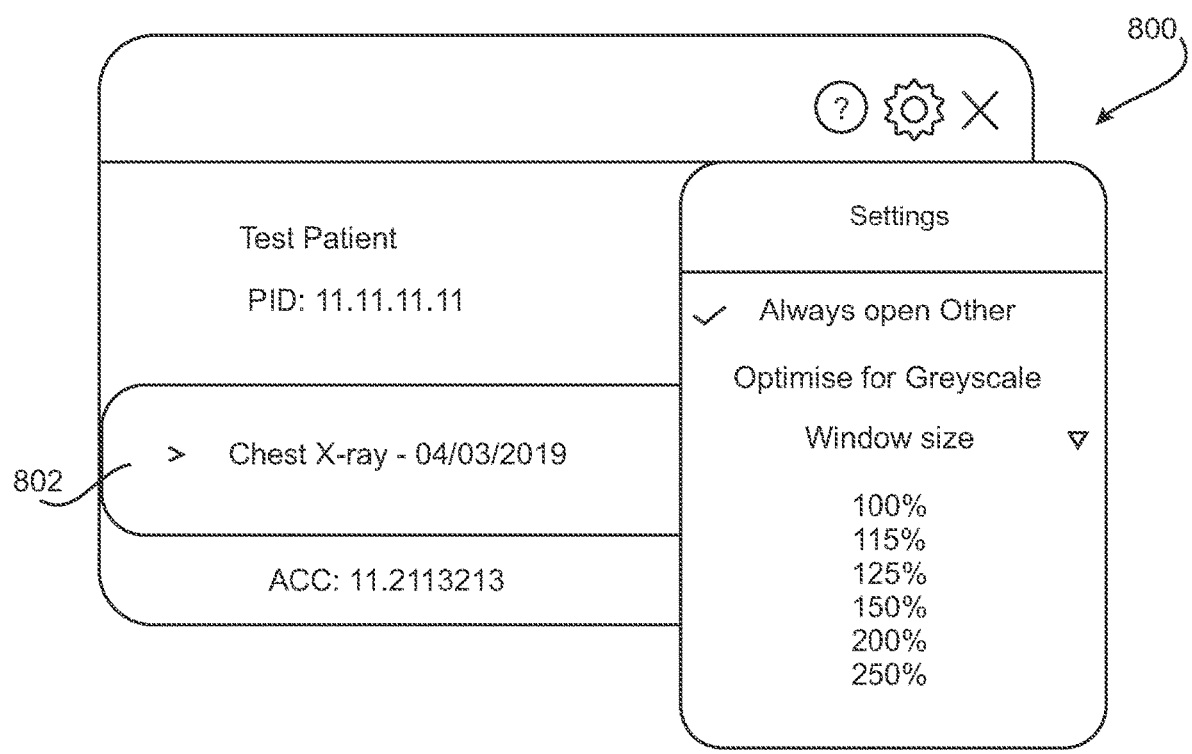
FIG. 8A to 8F show exemplary interactive user interface screens of a viewer component embodying the invention.
Figure 8B:
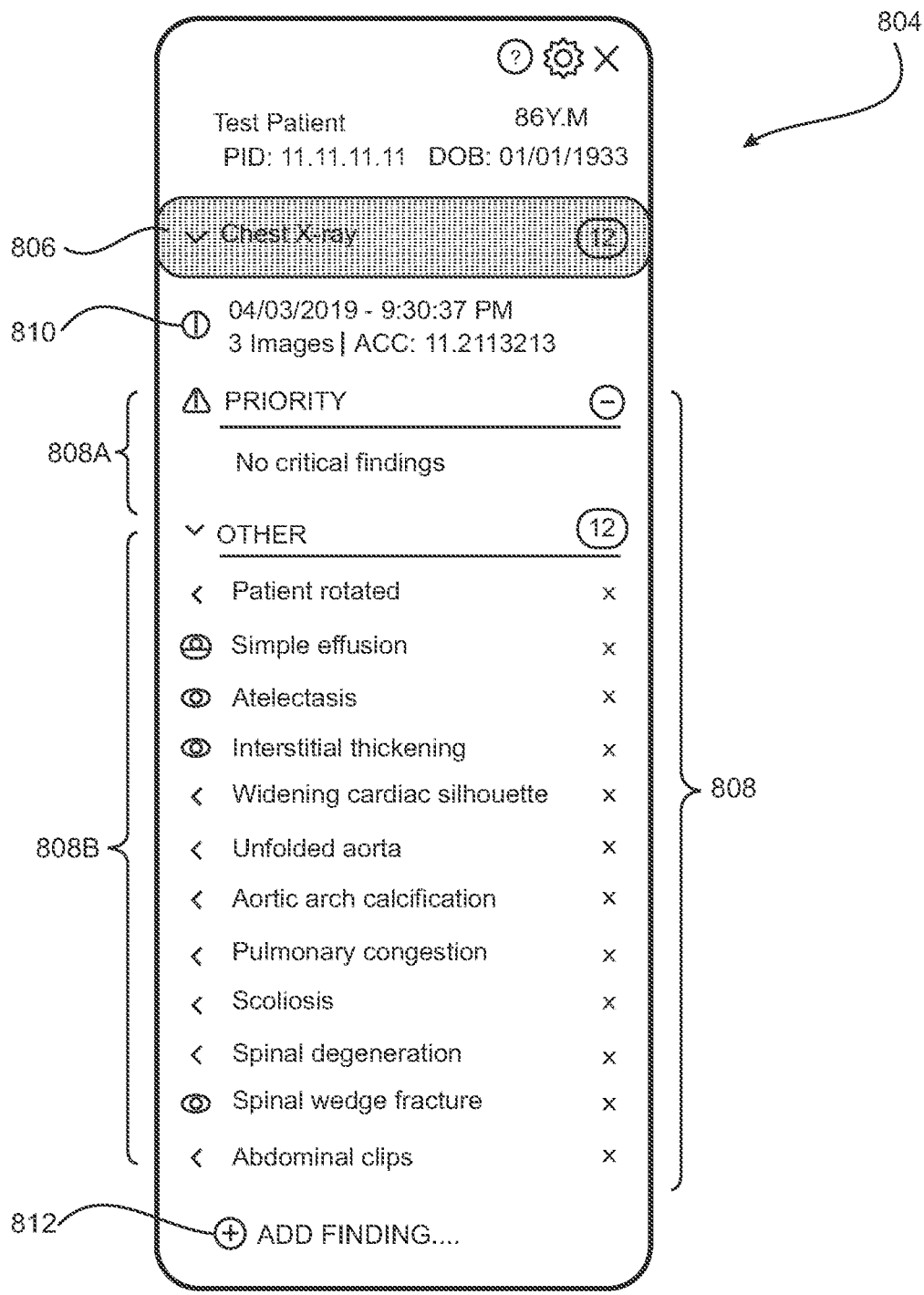

As illustrated in FIG. 8A, a window or dialog box 800 is provided from which the user is able to select a field 802 relating to a completed automated chest x-ray analysis ("Chest X-ray" tab). This results in an expanded dialog box 804, as shown in FIG. 8B, which displays a list of findings 808 associated with one or more CXR images 818. In this example, the list is separated between a first sublist 808A and a second sublist 808B. The first sublist 808A comprises priority findings. In the embodiment illustrated on FIG. 8B, there are no priority findings and hence the first sublist 808A is empty. An indication of one or more features 810 (e.g. metadata such as e.g. date associated with the CXR images 818, number of images, identifier such as e.g. DICOM identifier) of the CXR images 818 on which the automated analysis was based is also displayed (in this example, this is at the top of the collapsible section that is displayed by selecting the "Chest X-ray" tab). The viewer component 701 may also display an "add finding" button 812. By selecting this button, the user is able to provide an indication of a finding and/or an area of the one or more CXR images 818 associated with a finding, such as e.g. a finding that may have been missed by the deep learning models. This may be used to train (or at least partially retrain) one or more deep learning models used for the automated analysis of CXR images 818 as described herein.

Figure 8C:
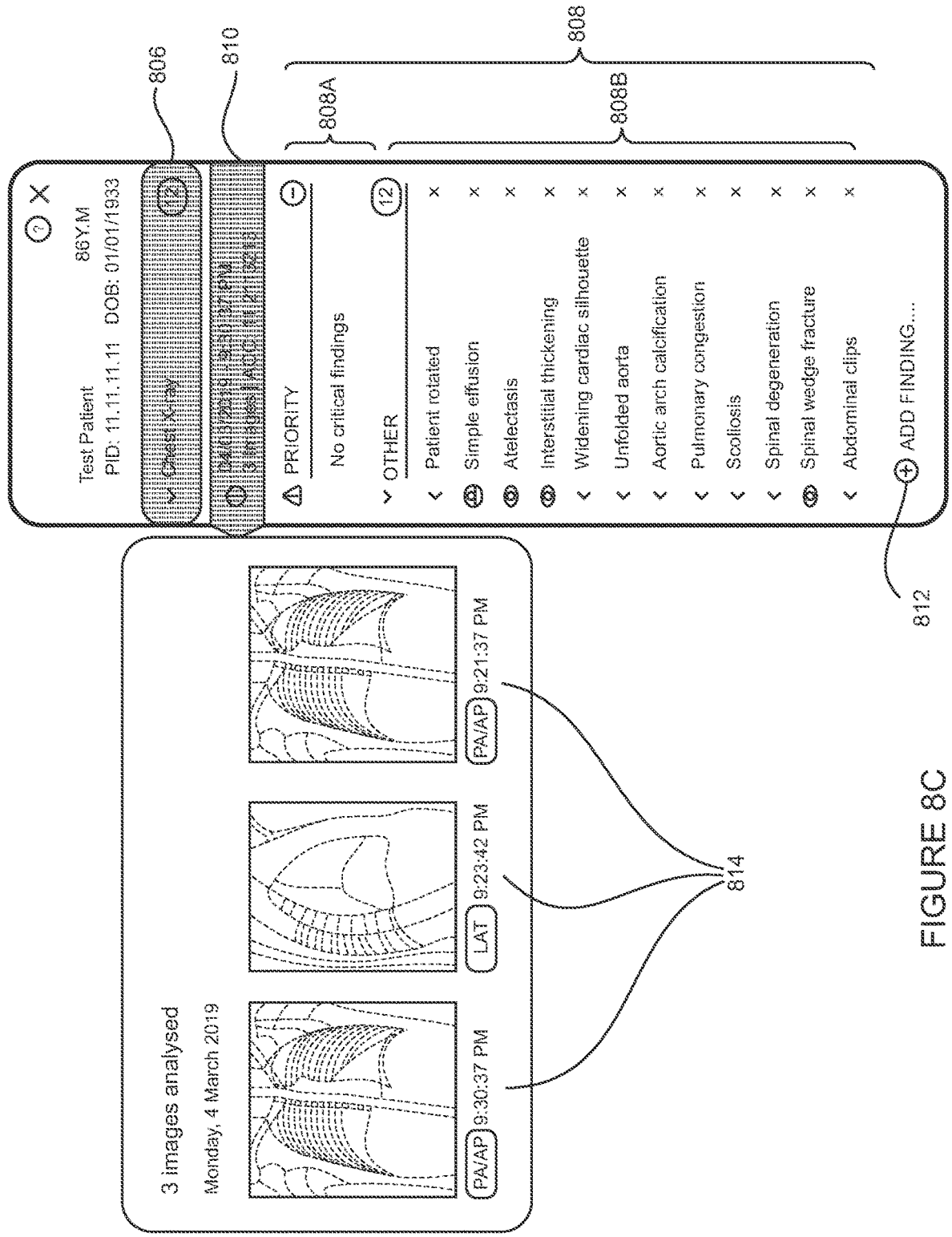

FIG. 8C shows the effect of a user selecting (such as, e.g., by hovering over) the field 810 containing the indication of the one or more features of the CXR images 818. This causes the viewer component 701 to display the one or more CXR images 818 as thumbnail images 814.

Figure 8D:
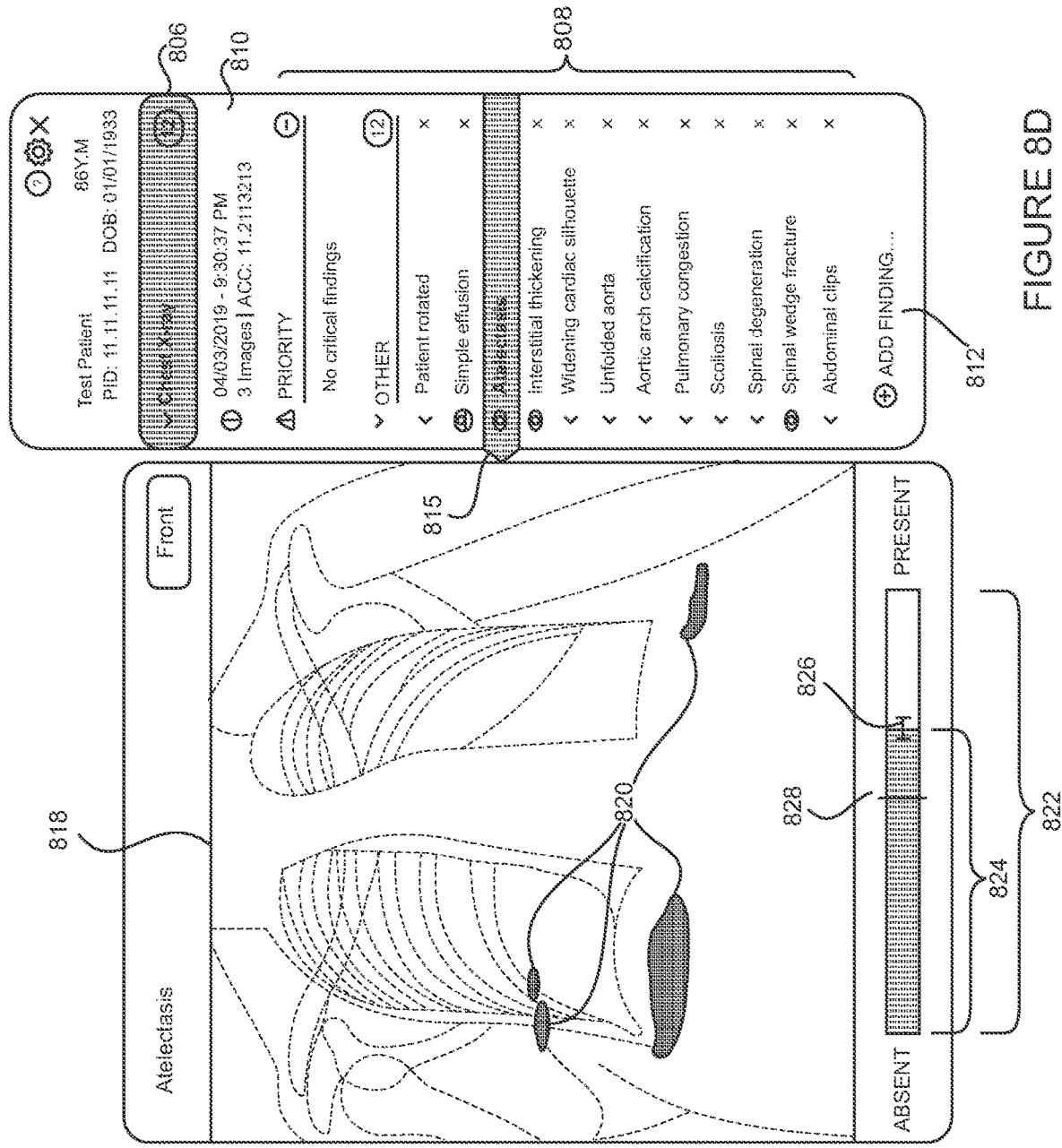
Figure 8E:
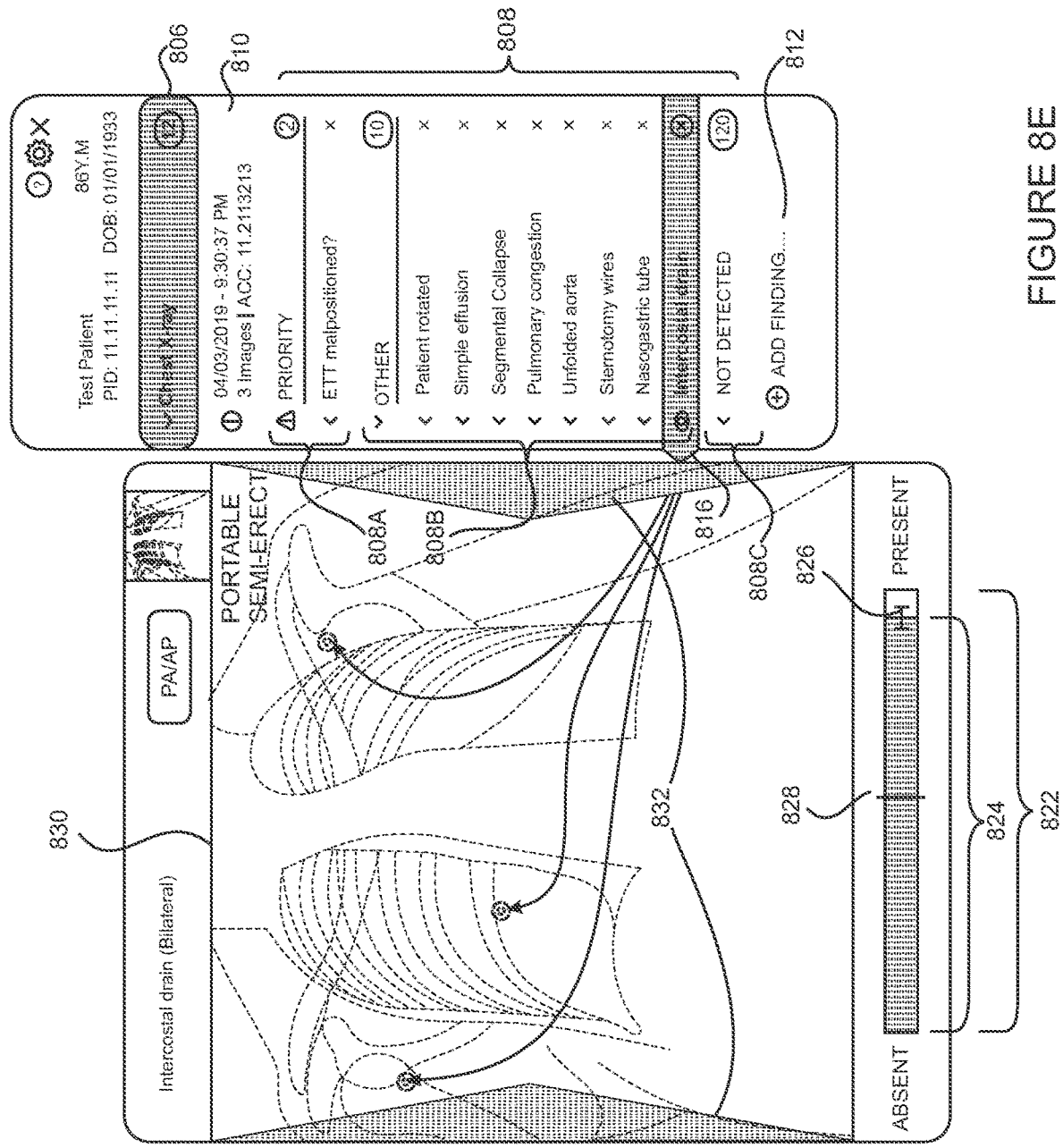
Figure 8F:
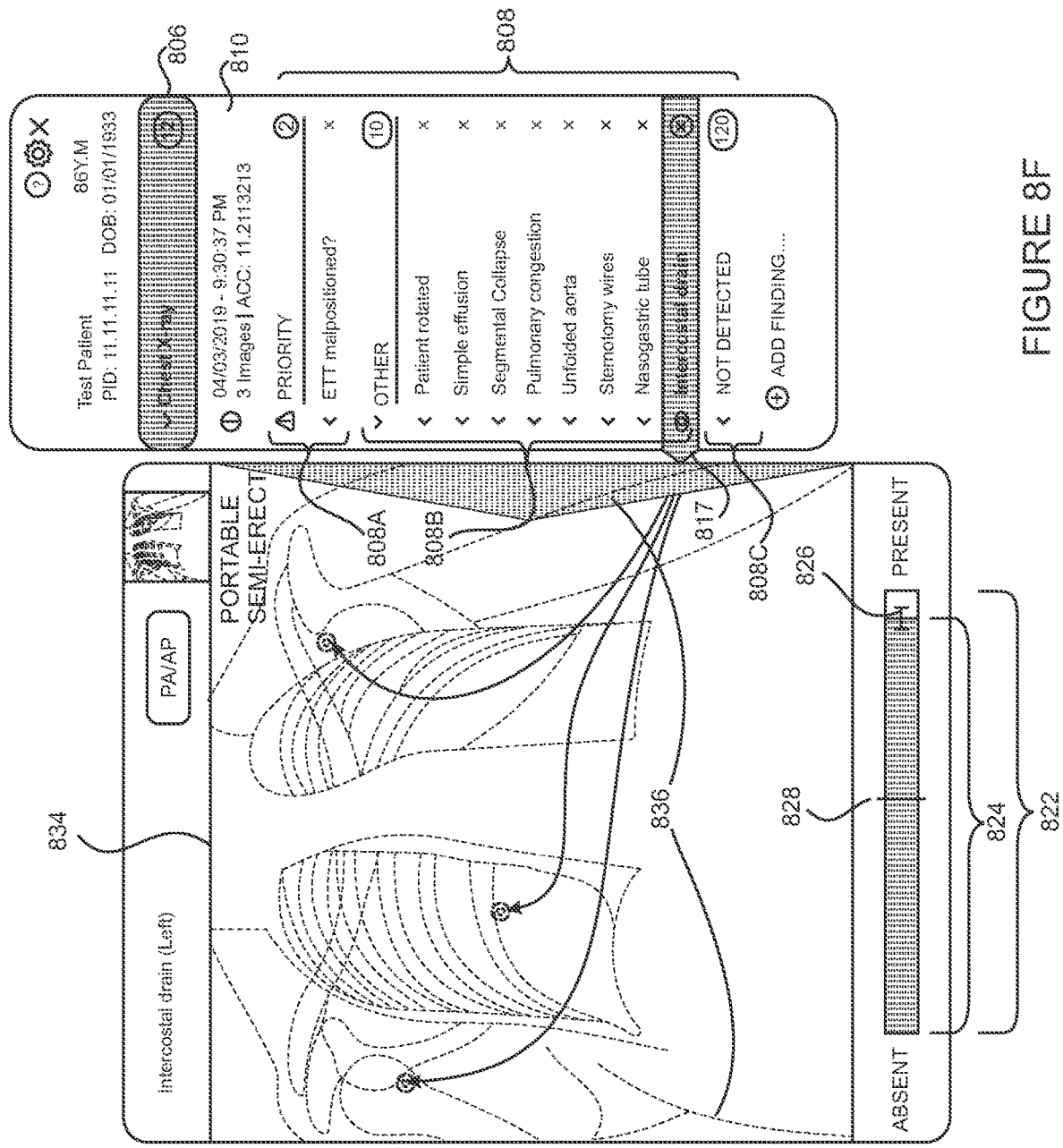

As shown in FIGS. 8D to 8F, the user may select (such as e.g. by hovering over) a particular finding 815, 816, 817 in the displayed list 808. This causes the viewer component 701 to display a corresponding CXR image 818, 830, 834 in which the selected finding has been detected. The application also displays a results bar 822 associated with the finding, described in further detail below. Further, the application also displays a segmentation map indicating the areas 820, 832, 836 of the image in which the finding has been detected. The segmentation map is preferably obtained using one or more Vision Segmentation models embodying the invention. In the display shown in FIG. 8E there is one priority finding in the first sublist 808A. As illustrated in FIGS. 8E and 8F, the list 808 may be divided into a first sublist 808A, a second sublist 808B and a third sublist 808C, where the first sublist 808A comprises priority findings, the second sublist 808B comprises other (i.e. "non priority") findings, and the third sublist 808C comprises findings that were included in the AI models but not detected in the particular images that have been analysed.

Figure 9:
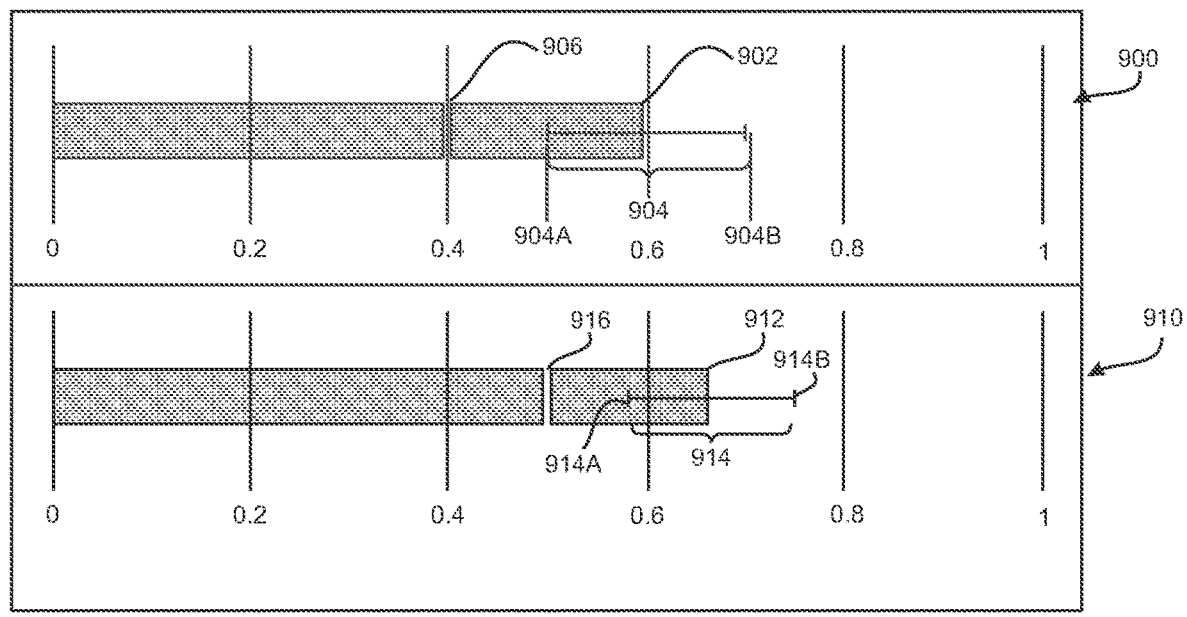
FIG. 9 illustrates exemplary user interface elements comprising results bars embodying the invention.

The results bar 822 appears with each finding as shown in FIGS. 8D to 8F. Further details of exemplary results bars based on 'raw' model results 900, and transformed values 910, are illustrated in FIG. 9. Features of the results bar 822 are computed and displayed in order to provide information about the output of machine learning models embodying the invention in a manner that is intuitive and easy to interpret. This is achieved in embodiments of the invention by using statistical properties of model outputs, in combination with prediction thresholds, as will now be described in greater detail.

As has been described, embodiments of the invention may employ an ensemble of models, e.g. a plurality of Vision Classification models, each of which is a deep neural network that produces a set of predictions of findings. The outputs of the ensemble may be combined to produce an improved set of predictions. Combining the predictions of the plurality of deep neural networks may comprise obtaining a score for a class that is the mean of the predictions of the plurality of deep neural networks for the class (also referred to herein as the 'mean_score' variable:

$$\mathrm{mean\_score} = \Sigma \mathrm{model\_predictions}/\mathrm{num\_predictions}$$

where 'model_predictions' are the predictions of each of the models in an ensemble of models for a particular class, and 'num_predictions' is the number of predictions/models in the ensemble). Combining the predictions of the plurality of deep neural networks may further comprise obtaining a statistical estimate of the variability of the predictions from the plurality of deep neural network interval, such as e.g. a standard deviation, standard error of the mean (also referred to herein as the 'sem' variable), and/or a confidence interval (also referred to herein as a pair of values 'upper_bound' and 'lower_bound'). Combining the predictions of the plurality of deep neural networks may comprise computing the Standard Error of the Mean (sem) as the standard deviation of the predictions of the plurality of models (DNNs) divided by the square root of the number of predictions:

$$\mathrm{sem} = \mathrm{std}(\mathrm{model\_predictions})/\mathrm{sqrt}(\mathrm{num\_predictions}).$$

Combining the predictions of the plurality of deep neural network may comprise obtaining an error or confidence value (also referred to herein as 'error' or 'confidence') that corresponds to the 95% confidence interval around an ensemble of predictions, for example:

$$\mathrm{error}_{95\%} = \mathrm{std}(\mathrm{model\_predictions}) * 1.96/\mathrm{sqrt}(\mathrm{num\_predictions})$$

Combining the predictions of the plurality of deep neural network may comprise obtaining a 95% confidence interval. A 95% confidence interval may be calculated as:

$$\mathrm{upper\_bound} = \mathrm{mean\_score} + \mathrm{sem} * 1.96$$

$$\mathrm{lower\_bound} = \mathrm{mean\_score} - \mathrm{sem} * 1.96$$

The prediction from a DNN (score), or an ensemble of DNNs (mean_score) may be compared to a threshold, 'predictionThreshold' (also referred to herein as 'operating point'). If the prediction is higher than the threshold then the radiological finding may be considered likely to be present, and if the prediction is lower than the threshold then the radiological finding may be considered likely to be absent.

The value for the 'predictionThreshold' variable may be set to a suitable default value. For example, default values for the 'predictionThreshold' variable may be input according to an ontology tree specification into a JSON configuration file. The default values may be selected and designed by a group of expert radiologists.

Alternatively, a suitable value for the 'predictionThreshold' variable may be provided by a user. For example, the value for the 'predictionThreshold' variable for each radiological finding may be adjusted by a customer organisation, such that the value applies for all users in that organisation. Depending on the care setting or clinical environment (e.g. emergency department of a hospital compared to an outpatient clinic), some organisations may want to adjust the sensitivity/specificity setting of one or more radiological findings to reduce the occurrence of false positives which requires adjustment of the 'predictionThreshold' variable. The ability to adjust is advantageous in improving usability of the system for users because they it reduces frustration arising from detecting a high number of false positives in particular care environments, and leads to higher adoption and acceptance of the system in terms of trust and user confidence.

As explained above, the models described herein may be configured to detect a large number of findings on a chest x-ray. The detection of each of these findings may occur when the prediction of the algorithm (e.g. the prediction from a single model or from an ensemble of models) exceeds the threshold chosen for that finding. In some embodiments, default values of the threshold are set for all findings. Default values of the threshold may advantageously be set to the threshold value that maximises the $F_1$ score (also known as F-score or F-measure, which is the harmonic mean of the precision and recall) for the model or ensemble of models for the respective class. Using the $F_1$ score equally balances the recall (also known as 'sensitivity', the fraction of the total amount of positive cases that were actually predicted as positive; i.e. the number of true positive predictions divided by the sum of the number of true positive and false negative predictions) and the precision (also known as 'positive predictive value', the fraction of positive cases amongst the cases that were predicted as positives; i.e. the number of true positive predictions divided by the sum of the number of true positive and false positive predictions) of the test.

However, in some circumstances, as described below, it may be advantageous to change the operating point (predictionThreshold) to obtain a higher recall or higher precision. In some embodiments, a range of thresholds for each finding may be provided to a user, and a particular threshold (operating point) may be user-selected. This advantageously allows optimisation for specific circumstances.

In some embodiments, a default values of the threshold may advantageously be set to the threshold that maximises the $F_\beta$ score for the prediction of the model or ensemble of models for the respective class, where:

$$F_\beta = (1+\beta^2)*(\text{precision}*\text{recall})/((\beta^2*\text{precision})+\text{recall})$$

The $\beta$ parameter captures the importance of recall versus precision. In particular, values of $\beta>1$ result in recall being considered more important than precision, and values of $\beta<1$ result in recall being considered less important than precision.

Advantageously, the threshold for a class may be set to the value that maximises the $F_\beta$ score with $\beta>1$ in embodiments where false positives are preferred to false negatives, i.e. where there is a higher tolerance for false positives to ensure that few of these findings are missed (also referred to herein as 'high recall situations'). Conversely, the threshold for a class may be set to the value that maximises the $F_\beta$ score with $\beta<1$ in embodiments where false negatives are preferred to false positives ((also referred to herein as 'high precision situations').

High recall situations may include screening tests such as, for example, one or more of:
1. Screening for tuberculosis in migrant chest X rays
   a. AIR SPACE OPACITY—focal and diffuse
   b. PULMONARY LESION—nodule, mass, calcified lesion, cavitating lesion
   c. calcified nodes—neck, hilar, axillary
   d. hilar lymphadenopathy
2. Screening for COVID
   a. AIR SPACE OPACITY—focal and diffuse
3. Screening for pneumoconiosis:
   a. INTERSTITIAL—upper, lower, diffuse
   b. PULMONARY LESION—nodule, mass, calcified lesion, cavitating lesion
   c. AIRWAYS—hyperinflation, bullous disease
   d. PLEURAL—pleural calcification, pleural mass
4. Screening for cancer:
   a. AIR SPACE OPACITY—focal and diffuse
   b. PULMONARY LESION—nodule, mass, calcified, cavitating lesion
   c. COLLAPSE—lobar collapse, segmental collapse
   d. CARDIOMEDIASTINUM—mediastinal mass, hilar mass
5. Screening for MRI safety:
   a. Lines and tubes
   b. Electronic devices
   c. Foreign bodies
   d. Orthopaedic implants High precision situations may include situations where a particular finding is very common in a particular population. In such embodiments, false positives may become distracting or tiresome to the users, reducing the effectiveness of the tool. Examples of situations where high precision may be preferable include:
1. Technical Factors: Many considerations go into deciding whether to repeat an X ray due to technical problems, other than just the degree to which the CXR image 818 is compromised. These include the increase in radiation dose to the patient, the potential risk in missing findings due to the technical problem, the cost in re-imaging the patient, the difficulty to the patient in having to return to the department and the risk to staff if quarantine precautions are required. In some practices it will be preferable to use a lower $\beta$ value to ensure that only the more severely compromised CXR images 818 are flagged.
2. Patient demographics: Practices that have a younger or older population may benefit from adjusting the operating points of some findings, such as cardiomediastinum, hiatus hernia and bowel distension, to better optimise for their cohort of patients. What is normal for a 70 year old patient may not be normal for a 30 year old. Cardiomegaly, abnormal aortic contours, hiatus hernia and bowel distension are common in the elderly and the $\beta$ values for these findings may warrant reduction in cohorts of elderly patients.

Certain ethnicities and age groups are prone to different bone lesions. It may be advantageous to alter the operating points of bone lesion findings for a practice that caters predominantly to a particular age group or ethnicity.

As will be appreciated, the foregoing approach enables numerical predictions of the Vision Classification model 200 to be converted into decisions regarding the likely presence or absence of corresponding visual findings, along with estimates of confidence in such decisions. A further transformation may then advantageously be applied to scale and normalise these results for presentation to the user via the results bar 822 of the viewer component 701. According to embodiments of the invention, a prediction value V of the Vision Classification model 200, relating to a visual finding, having a predictionThreshold T is transformed via a further predetermined fixed threshold FT to produce a transformed prediction value TV according to:

$$TV = FT\left(1 + \frac{V-T}{1-T}\right)$$

The above transformation has two properties that are relevant to the objective of generating a results bar display that is intuitive and easy to interpret. Firstly, the transformed threshold between predicting 'presence' or 'absence' of a visual finding (i.e. when V=T) is set to the fixed threshold FT, regardless of the setting of the predictionThreshold T (which, as discussed above, may vary in embodiments of the invention). Secondly, the maximum value of TV is equal to 2FT, such that all prediction values corresponding with presence of a visual finding lie between FT and 2FT, i.e. corresponding with the upper half of the results bar 822.

The above transformation thus has the desirable property that the prediction value V having a comparative relationship (i.e. 'greater than', 'equal to' or 'less than') to the finding-dependent predictionThreshold T is mapped to a transformed value TV such that the comparative relationship with the fixed threshold FT is maintained relative to V and T. The transformation thus enables a finding-dependent threshold value (i.e. T) to be mapped to a predetermined, finding-independent, fixed threshold value FT. This allows for a single, common, visual comparison to be provided across different visual findings for which the corresponding prediction values may differ.

In particular, in the case where the fixed threshold is predetermined to be FT=½, all prediction values corresponding with presence of a visual finding lie in the range (½; 1], such that the maximum range of the results bar 822 is [0; 1], with the threshold fixed at precisely the half-way point, which can be expected to align with the intuition of many users.

It is also desirable to compute transformed values of the upper and lower bounds of the error or confidence intervals, so that these can also be represented on the results bar 822. For a bound b=V+δv (where δv may be positive for an upper bound, and negative for a lower bound) a corresponding transformed value may be computed using the previous equation, i.e. as:

$$TV_b = FT\left(1 + \frac{V + \delta v - T}{1 - T}\right)$$

Alternatively, a transformed value of the relative error or confidence δv may be directly computed as:

$$TV_{\delta v} = FT\frac{\delta v}{1 - T}$$

Advantageously, therefore, the above transformations function to normalise values so that they are visually consistent for the user, while being simple to implement. In particular, normalising values to a fixed threshold at FT=½ enables the user to form an immediate impression of how "confident" the model is, at a glance. It is believed that, for most users, it is very intuitive to have a fixed threshold line in the middle of the graph such that when the results bar extends beyond this line, this signifies that the model predicts that the corresponding finding is present. By having a fixed threshold at FT=½ on the bar graph, the user may very quickly:

1. understand that the finding is present;
2. obtain an impression of how "confident" the model is; and
3. compare between findings (ie. given A and B is present, A is more likely to be present than B based on the confidence bar), which is a useful feature for differential diagnosis)

By contrast, if the threshold line were to differ for different findings, the user would not be able to make the above assessments is quickly and/or intuitively.

Benefits of the above transformations are further illustrated by exemplary results bars based on 'raw' model results 900, and transformed values 910, are illustrated in FIG. 9. The corresponding raw and scaled values, for FT=½, are summarised as follows:

| | Raw Input (Bar 900) | Scaled Input (Bar 910) |
|---|---|---|
| threshold (predictionThreshold) | 0.4 (T) | 0.5 (FT) |
| score (or mean_score) | 0.6 (F) | 0.66667 (TV) |
| error (sem* 1.96) | 0.1 (8v) | 0.08333 ($TV_{\delta v}$) |
| lower_bound | 0.5 (V − 8v) | 0.58333 (TV − $TV_{\delta v}$) |
| upper_bound | 0.7(V + 8v) | 0.75 (TV + $TV_{\delta v}$) |

For the raw results bar 900 the predicted value 902 is 0.6, the confidence interval 904 has a lower bound 904A of 0.5 and an upper bound 904B of 0.7, and the threshold 906 is 0.4. As has been described, the prediction thresholds and confidence intervals may vary for each individual visual finding, and thus values as illustrated by the raw results bar 900 are not generally comparable between findings, and may therefore be difficult for the user to interpret readily. Following transformation, the scaled results bar 910 is generated, for which the predicted value 912 is 0.66667, the confidence interval 914 has a lower bound 914A of 0.58333 and an upper bound 914B of 0.75, and the threshold 916 is 0.5. Following transformation, the prediction threshold for each individual finding is fixed at 0.5, the transformed predictions for 'present' visual findings all lie between 0.5 and 1.0, and the confidence intervals are directly comparable on the same scale.

Accordingly, in embodiments of the invention, transformed values are used in the construction and display of the results bar 822 as shown in FIGS. 8D to 8F. The results bar 822 is graphically presented in the horizontal scale with ABSENT and PRESENT at its ends (corresponding with numerical values '0' and '1' as illustrated in FIG. 9). The transformed score corresponding with the positive prediction is represented by the filled portion 824, while the transformed confidence interval is represented by the error bar 826. The threshold 828 is fixed at the point halfway along the results bar 822.

In an exemplary implementation, the viewer component 701 receives raw prediction data generated by a model executed by a a remote radiology image analysis service 110 or an on-site radiology image analysis platform 114 is a JSON format, such as the following.

{
  "label": "aortic_stent",
  "labelName": "Aortic stent",
  "groupId": 2,
  "displayOrder": 31,
  "predictionThreshold": 0.104346967,
  "features": {
    "assign": false,
    "assist": true,
    "assure": false
  },
  "predictionProbability": 0.86942135,
  "confidence": 0.2548
}

This data includes the raw prediction score (i.e. 'predictionProbability', which is the mean prediction for an ensemble of models), the raw one-sided confidence interval magnitude (i.e. 'confidence', which is the 95% confidence interval around the mean prediction), and the prediction threshold associated with the 'Aortic stent' visual finding (i.e. 'predictionThreshold').

Using this data, the viewer component 701 is able to calculate the corresponding scaled values required to generate the results bar 822. For example, the following JavaScript code may be used to perform the scaling for the viewer component 701:

```
const scaleConfidenceValues=({
  error,
  threshold,
  score,
}: DetailFooterProps): ScaledConfidenceValues=>{
  const scaledThreshold=0.5;
  const scaledScore=
      (scaledThreshold*(score-threshold))/
          (1-threshold)+scaledThreshold;
  let    scaledError=(scaledThreshold*error)/(1-threshold);
  if (scaledScore+scaledError>1) {
    scaledError=1-scaledScore;
  }
  return {
    scaledScore,
    scaledThreshold,
    scaledError
  };
};
```

The value for the predictionThreshold variable for each visual finding can be set to default values or adjusted by a customer organisation, as explained above, such that the value applies for all users in that organisation. In this example, default values for the predictionThreshold variable are initially input according to an ontology tree specification into a JSON configuration file. The default values may be selected and designed by a group of expert radiologists. Depending on the care setting or clinical environment (e.g. emergency department of a hospital compared to an outpatient clinic), some organisations may want to adjust the sensitivity/specificity setting of one or more radiological findings to reduce the occurrence of false positives which requires adjustment of the predictionThreshold variable. The ability to adjust is advantageous in improving usability of the system for users because it reduces frustration arising from detecting a high number of false positives in particular care environments, and leads to higher adoption and acceptance of the system in terms of trust and user confidence.

Reduction of Transmitted Data

A common problem when providing an automated medical analysis solution where the AI analysis is at least in part run remotely (such as e.g. on a cloud-based radiology image analysis server 110) is to improve the responsiveness perceived by the user (e.g. radiologist, radiographer or clinician) when receiving the results/predictions generated by the AI model(s). This problem is not limited to AI models that analyse chest x-rays, as in the exemplary embodiments described above, and may also arise—and may even be exacerbated—when the imaging modality is CT or MRI where there are hundreds of images compared to the one to four images typically expected for chest x-rays.

This problem is addressed in embodiments of the invention through features that can each be used independently, or in advantageous embodiments, synergistically.

1. Reduce the payload/data size that is transmitted from the cloud server 110 to the client/workstation 112 via the Internet 102.

2. Pre-fetch some or all images and (advantageously payload reduced) segmentation maps in the background and storing on a local cache in the client's workstation 112 to avoid wasting time that could be used to receive images and segmentation maps and therefore use the available Internet bandwidth from the moment user has opened a particular study. This is advantageous compared to downloading images and segmentation data on demand in response to user clicks because the user does not have to experience delay in waiting for the completion of the download.

Each of these features will now be described in greater detail.

In embodiments of the invention, segmentation maps such as those described above, may be stored as transparent PNG files. Prior to this method, the segmentation maps were stored as text files corresponding to a grid of numbers, resulting in a large file size, for example, 500 KB per segmentation map.

For CXR images 818 analysed using an embodiment of the invention, it was observed that about half of the radiological findings in the ontology can be associated with a segmentation map, because the radiological finding is visually identifiable in a region of the CXR images 818. For CXR there are usually one to three CXR images 818 per subject. At an extreme end, a patient may have 50 radiological findings (i.e. someone in very poor health) identified in at least one of the images 818. If about half of these (i.e. 25 findings) are associated with segmentation maps, and that there are three CXR images (frontal, lateral, etc) 818 for the patient, the total amount of data to transfer from cloud to client is:

3 images (each of the 3 CXR images); and 25 segmentation maps (e.g. 500 KB×25).

In embodiments where the medical scan images are CT or MRI scans rather than CXRs, the quantity of data will often be much higher (since the number of images analysed is higher than chest x-ray). This represents a very large amount of data to be sent to the user/workstation 112 over the Internet 102, and may cause some delay in a user receiving the results of the deep learning analysis, and hence being able to use these to make a diagnosis in a timely manner. The problem is exacerbated if the user is located in an environment that has poor Internet connectivity or low Internet speeds, which is the case for a significant proportion of the world's population who may reside outside of urban areas.

In embodiments of the invention the image/pixel data is separated from the segmentation data (metadata). The segmentation data identifies where in the image a particular radiological finding is located, and is presented to the user with a coloured outline with semi-transparent coloured shading. A lossless compression algorithm, e.g. PNG, is used to compress the file size of the separated segmentation data from 500 KB down to 1 KB to 2 KB. The viewer component 701 is then able to display the image and the segmentation map as two images on top of each other (e.g. a segment image overlying the x-ray image).

This step has a very significant impact on improving the user experience and increasing UI responsiveness, because a smaller data size is required to be transmitted to communicate the same information without any reduction in quality of the information being communicated.

Segmentation maps can be stored as PNG files, in particular transparent PNG files. As mentioned above, PNG is advantageous because it supports lossless data compression, and transparency. Additionally, PNG is a widely supported file format. Other file formats may be used such as JPEG, which has wide support but does not support transparency or lossless compression, or GIF, which supports transparency but not lossless compression and is not as widely supported as PNG or JPEG.

In some embodiments, instead of transparent PNGs, the segmentation maps could be stored as area maps. Area maps may advantageously reduce file size because only the corners need to be defined. This may be advantageously used when only a region of an CXR image 818 has to be highlighted, not a particular shape of the region. This may not be adequate or advantageous for all situations. Further, the use of area maps may create extra steps on the server-side, as area maps have to be obtained from the segmentation information (array of 0's and 1's) received from the deep learning model(s).

Alternatively, in other embodiments the segmentation maps may be stored as SVG files. SVG is a vector based image format. This advantageously enables the interactive viewer component 701 to have more control over the display of the information. In particular, vector images are scalable (they can be scaled to any dimension without quality loss, and are as such resolution independent), and support the addition of animations and other types of editing. Further, vector based image formats may be able to store the information in smaller files than bitmap formats (such as PNG or JPEG) as their scalability enables saving the CXR image 818 at a minimal file size.

In a further enhancement, embodiments of the invention may provide a pre-fetching module is which is configured to pre-fetch the CXR images 818 and segmentation maps. The feature is also referred to as lazy loading because the user is not required to do anything for the data to transmit passively in the background. In some embodiments, pre-fetching may occur without user knowledge or there may be a visual element displayed in the user interface such as a status bar that may indicate download activity or download progress. Therefore, the interaction by the user with the viewer component 701 ultimately is not perceived as laggy to the user because all the necessary data is stored in the local cache in the client's workstation 112 ahead of the time it is required to be presented to the user 112. The need to download data in real-time is obviated and avoids the user 112 having to wait or see a screen flicker because data needs to be downloaded at that moment for processing and presentation to the user, e.g. in the viewer component 701.

Advantageously, in a further embodiment, the pre-fetching of the CXR images 818 and segmentation maps is performed intelligently, by creating a transmission queue that includes logic that predicts the next likely radiological findings that will draw the attention of the user. For example, important (or clinically significant/high priority) radiological findings and their segmentation maps are ordered at the start of the transmission queue and retrieved first, and the less important ones following. Alternatively or additionally, the system may detect the position of the mouse cursor within the interactive viewer component 701 on a specific radiological finding (active position), and retrieve images/segmentation maps corresponding to the adjacent radiological findings (previous and next), first. The priority logic is configured to progressively expand the retrieval of images/segmentation maps from further previous and further next which is ordered correspondingly in the transmission queue. The transmission queue is re-adjustable depending on a change in the mouse cursor position to determine what the active position is and the specific radiological finding.

The code snippets below represent exemplary implementations of these functions.

```
//Pre-fetching CXR images:
return (data?.images ?? [ ]).reduce((acc: UIImageUrl,
    image)=>{const url=image.targets?.jpeg?.url;
    // Pre-fetch image to avoid UI flickering when display-
        ing it the
    // first time
    new Image( ).src=url;
    return {
        . . . acc,
        [image.imageInstanceUid]: url,
    };
}, { });
//Pre-fetching segmentation maps:
return findingsSegment.segments.reduce((acc:  UISeg-
    mentUrl, segment)=>
{
    // Pre-fetch image to avoid UI flickering when display-
        ing it the
    // first time
    new Image( ).src=segment.url;
    return {
        . . . acc,
        [segment.id: segment.url,
    };
}, { });
```

The functions depict a loop through image URLs that a Cloud Imaging Processing Service (CIPS) 706 passes to the interactive viewer component 701 for any given study.

The pre-fetching module enables the interactive viewer component 701 to be at least one step ahead of the user's attention or intended action, therefore it is perceived by the user to be seamless and snappy.

The functionalities described above can be implemented as part of the CIPS 706 that stores study images, AI segment results and handles image conversions and manipulations. A service gateway is configured to trigger events to CIPS 706 for image uploads and processing. CIPS 706 is responsible for receiving, converting and storing images into secure cloud storage 712. CIPS 706 is configured: (a) to provide image processing capabilities; (b) to provide both an asynchronous and synchronous image storage and retrieval mechanisms; and (c) to store model segmentation findings (generated by the AI model).

Figure 10:
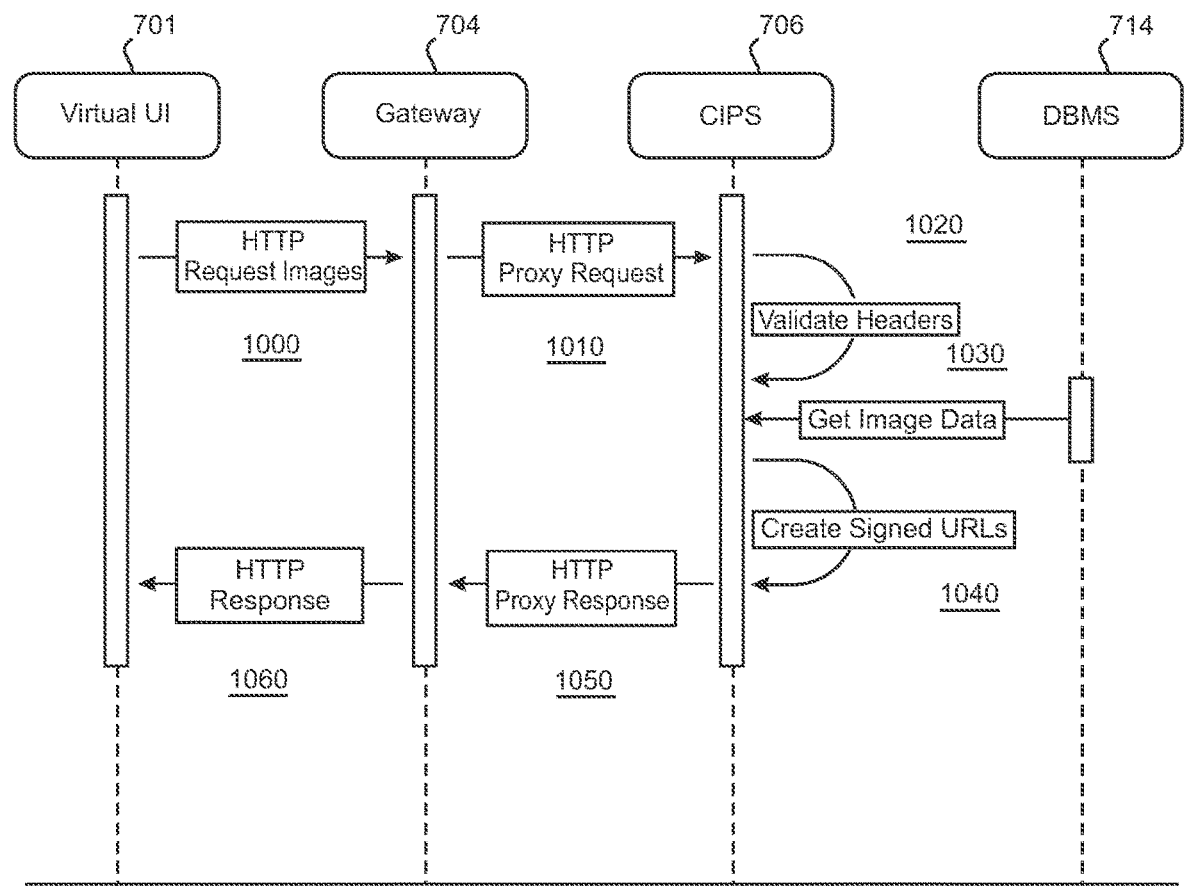
FIG. 10 is a signal flow diagram illustrating an exemplary method for providing image data to a viewer component within the embodiment of FIG. 7A.

Referring to FIG. 10, a method of providing image data to the viewer component 701 will now be described. At step 1000 the viewer component 701 (client) sends image instance UI Ds to the service gateway (Receiver) using the HTTP protocol. At step 1110, the gateway (client) forwards the request with payload to CIPS (Receiver). CIPS 706 optionally validates the header of the request at step 1020, and then retrieves (step 1030) the image data from the DBMS. CIPS 706 then generates 1040 a secure cloud storage image URL for the image, which the viewer component 701 can use to fetch and display images. CIPS 706 responds to the request with the image data via the gateway, which then forwards this to the viewer component 701 at steps 1050, 1060, using the HTTP protocol.

Figure 11:
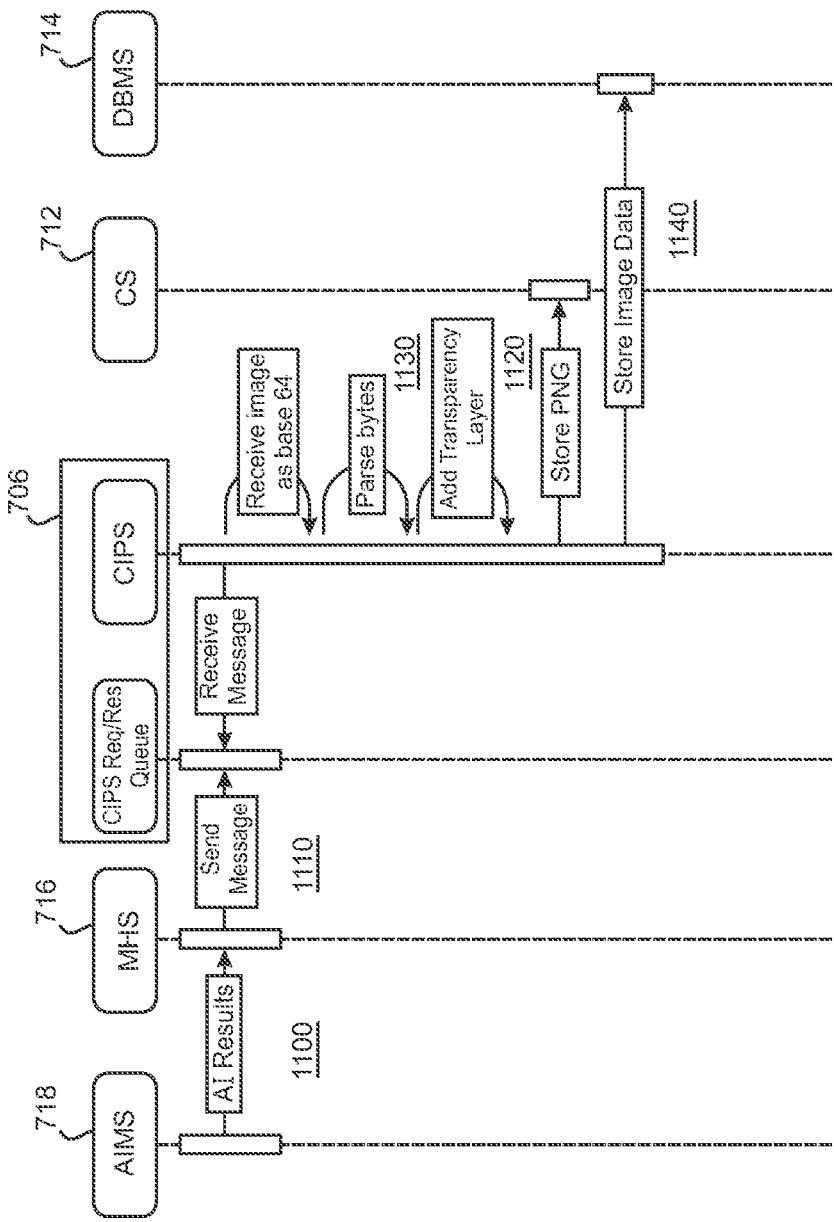
FIG. 11 is a signal flow diagram illustrating a method of processing a segmentation image result within the embodiment of FIG. 7A.

Referring to FIG. 11, a method of processing a segmentation image result will now be described. At step 1100, the AI Model Service (AIMS, client) sends AI findings results including a segmentation image and metadata to the Model Handler Service (MHS, Receiver). At step 1110, MHS sends the segmentation image results as a PNG to CIPS 706. At step 1120, CIPS 706 stores the segmentation image as a PNG in secure cloud storage. At step 1130, CIPS 706 manipulates the CXR image 818 by adding a layer of transparent pixels on top of black pixels. At step 1140, CIPS 706 stores the segmentation image metadata, the image secure URL location and the study finding metadata to the DBMS.

Augmented Diagnostic Accuracy Study

A CXR decision support tool embodying the invention, substantially as described above, has been evaluated for its ability to assist clinicians in the interpretation of chest radiography and improve CXR interpretation, encompassing the full range of clinically relevant findings seen on frontal and lateral chest radiographs. This study had two endpoints: (1) How does the classification performance of radiologists change when the deep learning model is used as a decision support adjunct? (2) How does a comprehensive deep learning model trained to detect a large set of clinical findings (e.g. 127 in this case) on CXR perform and how does its performance compare to that of practising radiologists?

The retrospective, single sequence, two period, multi-reader multi-case (MRMC) study evaluated the diagnostic performance of 20 radiologists with and without the aid of the deep learning classifier. The radiologists interpreted the cases without access to the deep learning classifier, and also interpreted the same cases with the support of the deep learning tool following a three month wash-out period. Model development and evaluation involved three groups of radiologists each performing a separate function: (1) training dataset labelling (120 radiologists), (2) gold standard labelling (7 radiologists), and (3) the interpretation of cases in the MRMC study proper (20 radiologists). Training dataset labelling defined the radiological findings present on each case in the training dataset. Gold standard labelling defined the radiological findings present in the testing dataset used for the MRMC study. Interpretation refers to the process of identifying findings present in a study. A total of 147 fully accredited radiologists from Australia and Vietnam took part in this process.

To select a dataset for the MRMC study, a statistical power analysis was performed to identify an enriched subset of cases. To assess diagnostic accuracy over all 127 findings at 80% power for detecting at least a difference of 0.02 in AUROC with 95% confidence per finding, with 18 radiologists, 2,568 studies were required. (The statistical power analysis determined that a minimum dataset of 2,568 studies would be required to detect a mean difference in AUROC of around 0.02 in the diagnostic accuracy of 18 radiologists in labelling all 127 findings with alpha=0.05 and beta 0.8.) The MRMC dataset cases were excluded from the model training process such that no patient within the test dataset was present within the dataset used to train the deep learning model. The MRMC dataset was designed to have 50% of studies from the private Australian radiology dataset, and 50% from the MIMIC dataset. Commonly co-occurring findings were controlled so that episodes of co-occurrence comprised no more than 50% of all cases of that finding within this dataset.

'Gold standard' ground truth labels for the MRMC dataset were determined by a consensus of three independent radiologists drawn from a pool of seven fully credentialed Australian subspecialty thoracic radiologists. These radiologists had access to anonymised clinical information, past and future CXR images 204 and reports and relevant chest computed tomography (CT) reports. These radiologists did not have access to the outputs of the deep learning model. The gold standard labels were derived from a Dawid-Skene consensus algorithm from independent labelling of the studies by the three radiologists.

Prior to labelling or gold standard annotation, radiologists underwent rigorous training. This involved: familiarisation with the annotation tool; reviewing definitions of each clinical finding; and training on a dataset of 113 CXR images 204 covering each finding in the ontology tree. The performance of each labeller was assessed with the F1 metric. Each gold standard labeller had an F1 score averaged across all findings exceeding 0.5, and each labeller an F1 score exceeding 0.45.

Twenty radiologists each classified each of the CXR images 204 in the MRMC dataset. Patient age and sex were shown but no radiological report or other comparison studies were provided. Radiologists were asked to rate their confidence in the presence of each of the 127 findings using a five-point scale. Labelling, gold standard annotation, and classification were performed using the same custom-built, web-based DICOM viewer. Radiologist interaction was performed on diagnostic quality monitors and hardware.

For each case in the MRMC dataset, the trained model identified positive findings according to the operating thresholds and the model's confidence. For findings that could be localised, the model produced an overlay or right/left lateralization relevant to that finding. This information was displayed on a software interface for the radiologists in the second arm of the study.

The primary endpoint of the study was the difference in radiologist performance with and without assistance from the deep learning model. This included the few cases excluded from analysis by the attributes model, which were interpreted by the radiologists alone, simulating real world practice for cases of image analysis failure. Where the model was unable to interpret a case, it was excluded from secondary endpoint analysis for both arms of the study, as that analysis focused on model performance.

Similarly, clinical findings for which model output was insufficiently powered due to low prevalence across the MRMC dataset were retained for the primary endpoint analysis (focused on radiologist performance), but discarded for secondary endpoint analysis.

Multiple performance metrics were calculated for each group and for the model. The positive predictive value (PPV), sensitivity, and specificity for each finding were estimated to assess performance. Receiver operating characteristics (ROC) curves were plotted using these metrics. The generalized Roe and Metz model and FDA iMRMC v4.0.1 software were used to analyse radiologist performance (AUROC) with and without the assistance of the model (Gallas B. D., Hillis S. L., 'Generalized Roe and Metz receiver operating characteristic model: analytic link between simulated decision scores and empirical AUC variances and covariances' *J Med Imaging* 2014, 1: 31006; Tan and Le, 2019). PPV, sensitivity, and Matthews Correlation Coefficient (MCC) for each radiologist were calculated by binarizing confidence scores for each finding. An AUROC difference greater than 0.05 and an MCC difference of greater than 0.1 were considered clinically significant. Any finding with a rating ≥1 (finding could not be completely excluded) was considered positive. Bootstrapping was used to determine if there was a statistically significant difference in the average MCC across the 20 radiologists for each finding between arms.

A subset of 34 'critical findings' was identified prior to the commencement of the study by a thoracic subspecialist radiologist. These critical findings represented the results most likely be clinically relevant.

For the secondary endpoint, the AUROC of the model for each of these findings was compared to the average radiologist AUROC for the corresponding finding. The mean and standard deviation of radiologist and model performance was obtained by bootstrapping over both radiologists and studies. The difference in AUROC between radiologists and the model was calculated by bootstrapping over both cases and radiologists to determine if the model was non-inferior to radiologists. Any study that could not be interpreted by the model was excluded from the secondary endpoint. The Benjamini-Hochberg procedure (Benjamini Y., Hochberg Y., 'Controlling the false discovery rate: a practical and powerful approach to multiple testing', *J R Stat Soc Ser B* 1995, 57: 289-300) was used to control the false positive rate, accounting for multiple comparisons. A standard significance threshold of p<0.05 was used for statistical tests.

A total of 4,568 images from 2,568 studies were included in the MRMC dataset and classified by the radiologist group. Seventeen studies were not interpreted by the model: nine were rejected as no frontal image was recognised by the model, four were rejected as no CXR image was found by the model, three had a processing error and one case had missing data. Therefore, the primary endpoint 'intention to treat' analysis included 2,568 studies and the secondary endpoint analysis included 2,551 studies.

While the ontology tree (Table 1) comprises 127 clinical findings, review of the training and testing datasets revealed that suboptimal intercostal catheter position (ICC), 'pneumobilia' and 'portal venous gas' were infrequently present in both datasets, with poor agreement between labellers. This limited statistical analysis of model performance for these three findings, therefore model performance for 'pneumobilia' and 'portal venous gas' was not assessed. The initially separate labels of "suboptimal ICC" and "satisfactory ICC" were merged to create a single label to identify the presence of an ICC, for secondary endpoint analysis assessing model performance. This new label demonstrated sufficient prevalence in the test dataset for analysis. To alleviate concerns regarding multiple comparisons, these three additional comparisons were adjusted for during the Benjamini Hochberg procedure for a total of 127 comparisons for the primary endpoint. A total of 124 clinical findings were predicted by the model. These 124 findings formed the basis of the secondary endpoint analysis.

Unassisted radiologists demonstrated a macro-averaged AUROC (macroscopic mean AUROC) of 0.713 across the 127 clinical findings. The lowest AU ROC was obtained for 'peribronchial cuffing' (0.562). The highest AUROCs were obtained for 'electronic cardiac devices' (0.979), 'sternotomy wires' (0.967) and 'shoulder replacement' (0.964).

Radiologist performance across all 127 clinical findings was analysed both with and without assistance from the model. The change in AU ROC between the first and second arms of the study was significant and positive for 101 clinical findings. AUROC did not decrease significantly for any finding (95% confidence interval includes 0 for the delat) and was statistically non-inferior (lower bound of the 95% confidence intervals for the deltas resides between −0.05 and 0) for twenty findings. The impact of the model on radiologist performance for the remaining six findings was inconclusive as the lower bounds of the 95% confidence interval were less than −0.05 and the upper bounds were greater than zero. These inconclusive findings were 'image obscured', 'portal venous gas', 'rib fixation', 'overexposed', 'widened aortic contour', and 'underexposed'. The three findings that demonstrated the greatest AUROC increase were 'hiatus hernia' (0.633 to 0.877), 'lung resection with volume loss' (0.654 to 0.879), and 'osteopaenia' (0.625 to 0.844). Notably, clinically salient findings such as "rib lesion" and "simple pneumothorax" also improved substantially, from 0.741 to 0.890 and 0.746 to 0.895, respectively.

One hundred findings demonstrated a statistically significant improvement in MCC when the radiologists used the deep learning classifier. By the same analysis, twenty-three of the remaining findings were statistically non-inferior. The other four findings were inconclusive as the lower bounds of the 95% confidence interval were less than −0.1 and the upper bounds were greater than zero. The four inconclusive findings were 'image obscured', 'portal venous gas', 'overexposed' and 'rib fixation'. In addition, radiologist MCC for the detection of any critical finding on a given study improved by 0.082 (0.030-0.139), from 0.491 to 0.573. Radiologist sensitivity for critical findings significantly improved from 0.890 to 0.956, while PPV decreased slightly from 0.905 to 0.899. Most findings demonstrated an improved sensitivity, with no overall decrease in PPV.

Radiologists demonstrated a macro-averaged AUROC of 0.717 across all 124 clinical findings. The model demonstrated a macro-averaged AUROC of 0.957 across all 124 clinical findings. The lowest AUROCs were obtained by the model for 'peribronchial cuffing' (0.829) and 'focal airspace opacity' (0.842). The highest AUROC of 1.000 was obtained for 'shoulder replacement', 'electronic cardiac devices' and 'sternotomy wires'. The model AUROC was statistically non-inferior to radiologist performance for all clinical findings, and statistically superior for 117 of these. The lower bound of the AUROC deltas lay between −0.05 and 0 for the seven non-inferior findings: 'shoulder fixation', 'rib fixation', 'oesophageal stent', 'gastric band', 'in position pulmonary arterial catheter', 'clavicle fixation' and 'shoulder replacement'.

Model-assisted radiologist performance was superior to unassisted radiologist performance for 80% of CXR findings and non-inferior in 95%. In the remaining 5% of findings, results were equivocal. The model-assisted radiologists did not demonstrate inferior performance on any findings when compared to unassisted radiologists.

Comparing standalone model performance versus radiologists in this non-clinical setting is not a true reflection of clinical practice. However, acknowledging this limitation, the deep learning model performance was either superior or non-inferior to radiologists in 124 clinical findings. The diagnostic performance of the model was exceptional across the range of findings and exceeded that of previously published models.

The superior model performance can be at least partially attributed to the large number of studies labelled by radiologists for model training using a prospectively defined ontology (Table 1) of CXR findings. Many other large-scale attempts to train deep learning models on CXR data have relied on text mining from the original radiology reports (Wu J. T., Wong K. C. L., Gur Y., et al., 'Comparison of Chest Radiograph Interpretations by Artificial Intelligence Algorithm vs Radiology Residents', *JAMA Netw Open* 2020, 3: e2022779-e2022779; Elkin P. L., Froehling D., Wahner-Roedler D., et al., 'NLP-based identification of pneumonia cases from free-text radiological reports', *AMIA Annual Symposium Proceedings*, American Medical Informatics Association, 2008: 172), a process which has been criticised for inconsistency and inaccuracy (Oakden-Rayner L., 'Exploring large-scale public medical image datasets', *Acad Radiol* 2020, 27: 106-12). Furthermore, the model advantageously utilises all common CXR projections (AP, PA, lateral), which represents the standard of care in actual clinical practice.

Improvement in human performance was dramatic with model assistance, even allowing for the automated exclusion (in the secondary endpoint, not the primary endpoint analysis) of seventeen studies due to quality factors.

Explaining improved radiologist performance with model assistance is a complex task, as is interpreting these results in a clinical context. While radiology reports are known to be incomplete descriptions of medical images, the radiologists in this study were trained to describe all imaging findings that were present on the studies. Nevertheless, when multiple findings are present, radiologists are less likely to perceive them all (Fleck M. S., Samei E., Mitroff S. R., 'Generalized "satisfaction of search": Adverse influences on dual-target search accuracy', *J Exp Psychol Appl* 2010, 16: 60; Gloskey L., 'Visual Search Array Structure and Satisfaction of Search Errors: Evidence from Eye Movements' 2018; Berbaum K. S., Krupinski E. A., Schartz K. M., et al., 'Satisfaction of search in chest radiography 2015', *Acad Radiol* 2015, 22: 1457-65.), which may have contributed to the results. In general, missed findings on radiologist reports have generally been attributed to satisfaction of search, difficulties in interpreting technically suboptimal imaging, and human error. The model provided additional information to the radiologists in the second arm of the study, facilitating improved decision making.

Hidden stratification is a well-known risk of deep learning models applied to medical imaging (Oakden-Rayner L., Dunnmon J., Carneiro G., Ré C., 'Hidden stratification causes clinically meaningful failures in machine learning for medical imaging', *Proceedings of the ACM Conference on Health, Inference, and Learning*, 2020: 151-9.). Multiple findings are commonly present on medical images and their identification depends on view position, imaging technique or the presence of other findings. Public datasets such as the NIH ChestXray14 dataset (Wang et al., 2017) often do not account for these confounding factors explicitly and therefore models trained on these datasets cannot effectively evaluate this issue. Comprehensively labelling these datasets enabled a detailed hidden stratification analysis and control of these issues.

This study demonstrates the potential for embodiments of the invention to improve the quality of CXR reporting. A strength of the system evaluated is that it has been developed into a ready-to-implement clinical tool. It can determine that the input data is appropriate, analyse the CXR images 818, and present the findings to reporting radiologists. This diagnostic accuracy study demonstrated that radiologist diagnostic performance improved when assisted by a comprehensive CXR deep learning model embodying the invention. The model performed at or beyond the level of radiologists for most findings when compared to a high-quality gold standard.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organisational purposes only and are not to be construed as limiting the subject matter described.

Tables

TABLE 1

CXR visual findings ontology tree
findings: chest_findings:

| | |
|---|---|
| airway_findings: | pleura_findings: |
| hyperinflation: | pneumothorax: |
| hyperlucency : | tension_pneumothorax: |
| peribronchial cuffing: | simple_pneumothorax: |
| bronchiectasis: | pleural_effusion: |
| tracheal_deviation: | loculated_effusion: |
| | simple_effusion: |
| | pleural_thickening: |
| | diffuse_pleural_thickening: |
| | calcified_pleural_plaque: |
| | pleural_mass: |
| cardomediastinal_findings: | abdominal_findings: |
| great_vessels_findings: | hiatus_hernia: |
| pulmonary_artery_enlargement: | gallstones: |
| pulmonary_congestion: | distended_bowel: |
| acute_aortic_syndrome: | subdiaphragmatic_gas: |
| widen_cardiomediastinum: | intrahepatic_gas: |
| cardiomegaly: | portal_venous_gas: |
| mediastinal_mass: | pneumobilia: |
| superior_mediastinal_mass: | |
| inferior_mediastinal_mass: | |
| pneumomediastinum: | |
| hilar_node_findings: | |
| hilar_lymphadenopathy: | |
| calcified_hilar_lymphadenopathy: | |
| chest_wall_findings: | diaphragmatic_findings: |
| pectus_excavatum: | diaphragmatic_eventration: |
| pectus_carinatum: | diaphragmatic_elevation: |
| technical_factors: | soft_tissue_findings: |
| patient_technical_factors: | subcutaneous_emphysema: |
| underinflation: | calcified_nodes: |
| cervical_flexion: | calcified_axillary_nodes: |
| patient_rotated: | calcified_neck_nodes: |
| device_technical_factors: | mastectomy: |
| overexposed: | |
| underexposed: | |
| technician_technical_factors: | |
| incompletely_imaged: | |
| image_obscured: | |
| age_related_changes: | |
| aortic_arch_calcification: | |
| unfolded_aorta: | |
| masquerades: | |
| pericardial_fat_pad: | |
| nipple_shadow: | |
| musculoskeletal_findings: | |
| osteopaenia: | |
| degnerative_spine: | |
| dish: | |
| spine_arthritis: | |
| shoulder_dislocation: | |
| shoulder_arthritis: | |
| spinal_deformity: | |
| kyphosis: | |
| scoliosis : | |
| bony_lesions: | |
| rib_lesion: | |
| humeral_lesion: | |
| clavicle_lesion: | |
| scapular_lesion: | |
| spine_lesion: | |
| fractures: | |
| rib_fracture: | |
| chronic_rib_fracture: | |
| acute_rib_fracture: | |
| rib_resection: | |
| humeral_fracture: | |
| acute_humerus fracture: | |
| chronic_humerus_fracture: | |
| clavicular_fracture: | |
| chronic_clavicle_fracture: | |

TABLE 1-continued

CXR visual findings ontology tree
findings: chest_findings:

| | |
|---|---|
| acute_clavicle_fracture: | |
| scapular_fracture: | |
| spine_wedge_fracture: | |
| lung_findings: | medical_foreign_bodies: |
| collapse: | lung_sutures: |
| significant_collapse: | surgical_clip: |
| segmental_collapse: | neck_clips: |
| lung_collapse: | axillary_clips: |
| lung_resection_volloss: | mediastinal_clips: |
| linear_atelectasis: | abdominal_clips: |
| airspace_opacity: | stent: |
| airspace_opacity_without_focus: | coronary_stent: |
| diffuse_lower_airspace_opacity: | biliary_stent: |
| diffuse_airspace_opacity: | aortic_stent: |
| diffuse_upper_airspace_opacity: | oesophageal_stent: |
| diffuse_perihilar_airspace_opacity: | airway_stent: |
| airspace_opacity_with_focus: | aerodigestive_tubes: |
| multifocal_airspace_opacity: | ett: |
| focal_airspace_opacity: | in_position_ett: |
| interstitial_thickening: | malpositioned_ett: |
| interstitial_thickening_volloss: | ngt: |
| interstitial_thickening_volloss_diffuse: | in_position_ngt: |
| interstitial_thickening_volloss_lower: | malpositioned_ngt: |
| interstitial_thickening_volloss_upper: | central_catheters: |
| interstitial_thickening_no_volloss: | cvc: |
| interstitial_thickening_upper: | in_position_cvc: |

TABLE 1-continued

CXR visual findings ontology tree
findings: chest_findings:

| | |
|---|---|
| interstitial_thickening_lower: | malpositioned_cvc: |
| interstitial_thickening_diffuse: | pac: |
| bullae: | in_position_pac: |
| bullae_upper: | malpositioned_pac: |
| bullae_lower: | intercostal_drain: |
| bullae_diffuse: | in_position_intercostal_drain: |
| lung_lesion: | malpositioned_intercostal_drain: |
| calcified_lung_lesion: | gastric_banding: |
| calcified_granuloma: | malpositioned_gastric_band: |
| calcified_pulmonary_mass: | gastric_band: |
| non_calcified_lung_lesion: | breast_implant: |
| cavitating_lung_lesion: | sternotomy_wires: |
| cavitating_mass: | orthopedic_devices: |
| cavitating_mass_internal_content: | clavicle_fixation: |
| | rotator_cuff_anchor: |
| | shoulder_hardware: |
| simple_lung_lesion: | shoulder_fixation: |
| single_pulmonary_mass: | shoulder_replacement: |
| single_pulmonary_nodule: | rib_fixation: |
| multiple_pulmonary_masses: | spinal_fixation: |
| miliary: | cardiac_devices: |
| | electronic_cardiac_devices: |
| | cardiac_valve_prosthesis: |
| | internal_foreign_body: |

TABLE 2

CXR visual findings hidden stratification definitions.
airway_findings: hyperinflation or peribronchial_cuffing or bronchiectasis or tracheal deviation
significant_collapse: segmental_collapse or lung_collapse or lung_resection_volloss
collapse: significant_collapse or linear_atelectasis
airspace_opacity_without_focus: diffuse_lower_airspace_opacity or diffuse_airspace_opacity or diffuse_upper_airspace_opacity or diffuse_perihilar_airspace_opacity or pulmonary_congestion
airspace_opacity_with_focus: multifocal_airspace_opacity or focal_airspace_opacity
airspace_opacity: airspace_opacity_without_focus or airspace_opacity_with_focus
interstitial_thickening_volloss: interstitial_thickening_volloss_diffuse or interstitial_thickening_volloss_lower or interstitial_thickening_volloss_upper
interstitial_thickening_no_volloss: interstitial_thickening_upper or interstitial_thickening_lower or interstitial_thickening_diffuse
interstitial_thickening: interstitial_thickening_volloss or interstitial_thickening_no_volloss
bullae: bullae_upper or bullae_lower or bullae_diffuse or hyperlucency
calcified_lung_lesion: calcified_granuloma or calcified_pulmonary_mass
cavitating_lung_lesion: cavitating_mass or cavitating_mass_internal_content
multiple_lung_lesion: multiple_pulmonary_masses or miliary
single_lung_lesion: single_pulmonary_mass or single_pulmonary_nodule
solid_lung_lesion: single_pulmonary_mass or single_pulmonary_nodule or multiple_pulmonary_masses
non_calcified_lung_lesion: cavitating_lung_lesion or solid_lung_lesion
lung_lesion: calcified_granuloma or calcified_pulmonary_mass or cavitating_mass or cavitating_mass_internal_content or single_pulmonary_mass or single_pulmonary_nodule or multiple_pulmonary_masses or miliary
lung_findings: collapse or airspace_opacity or interstitial_thickening or bullae or lung_lesion or airway_findings
pneumothorax: tension_pneumothorax or simple_pneumothorax
pleural_effusion: loculated_effusion or simple_effusion
pleural_thickening: diffuse_pleural_thickening or calcified_pleural_plaque or pleural_mass
pleural_findings: pneumothorax or pleural_effusion or pleural_thickening
pleuroparenchymal_findings: lung_findings or pleural_findings
great_vessels_findings: pulmonary_artery_enlargement or pulmonary_congestion or acute_aortic_syndrome
mediastinal_mass: superior_mediastinal_mass or inferior_mediastinal_mass or hiatus_hernia
widen_cardiomediastinum: cardiomegaly or mediastinal_mass or acute_aortic_syndrome
hilar_node_findings: hilar_lymphadenopathy or calcified_hilar_lymphadenopathy
cardomediastinal_findings: pulmonary_artery_enlargement or pulmonary_congestion or acute_aortic_syndrome or cardiomegaly or superior_mediastinal_mass or inferior_mediastinal_mass or pneumomediastinum or hilar_lymphadenopathy or calcified_hilar_lymphadenopathy

TABLE 2-continued diaphragmatic_findings: diaphragmatic_eventration or diaphragmatic_elevation
intrahepatic_gas: portal_venous_gas or pneumobilia
abdominal_findings: hiatus_hernia or gallstones or distended_bowel or
subdiaphragmatic_gas or intrahepatic_gas
chest_wall_findings: pectus_excavatum or pectus_carinatum or kyphosis or scoliosis
or rib_resection
rib_fracture: chronic_rib_fracture or acute_rib_fracture
humeral_fracture: acute_humerus_fracture or chronic_humerus_fracture
clavicular_fracture: chronic_clavicle_fracture or acute_clavicle_fracture
rib_findings: chronic_rib_fracture or acute_rib_fracture or rib_resection or
rib_lesion
humeral_findings: acute_humerus_fracture or chronic_humerus_fracture or
humeral_lesion or shoulder_arthritis
clavicular_findings: chronic_clavicle_fracture or acute_clavicle_fracture or
clavicle_lesion
scapular_findings: scapular_fracture or scapular_lesion
spinal_findings: kyphosis or scoliosis or dish or spine_arthritis or spine_lesion
or spine_wedge_fracture or osteopaenia
fractures: rib_fracture or humeral_fracture or clavicular_fracture or
scapular_fracture or spine_wedge_fracture
acute_fractures: acute_rib_fracture or acute_humerus_fracture or
acute_clavicle_fracture
bony_lesions: rib_lesion or humeral_lesion or clavicle_lesion or scapular_lesion
or spine_lesion
degenerative_spine: dish or spine_arthritis
skeletal_findings: osteopaenia or dish or spine_arthritis or shoulder_dislocation
or shoulder_arthritis or kyphosis or scoliosis or rib_lesion or humeral_lesion or
clavicle_lesion or scapular_lesion or spine_lesion or chronic_rib_fracture or
acute_rib_fracture or rib_resection or acute_humerus_fracture or
chronic_humerus_fracture or chronic_clavicle_fracture or acute_clavicle_fracture or
scapular_fracture or spine_wedge_fracture or pectus_excavatum or pectus_carinatum
calcified_nodes: calcified_axillary_nodes or calcified_neck_nodes
breast_findings: mastectomy or breast_implant or calcified_axillary_nodes or
axillary_clips
soft_tissue_findings: subcutaneous_emphysema or calcified_axillary_nodes or
calcified_neck_nodes or mastectomy or breast_implant
surgical_clip: neck_clips or axillary_clips or mediastinal_clips or
abdominal_clips
stent: coronary_stent or biliary_stent or aortic_stent or oesophageal_stent or
airway_stent
ett: in_position_ett or malpositioned_ett
ngt: in_position_ngt or malpositioned_ngt
aerodigestive_tubes: ett or ngt
cvc: in_position_cvc or malpositioned_cvc
pac: in_position_pac or malpositioned_pac
central_catheters: cvc or pac
intercostal_drain: in_position_intercostal_drain or
malpositioned_intercostal_drain
malpositioned_lines_and_tubes: malpositioned_cvc or malpositioned_ett or
malpositioned_ngt or malpositioned_pac or malpositioned_intercostal_drain
lines_and_tubes: aerodigestive_tubes or central_catheters or intercostal_drain
gastric_banding: malpositioned_gastric_band or gastric_band
shoulder_hardware: shoulder_fixation or shoulder_replacement or clavicle_fixation
or rotator_cuff_anchor
orthopedic_devices: clavicle_fixation or rotator_cuff_anchor or shoulder_hardware
or rib_fixation or spinal_fixation
medical_foreign_bodies: lung_sutures or surgical_clip or stent or lines_and_tubes
or gastric_banding or breast_implant or orthopedic_devices or sternotomy_wires or
electronic_cardiac_devices or cardiac_valve_prosthesis
technical_factors: underinflation or cervical_flexion or patient_rotated or
overexposed or underexposed or incompletely_imaged or image_obscured
ett_no_other_tube: ett and not (ngt or cvc or pac or intercostal_drain)
ngt_no_other_tube: ngt and not (ett or cvc or pac or intercostal_drain)
cvc_no_other_tube: cvc and not (ett or ngt or pac or intercostal_drain)
pac_no_other_tube: pac and not (ett or ngt or cvc or intercostal_drain)
intercostal_drain_no_other_tube: intercostal_drain and not (ett or ngt or cvc or
pac)
lines_and_tubes_with_technical_factors: lines_and_tubes and technical_factors
malpositioned_lines_and_tubes_with_technical_factors: malpositioned_lines_and_tubes
and technical_factors
pneumomediastinum_no_subcutaneous_emphysema: pneumomediastinum and not
subcutaneous_emphysema
pneumomediastinum_no_pneumothorax: pneumomediastinum and not pneumothorax
pneumomediastinum_no_other_features: pneumomediastinum and not (pneumothorax or
subcutaneous_emphysema)
cardiomegaly_no_intervention: cardiomegaly and not (electronic_cardiac_devices or
cardiac_valve_prosthesis or sternotomy_wires or coronary_stent or
intercostal_drain)
cardiomegaly_no_complication: cardiomegaly and not (pulmonary_congestion or
airspace_opacity_without_focus or interstitial_thickening_no_volloss or

TABLE 2-continued pleural_effusion or peribronchial_cuffing)
cardiomegaly_no_features: cardiomegaly and not (electronic_cardiac_devices or
cardiac_valve_prosthesis or sternotomy_wires or coronary_stent or intercostal_drain
or pulmonary_congestion or airspace_opacity_without_focus or
interstitial_thickening_no_volloss or pleural_effusion or peribronchial_cuffing or
unfolded_aorta or aortic_arch_calcification)
cardiomegaly_with_technical_factors: cardiomegaly and technical_factors
airspace_opacity_no_pleural_effusion: airspace_opacity and not pleural_effusion
airspace_opacity_no_cardiomegaly: airspace_opacity and not cardiomegaly
airspace_opacity_with_emphysema: airspace_opacity and (hyperinflation or
hyperlucency or bullae)
airspace_opacity_no_emphysema: airspace_opacity and not (hyperinflation or
hyperlucency or bullae)
airspace_opacity_with_trauma: airspace_opacity and (pneumothorax or
acute_rib_fracture or pneumomediastinum_subcutaneous_emphysema)
airspace_opacity_with_technical_factors: airspace_opacity and technical_factors
interstitial_thickening_volloss_no_linear_atelectasis:
interstitial_thickening_volloss and not linear_atelectasis
interstitial_thickening_volloss_with_technical_factors: interstitial_thickening and
technical_factors
significant_collapse_no_ett: significant_collapse and not ett
significant_collapse_with_ett: significant_collapse and ett
significant_collapse_no_diaphragmatic_elevation: significant_collapse and not
diaphragmatic_elevation
significant_collapse_no_tracheal_deviation: significant_collapse and not
tracheal deviation
significant_collapse_no_linear_atelectasis: significant_collapse and not
linear_atelectasis
significant_collapse_no_interstitial_thickening_volloss: significant_collapse and
not interstitial_thickening_volloss
significant_collapse_with_technical_factors: significant_collapse and
technical_factors
lung_lesion_no_previous_surgery: lung_lesion and not (surgical_clip or lung_sutures
or lung_resection_volloss or rib_resection)
lung_lesion_no_hilar_lymphadenopathy: lung_lesion and not (hilar_lymphadenopathy or
calcified_hilar_lymphadenopathy)
lung_lesion_no_bony_lesion: lung_lesion and not bony_lesions
lung_lesion_no_copd: lung_lesion and not (bullae or hyperinflation or hyperlucency)
lung_lesion_no_osteopenia: lung_lesion and not osteopaenia
lung_lesion_with_technical_factors: lung_lesion and technical_factors
pneumothorax_no_intercostal_drain: pneumothorax and not intercostal_drain
pneumothorax_no_subcutaneous_emphysema: pneumothorax and not subcutaneous_emphysema
pneumothorax_no_bullae: pneumothorax and not bullae
pneumothorax_no_fractures: pneumothorax and not fractures
pneumothorax_with_technical_factors: pneumothorax and technical_factors
pleural_effusion_no_intercostal_drain: pleural_effusion and not intercostal_drain
pleural_effusion_no_cardiomegaly: pleural_effusion and not cardiomegaly
pleural_effusion_no_pleural_thickening: pleural_effusion and not
(diffuse_pleural_thickening or calcified_pleural_plaque or pleural_mass)
pleural_effusion_with_technical_factors: pleural_effusion and technical_factors
pleural_thickening_no_interstitial_thickening_volloss: pleural_thickening and not
interstitial_thickening_volloss
pleural_thickening_with_interstitial_thickening_volloss: pleural_thickening and
interstitial_thickening_volloss
pleural_thickening_no_pleural_effusion: pleural_thickening and not pleural_effusion
pleural_thickening_with_technical_factors: pleural_thickening and technical_factors
rib_lesion_no_other_bony_lesion: rib_lesion and not (humeral_lesion or
clavicle_lesion or scapular_lesion or spine_lesion)
clavicle_lesion_no_other_bony_lesion: clavicle_lesion and not (rib_lesion or
humeral_lesion or scapular_lesion or spine_lesion)
humeral_lesion_no_other_bony_lesion: humeral_lesion and not (rib_lesion or
clavicle_lesion or scapular_lesion or spine_lesion)
scapular_lesion_no_other_bony_lesion: scapular_lesion and not (rib_lesion or
humeral_lesion or clavicle_lesion or spine_lesion)
spine_lesion_no_other_bony_lesion: spine_lesion and not (rib_lesion or
clavicle_lesion or humeral_lesion or scapular_lesion)
bony_lesion_with_technical_factors: bony_lesion and technical_factors
acute _rib_fracture_no_pneumothorax: acute_rib_fracture and not pneumothorax
acute_rib_fracture_no_subcutaneous_emphysema: acute_rib_fracture and not
subcutaneous_emphysema
acute_rib_fracture_no_chronic_rib_fracture: acute_rib_fracture and not
chronic_rib_fracture
acute_rib_fracture_no_other_acute _fractures: acute_rib_fracture and not
(acute_humerus_fracture or acute_clavicle_fracture or scapular_fracture or
spine_wedge_fracture)
acute_rib_fracture_with_technical_factors: acut_rib_fracture and technical_factors
shoulder_dislocation_no_acute_humerus_fracture: shoulder_dislocation and not
acute_humerus_fracture
shoulder_dislocation_no_clavicle fracture: shoulder_dislocation and not
clavicular_fracture

TABLE 2-continued shoulder_dislocation_no_chronic_humerus_fracture: shoulder_dislocation and not chronic_humerus_fracture
acute_humerus_fracture_no_shoulder_dislocation: acute_humerus_fracture and not shoulder_dislocation
osteopaenia_no_spine_wedge_fracture: osteopaenia and not spine_wedge_fracture
spine_wedge_fracture_no_osteopaenia: spine_wedge_fracture and not osteopaenia
distended_bowel_no_perforation: distended_bowel and not subdiaphragmatic_gas
perforation_no_distended_bowel: subdiaphragmatic_gas and not_distended_bowel
osteopaenia_no_copd: osteopaenia and not (bullae or hyperinflation or hyperlucency or airway_stent)
copd_not_osteopaenia: (bullae or hyperinflation or hyperlucency or airway_stent) and notosteopaenia
superior_mediastinal_mass_no_tracheal_deviation: superior_mediastinal_mass and not tracheal_deviation
mastectomy_no_axillary_clips: mastectomy and not axillary_clips
axillary_clips_no_mastectomy: axillary_clips and not mastectomy

TABLE 3

CXR negation pairs.

| | |
|---|---|
| 'pneumothorax', 'subcutaneous_emphysema' | 'pneumothorax', 'intercostal_drain' |
| 'pneumothorax', 'tracheal_deviation' | 'pleural_effusion', 'intercostal_drain' |
| 'pleural_effusion', 'cardiomegaly' | 'significant_collapse', 'ett' |
| 'significant_collapse', 'diaphragmatic_elevation' | 'significant_collapse', 'tracheal_deviation' |
| 'significant_collapse', 'linear_atelectasis' | 'interstitial_thickening_volloss', 'linear_atelectasis' |
| 'interstitial_thickening_volloss_lower', 'linear_atelectasis' | 'interstitial_thickening_volloss_upper', 'interstitial_thickening_upper' |
| 'cavitating_mass', 'cavitating_mass_internal_content' | 'pneumomediastinum', 'subcutaneous_emphysema' |
| 'dish', 'spine_arthritis' | 'shoulder_dislocation', 'acute_humerus_fracture' |
| 'shoulder_dislocation', 'chronic_humerus_fracture' | 'rib_lesion', 'humeral_lesion' |
| 'rib_lesion', 'clavicle_lesion' | 'rib_lesion', 'scapular_lesion' |
| 'rib_lesion', 'spine_lesion' | 'clavicle_lesion', 'spine_lesion' |
| 'scapular_lesion', 'spine_lesion' | 'rib_resection', 'lung_sutures' |
| 'acute_humerus_fracture', 'chronic_humerus_fracture' | 'lung_lesion', 'surgical_clip' |
| 'lung_lesion', 'lung_sutures' | 'lung_lesion', 'lung_resection_volloss' |
| 'bullae', 'hyperinflation' | 'bullae', 'hyperlucency' |
| 'cardiomegaly', 'electronic_cardiac_devices' | 'cardiomegaly', 'cardiac_valve_prosthesis' |
| 'cardiomegaly', 'pulmonary_congestion' | 'cardiomegaly', 'sternotomy_wires' |
| 'cardiomegaly', 'airspace_opacity_without_focus' | 'interstitial_thickening_no_volloss' |
| 'acute_aortic_syndrome', 'tracheal_deviation' | 'aortic_arch_calcification', 'coronary_stent' |
| 'distended_bowel', 'subdiaphragmatic gas' | 'airspace_opacity', 'pleural_effusion' |
| 'airspace_opacity', 'loculated_effusion' | 'ett', 'ngt' |
| 'ett', 'cvc' | 'ett', 'pac' |
| 'ett', 'intercostal_drain' | 'ngt', 'cvc' |
| 'ngt', 'pac' | 'ngt', 'intercostal_drain' |
| 'cvc', 'pac' | 'cvc', 'intercostal_drain' |
| 'pac', 'intercostal_drain' | 'kyphosis', 'scoliosis' |
| 'osteopaenia', 'spine_wedge_fracture' | 'mastectomy', 'axillary_clips' |

TABLE 4

Performance of exemplary models

| label_key | tension_pneumothorax | simple_pneumothorax | pneumothorax |
|---|---|---|---|
| rad_roc_auc_1 | 0.9643 | 0.9692 | 0.9704 |
| rad_roc_auc_2 | 0.9601 | 0.968 | 0.9723 |
| rad_roc_auc_3 | 0.9619 | 0.9667 | 0.9713 |
| rad_roc_auc_4 | 0.9625 | 0.9653 | 0.9726 |

TABLE 4-continued

Performance of exemplary models

| label_key | tension_pneumothorax | simple_pneumothorax | pneumothorax |
|---|---|---|---|
| rad_roc_auc_5 | 0.9589 | 0.9722 | 0.9736 |
| rad_roc_auc_mean | 96% | 97% | 97% |
| rad_roc_auc_std | 0.002 | 0.002 | 0.001 |
| model_roc_auc_hopeful-donkey-583_2h45vvhs | 98% | 97% | 98% |
| model_roc_auc_unique-wildflower-596_8hp45vkw | 98% | 98% | 98% |
| model_roc_auc_gentle-fire-598_36kpxjvu | 98% | 97% | 98% |
| model_roc_auc_mean | 98% | 98% | 98% |
| model_roc_auc_std | 0.002 | 0.0005 | 0.0004 |
| delta | 2% | 1% | 0% |
| combined_std | 0% | 0% | 0% |
| upper_bound | 2% | 1% | 1% |
| lower_bound | 1% | 0% | 0% |

The invention claimed is:

1. A method for detecting a plurality of visual findings in one or more anatomical images of a subject, comprising:
   providing one or more anatomical images of the subject;
   inputting the one or more anatomical images into a first convolutional neural network (CNN) component of a primary neural network to output a feature vector;
   computing an indication of a plurality of visual findings being present in at least one of the one or more anatomical images by a dense layer of the primary neural network that takes as input the feature vector and outputs an indication of whether each of the plurality of visual findings is present in at least one of the one or more anatomical images,
   wherein the primary neural network is trained on a training dataset including, for each of a plurality of subjects, one or more anatomical images, and a plurality of labels associated with the one or more anatomical images and each of the respective visual findings, wherein the primary neural network is trained by evaluating performance of a plurality of neural networks in detecting the plurality of visual findings, wherein the performance evaluation comprises accounting for correlation between one or more pairs of the plurality of visual findings.

2. The method of claim 1 wherein the visual findings are radiological findings in anatomical images comprising one or more chest x-ray (CXR) images.

3. The method of claim 1 wherein accounting for correlation between one or more pairs of the plurality of visual findings comprises evaluating the performance of each of the plurality of neural networks using a testing dataset that comprises a subset of the training dataset, where the testing dataset is selected such that the correlation between the one or more pairs of the plurality of findings in the testing dataset satisfies one or more criteria selected from:
   the correlation between the one or more pairs of the plurality of findings in the validation dataset does not differ by more than a predetermined percentage from the corresponding correlation in the full training dataset; and
   the correlation between the one or more pairs of the plurality of findings in the validation dataset does not exceed a predetermined threshold.

4. A method for detecting a plurality of visual findings in one or more anatomical images of a subject, comprising:
   providing one or more anatomical images of a subject;
   inputting the one or more anatomical images into a first convolutional neural network (CNN) component of a primary neural network to output a feature vector;
   computing an indication of a plurality of visual findings being present in at least one of the one or more anatomical images by a dense layer of the primary neural network that takes as input the feature vector and outputs an indication of whether each of the plurality of visual findings is present in at least one of the one or more anatomical images,
   wherein the primary neural network is trained on a training dataset including, for each of a plurality of subjects, one or more anatomical images, and a plurality of labels associated with the one or more anatomical images and each of the respective visual findings, wherein the plurality of visual findings is organised as a hierarchical ontology tree and the training comprises evaluating performance of the neural network at different levels of the hierarchy of the ontology tree.

5. The method of claim 4 wherein the visual findings are radiological findings in anatomical images comprising one or more chest x-ray (CXR) images.

6. The method of claim 4 wherein:
   the hierarchical ontology tree comprises internal nodes and terminal leaves; at least one of the plurality of labels is associated with a terminal leaf in the hierarchical ontology tree, and at least one of the plurality of labels is associated with an internal node in the hierarchical ontology tree; and
   the primary neural network outputs an indication of whether each of the plurality of visual findings is present in at least one of the one or more anatomical images, for visual findings that include internal nodes and terminal leaves.

7. A method for detecting a plurality of visual findings in one or more anatomical images of a subject, comprising:
   providing one or more anatomical images of a subject;
   inputting the one or more anatomical images into a first convolutional neural network (CNN) component of a primary neural network to output a feature vector;
   computing an indication of a plurality of visual findings being present in at least one of the one or more anatomical images by a dense layer of the primary neural network that takes as input the feature vector and outputs an indication of whether each of the plurality of visual findings is present in at least one of the one or more anatomical images,
wherein the primary neural network is trained on a training dataset including, for each of a plurality of subjects, one or more anatomical images, and a plurality of labels associated with the one or more anatomical images and each of the respective visual findings, wherein the plurality of visual findings is organised as a hierarchical ontology tree, and
wherein the primary neural network is trained by evaluating the performance of a plurality of neural networks in detecting the plurality of visual findings and at least one negation pair class which comprises anatomical images where a first one of the plurality of visual findings is identified in the absence of a second one of the plurality of visual findings.

8. The method of claim 1 wherein the one or more anatomical images comprise at least one image that is captured by an imaging device when the subject is oriented anterior-posterior (AP) or posterior-anterior (PA) relative to the imaging device and at least one image that is captured by an imaging device when the subject is oriented laterally relative to the imaging device.

9. The method of claim 8 wherein the one or more anatomical images comprise at least one image that is captured by an imaging device when the subject is oriented anterior-posterior (AP) relative to the imaging device, at least one image that is captured by an imaging device when the subject is oriented poster-anterior (PA) relative to the imaging device, and at least one image that is captured by an imaging device when the subject is oriented laterally relative to the imaging device.

10. The method of claim 8 further comprising:
inputting an anatomical image of the at least two anatomical images captured at different orientations into a further CNN component of a further neural network to output a further feature vector; and
inputting the further feature vector into a dense layer of the further neural network to generate an indication of orientation of the input anatomical image.

11. The method of claim 10 wherein the primary neural network further comprises at least a second CNN component, and the method further comprises:
inputting a first anatomical image of the at least two anatomical images captured at different orientations into the first CNN component of the primary neural network to output a first feature vector;
inputting a second anatomical image of the at least two anatomical images captured at different orientations into the second CNN component of the primary neural network to output a second feature vector; and
inputting a feature vector that combines the first feature vector and the second feature vector into the dense layer of the primary neural network.

12. The method of claim 11 wherein the at least two anatomical images captured at different orientations comprise a third anatomical image, the primary neural network further comprises a third CNN component, and the method further comprises:
inputting the third anatomical image into the third CNN component of the primary neural network to output a third feature vector; and
inputting a feature vector that combines the first feature vector, the second feature vector and the third feature vector into the dense layer of the primary neural network.

13. The method of claim 11 wherein the first and second CNN components comprise a shared CNN component.

14. The method of claim 12 wherein at least two of the first, second, and third CNN components comprise a shared CNN component.

15. A method for training a neural network to detect a plurality of visual findings in one or more anatomical images of a subject, comprising:
providing a primary neural network comprising a first convolutional neural network (CNN) component that takes as input one or more anatomical images of a subject and outputs a first feature vector, and a dense layer that takes as input a feature vector comprising the first feature vector and outputs an indication of whether each of the plurality of visual findings is present in at least one of the one or more anatomical images;
retrieving, from a data store, a training dataset including, for each of a plurality of subjects, one or more anatomical images, and a plurality of labels associated with the one or more anatomical images and each of the respective visual findings; and
training the primary neural network using the training dataset,
wherein the training comprises evaluating performance of the primary neural network in detecting the plurality of visual findings relative to one or more similar neural networks, wherein the performance evaluation comprises accounting for correlation between one or more pairs of the plurality of visual findings.

16. The method of claim 15 wherein accounting for correlation between one or more pairs of the plurality of visual findings comprises evaluating the performance of each of the plurality of neural networks using a testing dataset that comprises a subset of the training dataset, where the testing dataset is selected such that the correlation between the one or more pairs of the plurality of findings in the testing dataset satisfies one or more criteria selected from:
the correlation between the one or more pairs of the plurality of findings in the validation dataset does not differ by more than a predetermined percentage from the corresponding correlation in the full training dataset; and
the correlation between the one or more pairs of the plurality of findings in the validation dataset does not exceed a predetermined threshold.

17. The method of claim 15 wherein accounting for correlation between one or more pairs of the plurality of visual findings comprises evaluating the performance of each of the plurality of neural networks for each of the plurality of visual findings and at least one negation pair class which comprises anatomical images where a first one of the plurality of visual findings is identified in the absence of a second one of the plurality of visual findings.

18. A method for training a neural network to detect a plurality of visual findings in one or more anatomical images of a subject, comprising:
providing a primary neural network comprising a first convolutional neural network (CNN) component that takes as input one or more anatomical images of a subject and outputs a first feature vector, and a dense layer that takes as input a feature vector comprising the first feature vector and outputs an indication of whether each of the plurality of visual findings is present in at least one of the one or more anatomical images;
retrieving, from a data store, a training dataset including, for each of a plurality of subjects, one or more anatomical images, and a plurality of labels associated with the one or more anatomical images and each of the respective visual findings; and training the primary neural network using the training dataset, wherein the plurality of visual findings is organised as a hierarchical ontology tree, and the training comprises evaluating performance of the primary neural network at different levels of the hierarchy of the ontology tree.

19. The method of claim 18 wherein:

the hierarchical ontology tree comprises internal nodes and terminal leaves;

at least one of the plurality of labels is associated with a terminal leaf in the hierarchical ontology tree, and at least one of the plurality of labels is associated with an internal node in the hierarchical ontology tree; and the primary neural network outputs an indication of whether each of the plurality of visual findings is present in at least one of the one or more anatomical images, for visual findings that include internal nodes and terminal leaves.

20. The method of claim 18 wherein the plurality of labels associated with at least a subset of the one or more anatomical images and each of the respective visual findings in the training dataset may be derived from the results of review of the one or more anatomical images by at least one expert.

21. The method of claim 20 wherein review of the one or more anatomical images comprises, by the at least one expert, using a labelling tool that allows the expert to select labels presented in a hierarchical menu.

22. A method for training a neural network to detect a plurality of visual findings in one or more anatomical images of a subject, comprising:

providing a primary neural network comprising a first convolutional neural network (CNN) component that takes as input one or more anatomical images of a subject and outputs a first feature vector, and a dense layer that takes as input a feature vector comprising the first feature vector and outputs an indication of whether each of the plurality of visual findings is present in at least one of the one or more anatomical images;

retrieving, from a data store, a training dataset including, for each of a plurality of subjects, one or more anatomical images, and a plurality of labels associated with the one or more anatomical images and each of the respective visual findings; and training the primary neural network using the training dataset, wherein the plurality of visual findings is organised as a hierarchical ontology tree, and the training comprises evaluating performance of the primary neural network at different levels of the hierarchy of the ontology tree, and wherein the training further comprises evaluating performance of the primary neural network in detecting the plurality of visual findings, and at least one negation pair class which comprises anatomical images where a first one of the plurality of visual findings is identified in the absence of a second one of the plurality of visual findings, relative to one or more similar neural networks.

23. The method of claim 22 wherein evaluating the performance of the primary neural network for each of the plurality of visual findings and at least one negation pair class comprises computing a combined performance across the plurality of visual findings and the at least one negation pair class.

24. The method of claim 22 wherein the primary neural network is further trained by evaluating performance of a plurality of neural networks in detecting the plurality of visual findings, wherein the performance evaluation comprises accounting for correlation between one or more pairs of the plurality of visual findings.

* * * * *